United States Patent
Edgar et al.

(10) Patent No.: US 11,445,802 B2
(45) Date of Patent: Sep. 20, 2022

(54) SYSTEM AND METHOD FOR APPLYING A REFLECTANCE MODIFYING AGENT TO IMPROVE THE VISUAL ATTRACTIVENESS OF HUMAN SKIN

(71) Applicant: TCMS Transparent Beauty LLC, Austin, TX (US)

(72) Inventors: Albert D. Edgar, Austin, TX (US); David C. Iglehart, Wimberley, TX (US); Rick B. Yeager, Austin, TX (US)

(73) Assignee: TCMS Transparent Beauty, LLC, Austin, TX (US)

( * ) Notice: Subject to any disclaimer, the term of this patent is extended or adjusted under 35 U.S.C. 154(b) by 1019 days.

(21) Appl. No.: 16/029,984

(22) Filed: Jul. 9, 2018

(65) Prior Publication Data

US 2018/0310693 A1  Nov. 1, 2018

Related U.S. Application Data

(63) Continuation of application No. 14/571,815, filed on Dec. 16, 2014, now Pat. No. 10,016,046, which is a (Continued)

(51) Int. Cl.
 A45D 44/00 (2006.01)
 B41J 3/407 (2006.01)
 (Continued)

(52) U.S. Cl.
 CPC ......... *A45D 44/005* (2013.01); *A45D 40/30* (2013.01); *A61B 5/0064* (2013.01); *A61B 5/442* (2013.01);
 (Continued)

(58) Field of Classification Search
 CPC .............................. A61B 5/0064; A61B 5/444
 See application file for complete search history.

(56) References Cited

U.S. PATENT DOCUMENTS 4,190,056 A  2/1980  Tapper et al.
4,401,122 A  8/1983  Clark
(Continued)

FOREIGN PATENT DOCUMENTS

CN  101287607 B  10/2008
DE  202004003148 U1  3/2005
(Continued)

OTHER PUBLICATIONS

"Automated feature detection in digital images of skin" by R.G. White et al. vol. 34 Issue 1. 1991. pp. 41-60 (Year: 1991).*
(Continued)

*Primary Examiner* — Jason M Ip
(74) *Attorney, Agent, or Firm* — Fish & Richardson P.C.

(57) ABSTRACT

A computer-controlled system determines attributes of a frexel, an area of human skin, and applies a modifying agent (RMA) at the pixel level, typically to make the skin appear more youthful and so more attractive. The system scans the frexel, identifies unattractive attributes, and applies the RMA, typically with an inkjet printer. The identified attributes relate to reflectance and may refer to features such as irregular-looking light and dark spots, age-spots, scars, and bruises. Identified attributes may also relate to the surface topology of the skin, for more precisely enhancing surface irregularities such as bumps and wrinkles. Feature mapping may be used, for example to make cheeks appear pinker and cheekbones more prominent. The RMA can be applied in agreement with identified patterns, such as adding red to a red frexel, or in opposition, such as adding green or blue to a red frexel, according to idealized models of attractiveness.

19 Claims, 47 Drawing Sheets

Related U.S. Application Data continuation of application No. 13/183,227, filed on Jul. 14, 2011, now Pat. No. 8,915,562, which is a continuation of application No. 11/503,806, filed on Aug. 14, 2006, now Pat. No. 8,007,062.

(60) Provisional application No. 60/708,118, filed on Aug. 12, 2005.

(51) Int. Cl.
  *G06T 7/90*   (2017.01)
  *A61M 35/00*  (2006.01)
  *A61B 5/00*   (2006.01)
  *H04N 1/62*   (2006.01)
  *G06V 10/56*  (2022.01)
  *G06V 40/16*  (2022.01)
  *B41J 3/36*   (2006.01)
  *A45D 40/30*  (2006.01)

(52) U.S. Cl.
  CPC ............ *A61B 5/444* (2013.01); *A61B 5/6888* (2013.01); *B41J 3/36* (2013.01); *B41J 3/407* (2013.01); *B41J 3/4073* (2013.01); *G06T 7/90* (2017.01); *G06V 10/56* (2022.01); *G06V 40/168* (2022.01); *G06V 40/171* (2022.01); *H04N 1/628* (2013.01); *A61M 35/00* (2013.01); *A61M 35/25* (2019.05)

(56) References Cited

U.S. PATENT DOCUMENTS

| | | |
|---|---|---|
| 4,628,356 A | 12/1986 | Spillman et al. |
| 4,771,060 A | 9/1988 | Nakagawa |
| 4,807,991 A | 2/1989 | Carew |
| 4,882,492 A | 11/1989 | Schlager |
| 5,027,817 A | 7/1991 | John |
| 5,156,479 A | 10/1992 | Iizuka |
| 5,241,468 A | 8/1993 | Kenet |
| 5,268,166 A | 12/1993 | Barnett et al. |
| 5,431,911 A | 7/1995 | Reynolds |
| 5,836,872 A | 11/1998 | Kenet |
| 5,931,166 A | 8/1999 | Weber et al. |
| 6,021,344 A | 2/2000 | Lui et al. |
| 6,067,996 A | 5/2000 | Weber et al. |
| 6,111,653 A | 8/2000 | Bucknell et al. |
| 6,122,042 A | 9/2000 | Wunderman et al. |
| 6,151,031 A | 11/2000 | Atkins |
| 6,208,749 B1 | 3/2001 | Gutkowicz-Krusin et al. |
| 6,250,927 B1 | 6/2001 | Narlo |
| 6,286,517 B1 | 9/2001 | Weber et al. |
| 6,292,277 B1 | 9/2001 | Kikinis |
| 6,293,284 B1 | 9/2001 | Rigg |
| 6,295,737 B2 | 10/2001 | Patton et al. |
| 6,312,124 B1 | 11/2001 | Desormeaux |
| 6,341,831 B1 | 1/2002 | Weber et al. |
| 6,385,487 B1 | 5/2002 | Henley |
| 6,436,127 B1 | 8/2002 | Anderson et al. |
| 6,477,410 B1 | 11/2002 | Henley |
| 6,487,440 B2 | 11/2002 | Deckert et al. |
| 6,502,583 B1 | 1/2003 | Utsugi |
| 6,543,893 B2 | 4/2003 | Desormeaux |
| 6,554,452 B1 | 4/2003 | Bourn et al. |
| 6,575,751 B1 | 6/2003 | Lehman |
| 6,578,276 B2 | 6/2003 | Patton |
| 6,641,578 B2 | 11/2003 | Mukai |
| 6,706,035 B2 | 3/2004 | Cense et al. |
| 6,719,467 B2 | 4/2004 | Hess et al. |
| 6,810,130 B1 | 10/2004 | Aubert et al. |
| 7,027,619 B2 | 4/2006 | Pavlidis et al. |
| 7,233,693 B2 | 6/2007 | Momma |
| 7,369,692 B2 | 5/2008 | Shirai et al. |
| 7,382,400 B2 | 6/2008 | Sablak |
| 7,433,102 B2 | 10/2008 | Takahashi et al. |
| 7,602,942 B2 | 10/2009 | Bazakos et al. |
| 7,890,152 B2 | 2/2011 | Edgar et al. |
| 8,007,062 B2 | 8/2011 | Edgar et al. |
| 8,026,942 B2 | 9/2011 | Payonk |
| 8,027,505 B2 | 9/2011 | Edgar |
| 8,182,425 B2 | 5/2012 | Stamatas |
| 8,184,901 B2 | 5/2012 | Edgar et al. |
| 8,231,292 B2 | 7/2012 | Rabe |
| 8,384,793 B2 | 2/2013 | Ciuc |
| 8,464,732 B2 | 6/2013 | Wong |
| 8,582,830 B2 | 11/2013 | Edgar et al. |
| 8,610,767 B2 | 12/2013 | Uzenbajakava et al. |
| 8,695,610 B2 | 4/2014 | Samain |
| 8,899,242 B2 | 12/2014 | Wong |
| 8,908,904 B2 | 12/2014 | Santos et al. |
| 8,915,562 B2 | 12/2014 | Edgar |
| 8,942,775 B2 | 1/2015 | Edgar |
| 8,977,389 B2 | 3/2015 | Witchell |
| 9,135,726 B2 | 9/2015 | Kafuku |
| 9,247,802 B2 | 2/2016 | Edgar |
| 9,277,799 B2 | 3/2016 | Takaleh |
| 9,333,156 B2 | 5/2016 | Ito |
| 9,437,026 B2 | 9/2016 | Kafuku et al. |
| 9,449,382 B2 | 9/2016 | Edgar |
| 9,754,351 B2 | 9/2017 | Paluri et al. |
| 9,984,282 B2 | 5/2018 | Chen et al. |
| 10,016,046 B2 | 7/2018 | Edgar |
| 10,043,292 B2 | 8/2018 | Edgar |
| 10,049,433 B2 | 8/2018 | Lin |
| 10,092,082 B2 | 10/2018 | Edgar |
| 10,270,983 B1 | 4/2019 | Van Os et al. |
| 10,325,417 B1 | 6/2019 | Scapel et al. |
| 10,362,219 B2 | 7/2019 | Wilson et al. |
| 10,375,313 B1 | 8/2019 | Van Os et al. |
| 10,379,719 B2 | 8/2019 | Scapel et al. |
| 10,410,434 B1 | 9/2019 | Scapel et al. |
| 2001/0040982 A1 | 11/2001 | Kim |
| 2002/0054714 A1 | 5/2002 | Hawkins et al. |
| 2002/0064302 A1 | 5/2002 | Massengill |
| 2002/0070988 A1 | 6/2002 | Desormeaux |
| 2002/0081003 A1 | 6/2002 | Sobol |
| 2002/0105662 A1 | 8/2002 | Patton |
| 2002/0107456 A1 | 8/2002 | Leveque |
| 2002/0128780 A1 | 9/2002 | De Rigal et al. |
| 2002/0155069 A1 | 10/2002 | Pruche et al. |
| 2002/0172419 A1 | 11/2002 | Lin et al. |
| 2002/0176926 A1 | 11/2002 | Pletcher et al. |
| 2003/0010083 A1 | 1/2003 | Minnerop et al. |
| 2003/0045799 A1 | 3/2003 | Bazin et al. |
| 2003/0050561 A1 | 3/2003 | Bazin et al. |
| 2003/0053664 A1 | 3/2003 | Pavlidis et al. |
| 2003/0053685 A1 | 3/2003 | Lestideau |
| 2003/0060810 A1 | 3/2003 | Syrowicz et al. |
| 2003/0062058 A1 | 4/2003 | Utsugi |
| 2003/0063102 A1 | 4/2003 | Rubinstenn et al. |
| 2003/0067545 A1 | 4/2003 | Giron et al. |
| 2003/0100837 A1 | 5/2003 | Lys et al. |
| 2003/0108228 A1 | 6/2003 | Garnier |
| 2003/0130575 A1 | 7/2003 | Desai |
| 2003/0208190 A1 | 11/2003 | Roberts et al. |
| 2003/0223622 A1 | 12/2003 | Simon |
| 2003/0229514 A2 | 12/2003 | Brown |
| 2004/0005086 A1 | 1/2004 | Wolff et al. |
| 2004/0007827 A1 | 1/2004 | Hahn |
| 2004/0073186 A1 | 4/2004 | Cameron |
| 2004/0078278 A1 | 4/2004 | Dauga et al. |
| 2004/0125996 A1 | 7/2004 | Eddowes et al. |
| 2004/0170337 A1 | 9/2004 | Simon et al. |
| 2004/0174525 A1 | 9/2004 | Mullani |
| 2004/0179101 A1 | 9/2004 | Bodnar et al. |
| 2004/0201694 A1 | 10/2004 | Gartstein et al. |
| 2004/0236229 A1 | 11/2004 | Freeman et al. |
| 2004/0254546 A1 | 12/2004 | Lefebvre |
| 2004/0257439 A1 | 12/2004 | Shirai et al. |
| 2004/0267189 A1 | 12/2004 | Mavor et al. |
| 2005/0004475 A1 | 1/2005 | Giron |
| 2005/0010102 A1 | 1/2005 | Marchesini et al. |
| 2005/0019285 A1 | 1/2005 | Lee et al. |
| 2005/0053628 A1 | 3/2005 | Montanari et al. |

(56) References Cited

U.S. PATENT DOCUMENTS

| | | |
|---|---|---|
| 2005/0053637 A1 | 3/2005 | Ma Or et al. |
| 2005/0063197 A1 | 3/2005 | Nightingale et al. |
| 2005/0069208 A1 | 3/2005 | Morisada |
| 2005/0154382 A1 | 7/2005 | Altshuler |
| 2006/0104507 A1 | 5/2006 | John |
| 2006/0153470 A1 | 7/2006 | Simon et al. |
| 2006/0228037 A1 | 10/2006 | Simon |
| 2006/0228038 A1 | 10/2006 | Simon et al. |
| 2006/0228039 A1 | 10/2006 | Simon et al. |
| 2006/0228040 A1 | 10/2006 | Simon et al. |
| 2006/0282137 A1 | 12/2006 | Nightingale et al. |
| 2007/0016078 A1 | 1/2007 | Hoyt et al. |
| 2007/0035815 A1 | 2/2007 | Edgar et al. |
| 2007/0047761 A1 | 3/2007 | Wasilunas et al. |
| 2007/0049832 A1 | 3/2007 | Edgar et al. |
| 2007/0134192 A1 | 6/2007 | Shimizu |
| 2007/0203413 A1 | 8/2007 | Frangioni |
| 2007/0255589 A1 | 11/2007 | Rodriguez |
| 2008/0192999 A1 | 8/2008 | Edgar et al. |
| 2008/0193195 A1 | 8/2008 | Edgar et al. |
| 2008/0194971 A1 | 8/2008 | Edgar et al. |
| 2008/0219528 A1 | 9/2008 | Edgar et al. |
| 2009/0025747 A1 | 1/2009 | Edgar et al. |
| 2009/0209833 A1 | 8/2009 | Waagan et al. |
| 2009/0231356 A1 | 9/2009 | Barnes |
| 2010/0114265 A1 | 5/2010 | Lechthaler |
| 2010/0139682 A1 | 6/2010 | Edgar et al. |
| 2010/0224205 A1 | 9/2010 | Mitra et al. |
| 2010/0224211 A1 | 9/2010 | Rabe et al. |
| 2011/0124989 A1 | 5/2011 | Edgar et al. |
| 2011/0270200 A1 | 11/2011 | Edgar |
| 2012/0299945 A1 | 11/2012 | Aarabi |
| 2013/0149365 A1 | 6/2013 | Rajagopal et al. |
| 2013/0302078 A1 | 11/2013 | Edgar |
| 2014/0050377 A1 | 2/2014 | Edgar et al. |
| 2015/0196109 A1 | 7/2015 | Edgar |
| 2015/0237991 A1 | 8/2015 | Edgar |
| 2015/0359315 A1 | 12/2015 | Rabe |
| 2015/0359714 A1 | 12/2015 | Rabe |
| 2017/0004635 A1 | 1/2017 | Edgar |
| 2017/0256084 A1 | 9/2017 | Iglehart |
| 2018/0033161 A1 | 2/2018 | Nichol et al. |
| 2018/0315219 A1 | 11/2018 | Edgar et al. |
| 2019/0096097 A1 | 3/2019 | Edgar et al. |

FOREIGN PATENT DOCUMENTS

| | | | |
|---|---|---|---|
| EP | 1184663 | A2 | 3/2002 |
| EP | 1210909 | A2 | 6/2002 |
| EP | 1304056 | A2 | 4/2003 |
| EP | 1495781 | A2 | 1/2005 |
| EP | 1677254 | A1 | 7/2006 |
| EP | 1763380 | A1 | 3/2007 |
| FR | 2810761 | | 12/2001 |
| JP | 59171280 | | 9/1984 |
| JP | 05281041 | | 10/1993 |
| JP | 06201468 | | 7/1994 |
| JP | 11019050 | | 1/1999 |
| JP | 11019051 | | 1/1999 |
| JP | 2000139846 | | 5/2000 |
| JP | 2000331167 | | 11/2000 |
| JP | 2001112722 | | 4/2001 |
| JP | 2002017689 | | 1/2002 |
| JP | 2002263084 | | 9/2002 |
| JP | 2003052642 | | 2/2003 |
| JP | 2003057169 | | 2/2003 |
| JP | 2003057170 | | 2/2003 |
| JP | 2003513735 | | 4/2003 |
| JP | 2003519019 | | 6/2003 |
| JP | 2003210248 | | 7/2003 |
| JP | 2004501707 | | 1/2004 |
| JP | 2004105748 | | 4/2004 |
| JP | 2004315416 | | 11/2004 |
| JP | 2004315426 | | 11/2004 |
| JP | 2008526284 | | 7/2006 |
| JP | 2006271654 | | 10/2006 |
| JP | 2007231883 | | 9/2007 |
| JP | 2008526241 | | 7/2008 |
| RU | 2336866 | | 10/2008 |
| WO | WO2001026735 | A1 | 4/2001 |
| WO | WO2001049360 | A1 | 7/2001 |
| WO | WO2001077976 | A2 | 10/2001 |
| WO | WO2004028420 | A1 | 4/2004 |
| WO | WO2004091590 | A1 | 10/2004 |
| WO | WO2004095372 | | 11/2004 |
| WO | WO2005123172 | A1 | 12/2005 |
| WO | WO2006008414 | | 1/2006 |
| WO | WO2006074881 | A1 | 7/2006 |
| WO | WO2007022095 | | 2/2007 |

OTHER PUBLICATIONS

"MasqueArray: Automatic makeup selector/applicator" by C. Jeamsinkul. RIT Scholar Works. Nov. 11, 1998. (Year: 1998).*
Examination Report for Canadian Patent Application No. 2,985,955, dated Aug. 14, 2018, 6 pages.
European Examination Report for Application No. 11160161.3 dated Nov. 22, 2018, 6 pages.
"Lehrstuhl für Optik 2004 Annual Report" Jun. 2005 (2005-2006), Lehrstuhl Für Optik, Institute Für Optik, Information und Photonik, Max-Planck-Forschungsgruppe, Universität Erlangen-Nürnberg, Erlangen, Germany, XP002460048, 2 pages.
European, EPO Office Action in App. No. 06 801 295.4, datedFeb. 3, 2010, 3 pages. (002EP).
Authorized Officer Nora Lindner, International Preliminary Report on Patentability and Written Opinion of the International Searching Authority for International Application No. PCT/US2006/031441, dated Feb. 12, 2008, 9 pages. (002WO).
Russian, Russian Official Action (including translation) for Application No. 2008109234, dated Apr. 2, 2009, 7 pages.
European, EPO Office Action in Application No. 06 801 295.4, dated Jun. 10, 2008, 3 pages.
Authorized Officer Moritz Knupling, International Search Report for International Application No. PCT/US2006/031441, dated Dec. 7, 2007, 2 pages.
Authorized Officer Lars-Oliver Romich, International Search Report and the Written Opinion for International Application No. PCT/US2006/031441, dated Dec. 7, 2007, 14 pages.
Chinese, Notification of the First Office Action (including translation) in Application No. 200680037564.6, dated Jul. 31, 2009, 7 pages.
Australian, Examiner's First Report in Application No. 2006279800, dated Feb. 2, 2011, 2 pages.
Russian Deputy Chief S.V. Artamonov, Decision on Grant Patent For Invention (including translation) in Application 2008109235, dated Feb. 19, 2009.
Authorized Officer Dorothee Mulhausen, International Preliminary Report on Patentability for International Application No. PCT/US2006/031657, dated Feb. 12, 2008, 7 pages.
Authorized Officer Laure Acquaviva, Invitation to Pay Additional Fees and, where applicable, Protest Fees International Application No. PCT/US2008/053527, mailed Jul. 7, 2008, 8 pages.
Australian, Examiner's First Report in Application No. 2006279652, dated Jan. 28, 2011, 2 pages.
Chinese, Notification of the First Office Action (including translation) in Application No. 200680037560.8, dated Jul. 17, 2009, 8 pages.
European, EPO Office Action in Application No. 06 789 746.2, dated Apr. 3, 2009, 3 pages.
Authorized Officer Wolfhard Wehr, International Search Report for International Application No. PCT/US2006/031657, dated Dec. 20, 2006, 2 pages.
Authorized Officer Athina Nickitas-Etienne, International Preliminary Report on Patentability for International Application No. PCT/US2008/053640, dated Aug. 19, 2009, 5 pages.
Authorized Officer Michael Eberwein, International Search Report and Written Opinion for International Application No. PCT/US2008/053640, dated Jun. 3, 2008, 9 pages.

(56) References Cited

OTHER PUBLICATIONS

European Patent Office Action for Application No. 08 729 481.5, dated Aug. 23, 2010, 5 pages.
Authorized Officer Jens Clevorn, International Search Report for Application No. PCT/US2008/053528, dated Nov. 13, 2008, 4 pages.
Authorized Officer Jens Clevorn, International Preliminary Report on Patentability and Written Opinion of the International Searching Authority for Application No. PCT/US2008/053528, dated Aug. 11, 2009, 9 pages.
Notification of First Office Action for Application No. 200880009579.0, dated Jul. 14, 2010, 10 pages.
Authorized Officer Simin Baharlou, International Preliminary Report on Patentability and Written Opinion of the International Searching Authority for Application No. PCT/US2008/065168, dated Dec. 1, 2009, 8 pages.
Anonimous, "Circular Polarizer Films," Internet Article, [Online] 2005, http://www.optigrafix.com/circular.htm [retrieved on Sep. 5, 2008].
Authorized Officer Carlos Nicolas, International Search Report and Written Opinion for Application No. PCT/US2008/065168, dated Sep. 19, 2008, 13 pages.
Examination Report for European Application No. 08769826.2, dated Jul. 16, 2013, 6 pages.
Mike Topping et al., "The Development of Handy 1, A Robotic System to Assist the Severely Disabled," ICORR '99, Sixth International Conference of Rehabilitation Robotics, Stanford, CA, Jul. 1-2, 1999, pp. 244-249.
Robot News, "Handy 1—Rehabilitation robot for the severely disabled; helping you to eat and drink and brush and even do make-up!", posted on Apr. 3, 2006, http://robotnews.wordpress.com/2006/04/03/handy1-rehabiliation-robot-for-the-severely-disabledhelping-you-to-eat-and-drink-and-brush-and-even-do-make-up/, 6 pages.
Mike Topping, "An Overview of the Development of Handy 1, a Rehabilitation Robot to Assist the Severely Disabled" Journal of Intelligent and Robotic Systems, vol. 34, No. 3, 2002, pp. 253-263.
Notice of Reasons for Rejection for Application No. 2008-526241, dated Aug. 31, 2011, 7 pages.
Chinese, Notification of the First Office Action (including translation) in Application No. 200880009069.3, dated Jul. 1, 2011, 8 pages.
European, EPO Office Action in App. No. 06 801 295.4, dated Oct. 10, 2011, 5 pages. (002EP).
Cula O G et al., "Bidirectional Imaging and Modeling of Skin Texture," IEEE Transactions On Biomedical Engineering, IEEE Service Center, Piscataway, NJ, USA, vol. 51, No. 12, Dec. 1, 2004, pp. 2148-2159.
Australian, Second Examiner's Report in Application No. 2006279652, dated Nov. 3, 2011, 2 pages.
Francois-Xavier Bon et al., "Quantitative and Kinetic Evolution of Wound Healing through Image Analysis," 2000 IEEE Transactions on Medical Imaging, vol. 19, No. 7, Jul. 2000, pp. 767-772.
Divya Railan et al., "Laser Treatment of Acne, Psoriasis, Leukoderma and Scars," Seminars in Cutaneous Medicine and Surgery, Dec. 2008, pp. 285-291.
Robert J. Chiu et al., "Fractionated Photothermolysis: The Fraxel 1550-nm Glass Fiber Laser Treatment," Facial Plastic Surgery Clinics of North America (2007), vol. 15, Issue 2, May 2007, pp. 229-237.

Hans Laubach et al., "Effects of Skin Temperature on Lesion Size in Fractional Photothermolysis," Lasers in Surgery and Medicine, Jan. 2007, pp. 14-18.
Oana G. Cula et al., "Bidirectional Imaging and Modeling of Skin Texture," IEEE Engineering of Medicine and Biology Society, Nov. 2004, pp. 1-6.
Australian, Examiner's First Report in Application No. 2008260040, dated Apr. 13, 2012, 2 pages.
Korean, Notice to File a Response in Application No. 10-2008-7006079, dated Aug. 6, 2012, 10 pages.
Korean, Notice to File a Response in Application No. 10-2008-7006079, dated Jun. 25, 2013, 5 pages.
Notice of Reasons for Rejection for Application No. 2008-526284, dated Apr. 18, 2012, 10 pages.
Notification of the Second Office Action for Application No. 200880009579.0, dated Mar. 1, 2012, 4 pages.
Russian, Office Action for Application No. 2009148819, dated May 30, 2012, 7 pages.
Notification of the Third Office Action for Application No. 200880009579.0, dated Jan. 7, 2013, 8 pages.
Korean Notice to File a Response in Application No. 10-2008-7006041, dated Jan. 29, 2013, 10 pages.
Chujit Jeamsinkul, "MasqueArray Automatic Makeup Selector/Applicator", Nov. 11, 1998, Rochester Institute of Technology, 79 pages.
Office Action for Japanese Patent Application No. 2009-549296, dated Apr. 30, 2013, 12 pages.
Office Action for Korean Patent Application No. 10-2009-7019063, dated Mar. 24, 2014, 8 pages.
Examination Report for Canadian Patent Application No. 2,618,706, dated Jul. 31, 2014, 3 pages.
Weyrich et al., "Analysis of Human Faces using a Measurement-Based Skin Reflectance Model," Association for Computing Machinery, Inc. 2006, pp. 1-12 (1013-1024).
Donner et al., "A Layered, Heterogeneous Reflectance Model for Acquiring and Rendering Human Skin" ACM Transactions on Graphics, vol. 27, No. 5, Article 140, Publication date: Dec. 2008 pp. 1-12.
Examination Report for Canadian Patent Application No. 2,618,519, dated Jan. 16, 2015, 2 pages.
Examination Report for Australian Patent Application No. 2013200395, dated Feb. 5, 2015, 4 pages.
Examination Report for Canadian Patent Application No. 2,618,706, dated Jul. 30, 2015, 4 pages.
Examination Report for Canadian Patent Application No. 2,618,519, dated Jul. 9, 2015, 3 pages.
Patent Examination Report No. 1 for Australian Patent Application No. 2014200087, dated Jun. 30, 2015, 3 pages.
Examination Report for Canadian Patent Application No. 2,618,706, dated Jun. 17, 2016, 3 pages.
Examination Report for Indian Patent Application No. 5301/CHENP/2009, dated Jan. 19, 2017, 7 pages.
European Search Report for Application No. 11160161.3 dated Mar. 31, 2017, 4 pages.
European Examination Report for Application No. 11160161.3 dated Apr. 11, 2017, 6 pages.
European Examination Report for Application No. 11160161.3 dated Mar. 22, 2018, 6 pages.

* cited by examiner

Setting up an application system 200 based on scanning an area of skin 302 to determine attributes and applying RMAs 264 to that area of skin 302 in registers responsive to or in opposition to the determined attributes.
1000

Providing an application algorithm 230.
1010

Providing the application algorithm 230 on a computing environment 100.
1020

Providing storage 250 on the computing environment.
1030

Integrating a means of scanning 220 an area of skin 302.
1040

Integrating a means of application 240 of RMAs 264.
1050

FIG. 7

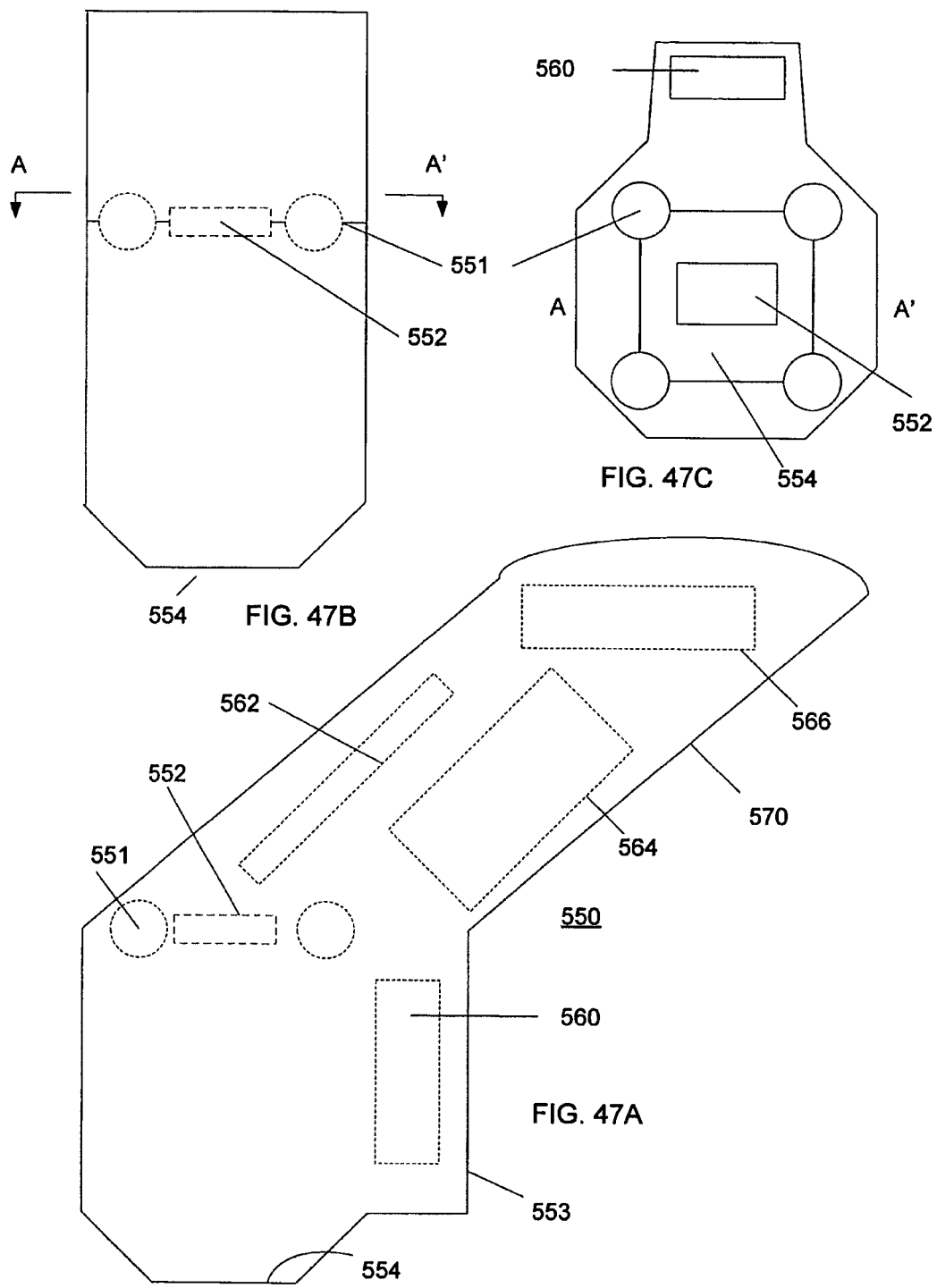

SYSTEM AND METHOD FOR APPLYING A REFLECTANCE MODIFYING AGENT TO IMPROVE THE VISUAL ATTRACTIVENESS OF HUMAN SKIN

CROSS-REFERENCE TO RELATED APPLICATIONS

This application is a continuation of U.S. application Ser. No. 14/571,815, filed on Dec. 16, 2014, which is a continuation of U.S. application Ser. No. 13/183,227, filed on Jul. 14, 2011, now U.S. Pat. No. 8,915,562, which is a continuation of U.S. patent application Ser. No. 11/503,806, filed on Aug. 14, 2006, now U.S. Pat. No. 8,007,062, which claims the benefit of U.S. Provisional Application No. 60/708,118 filed Aug. 12, 2005, the disclosure of which is expressly incorporated herein by reference in its entirety by applicants.

FIELD OF THE INVENTION

The current invention relates to automated computer-controlled methods to selectively and precisely apply one or more reflectance modifying agent, such as a dye or pigment, to human skin to improve its visual attractiveness.

BACKGROUND OF THE INVENTION

Prior Cosmetic Techniques and their Disadvantages

Prior art techniques for modifying the appearance of skin include natural tanning, artificial tanning, and the deliberate application of cosmetics. Each of these prior art techniques has limitations.

Typically, the applications of cosmetic substances to skin are largely manual, for example through the used of brushes, application tubes, pencils, pads, and fingers. The application methods makes prior art cosmetics imprecise, labor intensive, expensive, and sometimes harmful, when compared to the computerized techniques of the present invention.

Most prior art cosmetic approaches are based on the application of opaque substances. There is a need for the precise application of reflectance modifying agents (RMAs), such as transparent dyes, to provide a more effective modification of appearance.

Manual cosmetic applications are imprecise compared to computer-controlled techniques, and this imprecision may make them less effective. For example, the heavy application of a foundation base for makeup may cause an unattractive, caked-on appearance.

Manual techniques typically take a long time to employ, as can be seen in any morning commute on a highway, where people frantically take advantage of stops to finish applying their makeup.

Manually applied makeup is not cheap, and when the help of professionals such as beauticians is required, is even more expensive.

Often the materials applied to the skin in manual techniques are themselves potentially harmful. For example, a foundation base for makeup may cause skin to dry out and may inhibit the skin's breathing. Sunlight or artificial light used for tanning may cause cancer.

Therefore, there is a need for the precise application of reflectance modifying agents (RMAs) to provide a more effective, more automated, faster, less expensive, and less dangerous modification of the appearance of skin.

In this specification, the terms "reflectance modifying agent" or "RMA" refer to any compound useful for altering the reflectance of another material, and are explained in further detail below. Some examples of RMA are inks, dyes, pigments, bleaching agents, chemically altering agents, and other substances that can alter the reflectance of human skin and other features. The terms "dye" and "transparent dyes" are used for brevity in this specification to represent any RMA.

BRIEF SUMMARY OF THE INVENTION

These and other needs are addressed by the present invention. The following explanation describes the present invention by way of example and not by way of limitation.

It is an aspect of the present invention to provide a computer-controlled system and method for determining visual attributes of an area of skin, and then applying at least one reflectance modifying agent to the area of skin. In one embodiment, the reflectance modifying agent is applied in agreement with the visual attributes. In another embodiment, the reflectance modifying agent is applied in opposition to the visual attributes.

It is another aspect of the present invention to determine the visual attributes of an area of skin by electronically scanning the area and analyzing the scanned data in a computing environment.

In one embodiment, the scanning provides reflective data about the skin. The data is used to conduct feature identification and to evaluate potential corrective strategies to improve the visual appearance of the skin. An example of a corrective strategy is to deliberately alter the reflective properties of skin in order to compensate for the actual reflective properties of the skin. The application of one or more RMA changes the visual appearance of the skin.

In one embodiment, the scanning provides both reflective and surface profile data. The data is used to conduct feature identification and to evaluate potential corrective strategies to improve the visual appearance of the skin. An example of a corrective strategy is to deliberately alter the reflective properties of skin in order to compensate for both existing reflective properties and existing morphological properties.

It is another aspect of the present invention to create a map of the area of skin, and to use that map at a later time to determine the location, relative to the skin, of an RMA applicator such as an inkjet technology, for example an inkjet print head, and to supply instructions to the applicator. The map may also be used to compare images from a first time and a second time in order to detect changes in reflectance or shape.

In this patent specification, the phrase "inkjet technology" refers generally to "drop control" technology, whereby each individual droplet of the substance being applied can be controlled by the applicator, as known to those skilled in the art. A particularly useful technique for the present invention is to employ "drop on demand" technology, a subset of drop control technology. In this specification, the phrase "inkjet printer" is used for brevity represent any form of inkjet technology.

It is another aspect of the present invention to precisely apply a mixture of transparent dyes to human skin in response to the local reflective properties of the skin.

It is another aspect of the present invention to precisely apply a mixture of transparent dyes to human skin in response to the local reflective properties and local surface profile data of the skin.

These and other aspects, features, and advantages are achieved according to the system and method of the present invention. In accordance with the present invention, a computer-controlled system determines attributes of an area of human skin, and applies a reflectance modifying agent (RMA) at the pixel level, typically to make the skin appear more youthful and so more attractive. The system scans the skin, identifies attributes which may be enhanced or camouflaged, and applies the RMA, typically with an inkjet printer. The identified attributes may relate to reflectance and may refer to features such as irregular-looking light and dark spots, age-spots, scars, and bruises. Identified attributes may also relate to the surface topology of the skin, such as depth, for more precisely enhancing surface irregularities such as bumps and wrinkles. Feature mapping may be used, for example to make cheeks appear pinker and cheekbones more prominent. The RMA can be applied in agreement with identified patterns, such as adding red to a red area, or in opposition, such adding green or blue to a red area, according to idealized models of attractiveness.

It is an aspect of the current invention to collect and analyze data at different wavelengths (color) in order to provide a basis for detailed analysis of skin features. Some skin features may be identified from the characteristics that the features exhibit in different wavelengths.

As an example of one type of enhancement, a random freckle, such as from sun damage, on an older person can be made to appear more uniform, a characteristic of natural freckles in young skin, as illustrated in FIG. 22. When scanned data of the random freckle 440 is put into a spectral band, it shows a rough, irregular pattern. Based on empirical observation, a pattern for a natural freckle 442 on young skin has a much more regular and symmetrical pattern which makes the natural freckle 442 appear crisper. This natural pattern 442 may be used as an aim pattern 448 for comparison with the pattern for the random freckle 440. The random freckle 440 follows the general configuration of the aim pattern 448 but extends into higher light frequencies 446. By applying an RMA, such as a dye, to darken to lower frequencies of all the areas on the random freckle 440 that are in the higher frequencies 446, an enhancement 444 to the random freckle 440 can be achieved that more closely approximates the pattern of a natural freckle 422. Thus, by the application of an RMA in opposition to the scanned data about random freckles 440, the reflectance properties of the skin can be changed so that the skin appears to have crisper, more youthful-looking freckles, and so appears more attractive.

The application of RMAs at the pixel level allows much greater accuracy than with prior art methods, so that less of the applied material is used.

In one embodiment of the current invention, an application device comprising a scanner and an inkjet printer makes a single pass over an area of skin. It scans the skin, identifies unattractive characteristics, calculates enhancements to make the skin more attractive, and quickly applies RMAs onto the skin to achieve those enhancements. For example, it can give the skin a smoother appearance by identifying dark and light spots and applying an RMA to darken the light spots according to a predetermined averaging technique.

In a further embodiment of this concept, the application device makes multiple passes over the skin, each time improving the desired enhancement or enhancements.

In another embodiment, the application device makes a first map of the features of the skin and identifies unattractive features. It then calculates a second map to represent a desired appearance of the skin, and uses the difference between the actual and desired maps to generate a specific plan to apply RMAs to the skin in order to change the appearance of the skin to approach a desired appearance. Then it applies RMAs to achieve desired appearance. Again, multiple passes can improve the effectiveness of this method.

In one example, the first map is generated from the reflective properties of individual pixels in the map, and the specific plan includes a calculation of the precise amounts of each of a plurality of transparent dyes to be applied by an inkjet apparatus to the corresponding pixels on the face. In another example, the calculated amount of dye is a fraction of the total amount of dye required for a pixel, so that multiple passes over the same area can be made, with each pass adding more dye if necessary.

In this embodiment, a detailed scan is made of a region of human skin such as a face, leg, or arm. The scan is acquired by deliberately flashing multiple light sources arranged in a known configuration, and scanning a small area of skin as the light sources are turned on and off. By comparing readings from different light sources, both the reflectance and the surface profile of the skin can be determined.

The data from the scan includes reflective characteristics of the skin. These characteristics can be used to produce a detailed map of the skin which includes both reflectance and skin surface morphology. The detailed map can be used to develop a corrective plan to selectively apply a plurality of transparent dyes or other RMAs to the region of skin in multiple passes. In each pass, a fraction of the desired correction is made, so that errors in application are averaged over the multiple passes.

In further refinement of the mapping embodiment, the application device makes an advanced map of the features of the skin to identify large features such as a cheek and a cheekbone, and makes enhancements specific to them according to a library of idealized features. For example, it makes cheeks redder, so that they appear healthier, and darkens areas under cheekbones, so that they appear more prominent. Multiple passes can also improve the effectiveness of this method. This feature recognition can also be used in combination with either artificial intelligence or artistic control strategies.

In the various embodiments, the scanning of the skin, the calculations, and the application of RMAs to make enhancement to the skin can be very fast and precise.

BRIEF DESCRIPTION OF THE DRAWINGS

The following embodiment of the present invention is described by way of example only, with reference to the accompanying drawings, in which:

FIG. 7 is a flow chart that illustrates a process for setting up an application system;

FIG. 47A is a side view of one embodiment of a handheld device for skin marks.

FIG. 47B is a front view of the device of FIG. 47A.

FIG. 47C is a top cross sectional view along section AA' of FIG. 47B.

DETAILED DESCRIPTION OF EMBODIMENT

Applying Reflectance Modifying Agents to Improve the Visual Attractiveness of Human Skin The details of the following explanation are offered to illustrate the present invention clearly. However, it will be apparent to those skilled in the art that the concepts of present invention are not limited to these specific details. Commonly known elements are also shown in block diagrams for clarity, as examples and not as limitations of the present invention. Furthermore, the order of processes, their numbered sequences, and their labels are presented for clarity of illustration and not as limitations on the present invention.

Figure 24:
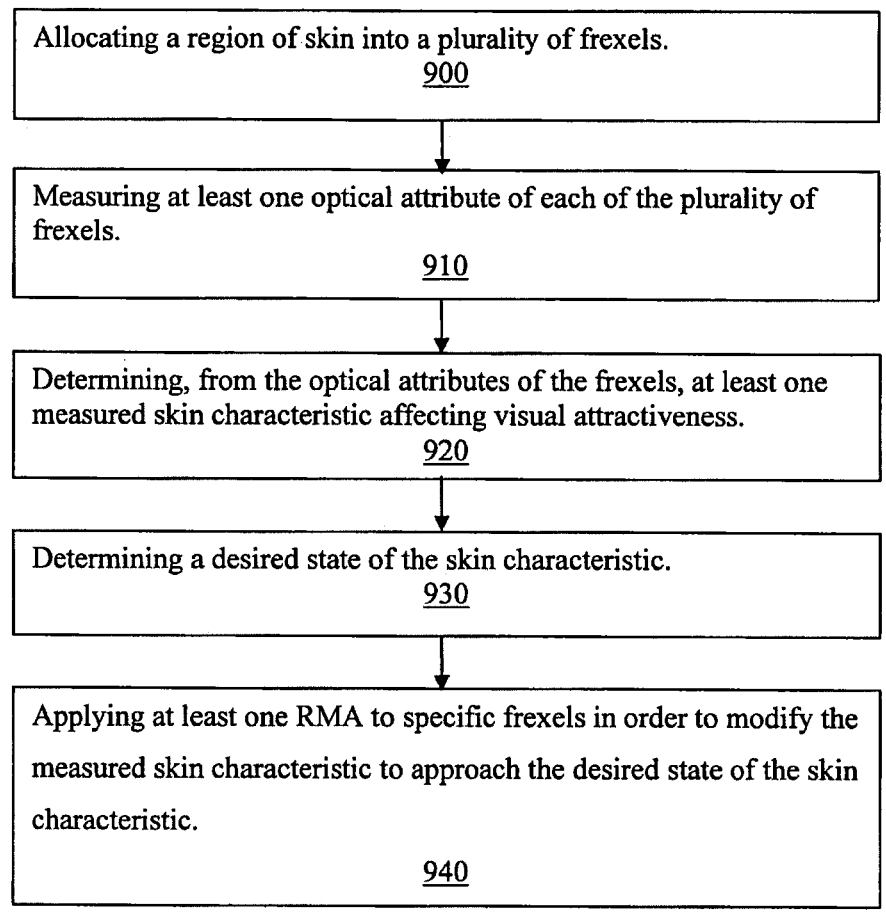
FIG. 24 is a flow chart showing the general steps employed by the present invention.

This embodiment describes a method to improve the visual attractiveness of a region human skin. As shown in FIG. 24, the method comprises the general steps of Step 900—allocating a region of skin into a plurality of frexels;

Step 910—measuring at least one optical attribute of each of the plurality of frexels;

Step 920—determining, from the optical attributes of the frexels, at least one measured skin characteristic affecting visual attractiveness;

Step 930—determining a desired state of the skin characteristic; and

Step 940—applying at least one reflectance modifying agent to specific frexels in order to modify the measured skin characteristic to approach the desired state of the skin characteristic.

Allocating a Region of Skin into a Plurality of Frexels

In this patent specification, the term "frexel" is defined as a small pixel-like region of the skin. In this patent application, the term "skin" is used not only to refer to skin as on the surface of the human body, but also to refer more broadly to any human feature that may be enhanced cosmetically, for example fingernails and hair. A frexel might correspond to a small portion of a freckle or other skin feature, or it may correspond to an area of the skin that does not have special features. A frexel thus refers to skin rather than to an independent coordinate system.

The term frexel is used to suggest that what is being measured is on a 3-D surface rather than a flat surface. A region of skin is comprised of a plurality of frexels. For instance, if a resolution of 300 dots per inch (11.8 pots per mm or "dpmm") is used, a frexel may have a width and height of about 1/300 of an inch (0.085 mm) so that there are approximately 90,000 frexels per square inch (140 frexels per square mm). The surface of the human body may have millions of frexels.

By allocating skin into frexels, the present invention can accomplish scanning and the application of RMAs for enhancement at the higher end of the human visual ability to resolve detail.

Figure 23:
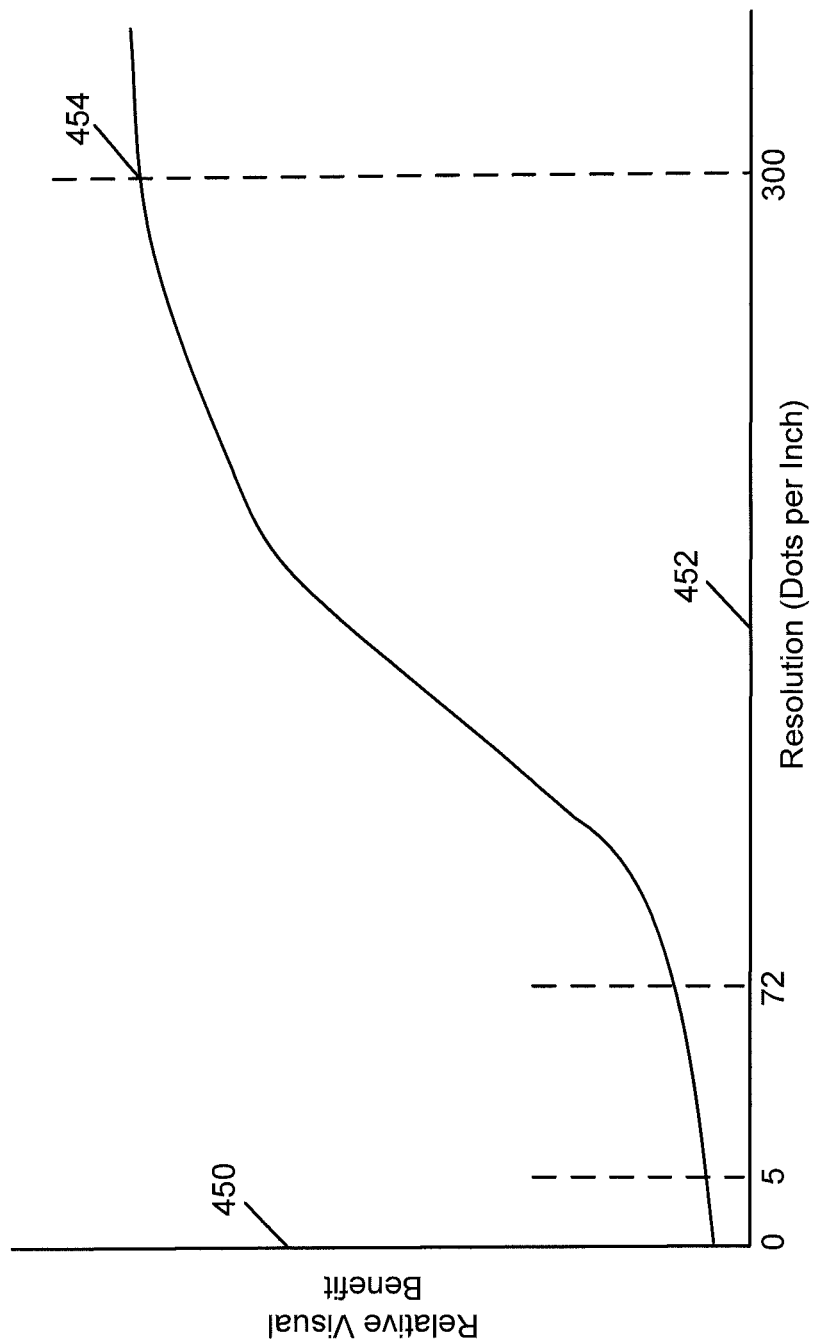
FIG. 23 is a generalized graph of visual benefits versus resolution.

FIG. 23 is a generalized graph of relative visual benefits 450 versus dots per inch (DPI) 452 resolution. For reference, a typical computer screen has a resolution of 72 dots per inch (dpi) (2.83 dpmm). The limit of human visual detection at a viewing distance of 10 inches (254 mm) is about 20 pixels per millimeter, or 500 dpi under idealized conditions of 100% modulation (alternating black and white lines) and good lighting conditions. An inkjet printer has a typical resolution of about 720 dpi (28.2 dpmm) with the ability to form single color dots at a resolution of 1440 dpi (56.7 dpmm). (Several dots are required to form a non-primary color.) A resolution of about 300 dpi (11.8 dpmm) 454 is considered to be an upper end of desired resolution under normal circumstances, because improved resolution is not generally detectable. For example, magazines typically require a photographic resolution of 300 dpi (11.8 dpmm) but are printed at 150 dpi (5.9 dpmm). By contrast, standard cosmetic resolution is approximately 5-20 dpi (0.2-0.8 dpmm) for careful manual application. A target resolution in the range of 50 to 300 dpi (2-11.8 dpmm) provides much better resolution that existing cosmetic techniques, as well as advantages in making the adjustments in response to actual and desired skin characteristics; and the further advantage of automatic application. Prior art techniques for applying makeup with brushes, tubes, and fingers have much coarser resolutions. For instance a fine brush has an approximate resolution of about 20 dpi (0.8 dpmm).

Figure 1:
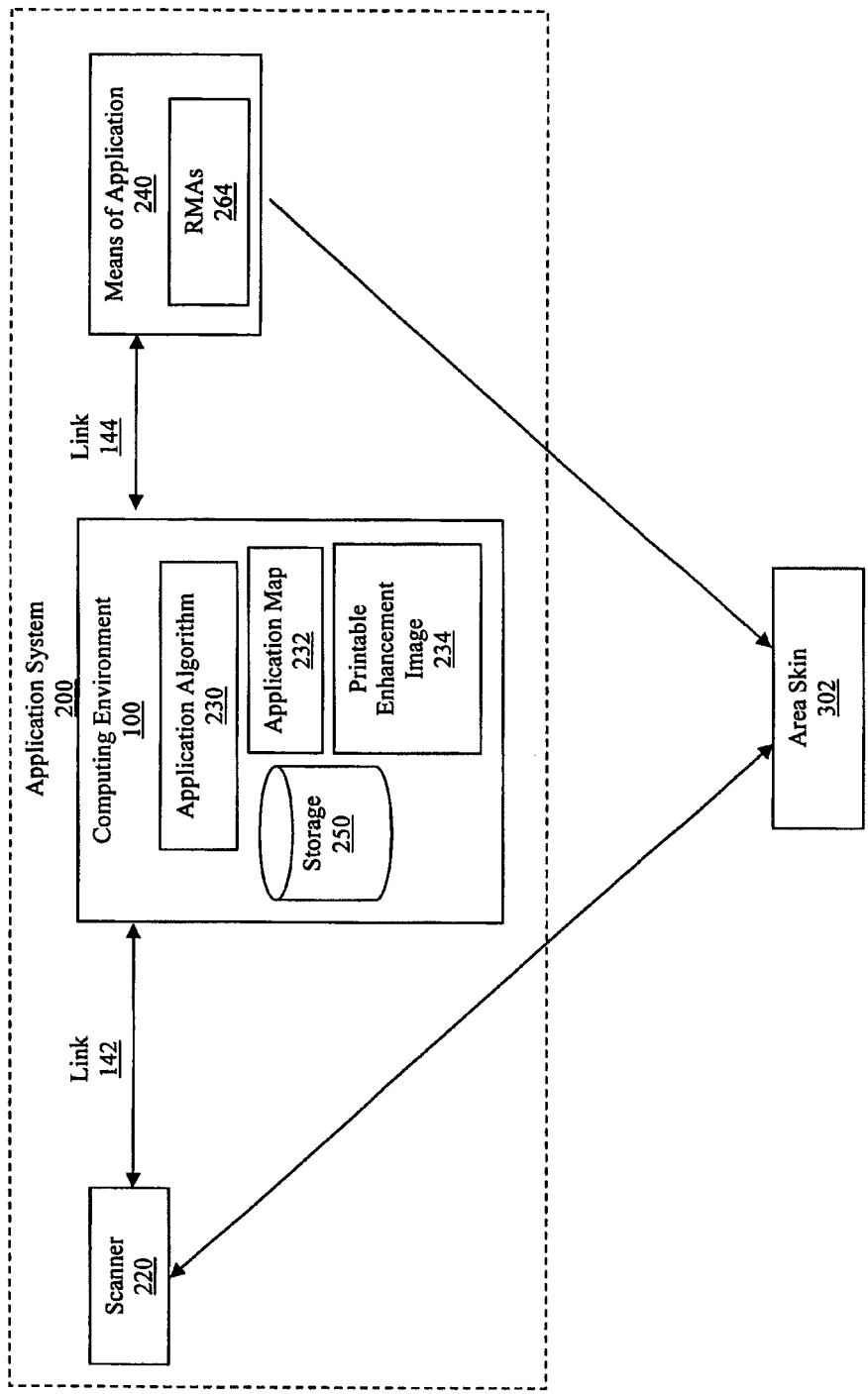
FIG. 1 is a block diagram showing an operating environment in which embodiments of the present invention may be employed for applying RMAs onto skin.

Measuring at Least One Optical Attribute of Each of the Plurality of Frexels Scanning As shown in FIG. 1, in one embodiment, an application device comprising a scanner 220 is moved across the area of skin 302 so that the scanner 220 can electronically record data about one optical attribute, such as the reflectance, of each of the plurality of frexels. For example, the area of skin 302 might be a face.

The scanning may acquire images under various frequencies to obtain useful data. For example, it may obtain data on reflectance in a particular color, for example red, to help determine a particular characteristic of skin for enhancement. The scanning may also provide data for determining other characteristics of skin, such as surface topology, based on reflectance angle from multiple light sources.

In an embodiment a two-dimensional array is used for the scanning. In other embodiments, a line array may be used.

Alerting Sounds

In an embodiment one or more alerting means, such as a sound, light, or vibration may be used to indicate when sufficient scanning has been accomplished. The alerting means may comprise a sound indicator including volume and tone modifications to a white noise used as indicators for progress, degrees of completion, and error conditions while applying the RMA.

Examples of a white-noise-like signal modified in volume and tone include shaving with an electric shaver, in which the sound changes where the beard is harvested to indicate and guide completion of shaving, areas that need completion, and optimum direction of application.

Another example is in sawing wood, where a carpenter uses sound to guide the speed of sawing and to indicate problems. Many other examples of a white-noise-like indicating signal can be found.

Other audible indicators are possible, including voice, tones, etc. The white noise indicators in some situations are the most intuitive, because they are ubiquitous in nature. Tactile feedback, such as vibration, may also be included as part of the sound.

Sensors

In one embodiment, the scanner 220 comprises a sensor and four LED light sources arranged in a known configuration within a housing. The LED light sources are typically each turned on and off in a manner that allows the sensing of at least one optical characteristic for each light source. In one example, 120 captures may be made per second, 30 from each light, quickly providing a large about of data about the skin. That data can then be used to determine both reflectance characteristics at various wavelengths, and the skin's surface profile. In an embodiment the captured images may be averaged for effectiveness.

In an embodiment, the sensor comprises shading patterns on the LEDs useful for determining the relative position of the sensor.

In an embodiment a monochrome sensor with a Bayer array may be employed. Other arrangements of LEDs and sensors may be used.

Analyzing the Scanned Data

The scanned data comprises information about

The reflectance from the skin, and

The location of the skin relative to the sensor, and the skin features.

In an embodiment, the application algorithm 230 puts the stored data into spatial frequency bands and uses pattern recognition to analyze them to determine the landscape of the area of skin 302 and the dimensions that require application of the RMAs 264. The process used to determine these dimensions will be explained in detail below.

The application algorithm 230 uses its analysis to create in software an application map 232 of the area of skin 302, which is stored in storage 250, for potential future use.

Optical Attributes

The reflectance, which is a measure of the reflection of the skin, is independent of its illuminance. Illuminance is a measure of how much light gets to the skin. The light reading is independent of the surface topology reading.

In an embodiment, certain optical attributes, such as the amount of reflectance of each frexel, may be determined directly from the scanned data. In another embodiment, the scanned data is translated into at least one spatial frequency band for analysis. In still another embodiment, the scanned date may be translated into multiple spatial frequency bands, such as red, green, and blue (RGB) bands.

Figure 14:
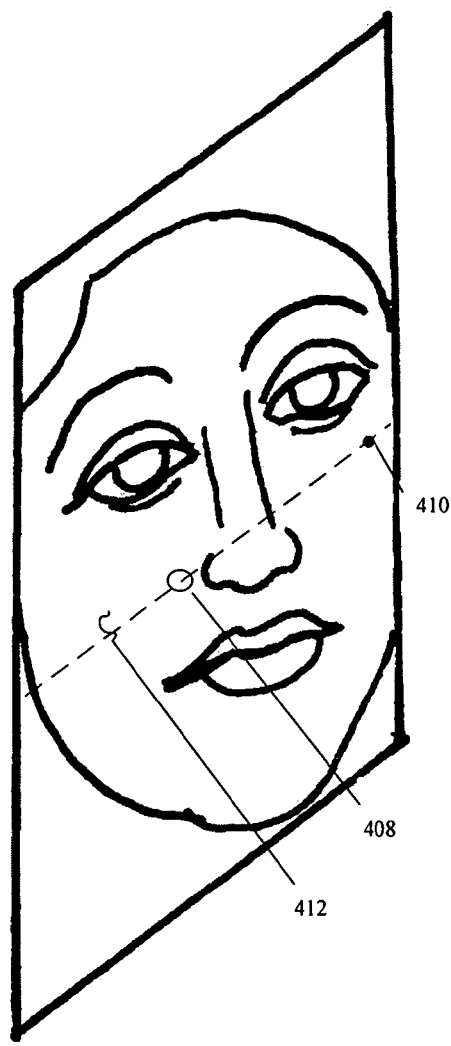
FIG. 14 is a perspective diagram that illustrates features on a 2-D map of a human face.

FIGS. 16A-E represent the patterns of a 2-D face 232, shown in FIG. 14, after the data has been put into single spatial frequency bands to determine the attributes of albedo 348 and illuminance 352.

Albedo

Albedo is the percentage of reflectivity of incident light from the surface of an object. In the case of electronic scanning, the albedo is the RBG values of the scanned area of skin. In this patent application, the term "actual albedo" means the observed albedo before correction and the term "aim albedo" refers to the desired reflectivity of an area of skin in order to improve the appearance of that area of skin. In one example, the aim albedo is determined from one or more correction strategies, including general smoothing, specific feature enhancement, and artistic strategies.

Figure 16:
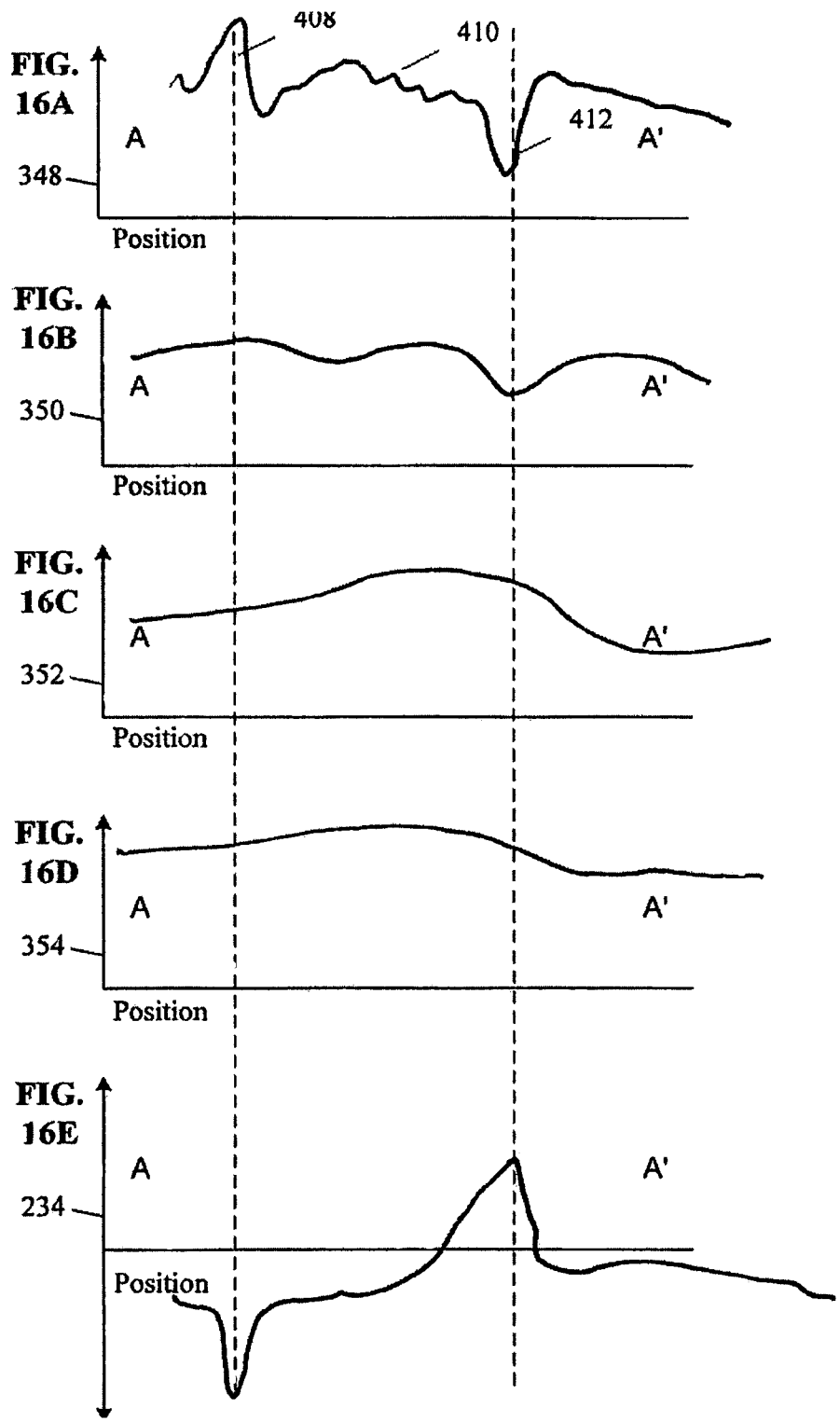
FIGS. 16A-E are charts of the reflectance, illuminance, and a printable enhancement image along line A-A' of the 2-D map of the human face of FIG. 14.

The top band in FIG. 16 represents the actual "albedo" along line A-A' in the 2-D surface map 232 of FIG. 14. A rise in the actual albedo graph identifies the light spot 408. A deep, sharp drop in the graph identifies a non-uniformity 412 such as a scar. And an irregular section identifies a freckle 410.

Illuminance

Illuminance is the incident light reaching a unit area of the surface of an object, and is a function of the angle of the incident light relative to the surface.

The spatial frequency bands also graph the actual illuminance or shading 352, shown in FIG. 16, of the 2-D surface map 232 shown in FIG. 14.

Reflectance and Illuminance Data and Calculations

In one example, frexel data obtained from scanning a region of skin may be represented as $[(x_s, y_s, z_s, \alpha_s, \beta_s, \gamma_s),$
$(x_f, y_f, z_f, \alpha_f, \beta_f, \gamma_f),$
$\{(refl)_A, (refl)_N, (refl)_S, (refl)_E, (refl)_W\}]$, The term $\{(refl)_A, (refl)_N, (refl)_S, (refl)_E, (refl)_W\}$ represents reflective data for the frexel i under ambient lighting conditions, and for each of four light sources, such as LEDs, which are arbitrarily designated as north-south-east-west for ease of discussion. Other numbers of light sources, such as three sources, can be used, but the mathematics is simplified with four light sources. The (refl) represents one or more data point for the reflectance measurement. The reflectance measurement for a wavelength is the product of a constant, the illuminance, and the albedo for the wavelength:

Reflectance=$k$*illuminance*albedo

For instance:

Reflectance(red)=$k$(red)*illuminance(red)*albedo(red)

The constant depends upon several factors including the speed of the lens, the sensitivity of the camera or sensor, the transmission characteristics of the color filter, the gain of the analog amplifier, the digital gain applied by the software, and other factors. The constant k will usually be measured and corrected for as a correction constant or calibration of the camera corrects for these effects. The value of the constant can typically be determined during calibration, when the illumination from the LEDs is assumed to be fixed, and the albedo is calculated based on that assumption.

Reflectance is not absolute, but is a measure of what comes out of the camera.

The sensor is typically a camera without an amplifier, a digital converter, or the lens housing.

In one embodiment, the sensor is a solid state MOS sensor with a lens and associated electronic equipment.

The frexel data can be processed to determine a reflectance and an illuminance for each light source, and that information can be used to determine reflectance and surface profile.

In one example, the reflectance is the average or mean of all measurements. The illuminance can be determined from the known brightness of light sources such as LEDs. Illuminance is the known light times the cosine of the angle of incident light relative to the normal.

One problem with obtaining reflectance data is that glare may be present at some angles, and that an accurate reading cannot be obtained. In one example, glare or glossiness can be eliminated with the use of polarizing materials to provide a cross polarization of the LEDs. In other examples the sensor can deliberately be positioned at a relatively large angle such as 60 degrees in order to eliminate glare.

Determining Position

Frexel Location Relative to Sensor or Coordinate System

The term $(x_f, y_f, z_f, \alpha_f, \beta_f, \gamma_f)$ may represent the distance of the frexel i from the sensor, or may be an absolute position and orientation of the frexel with respect to a reference coordinate system. In one example, the determination of the distance from the frexel to the scanner may be made in two steps. A first step can be an approximate mechanically-based measurement such as a constant height of the sensor from the skin. The second step can be an optical first derivative measurement to provide a fine adjustment. In one example, the fine adjustment is calculated by measuring an angle from the surface. In another embodiment, a fine adjustment may be made by using two light sources to send out two reference points or grids for detection by a sensor.

Mechanical Gross Estimate

In one embodiment, the sensor may be attached to a helmet or a fixed booth in a manner that the sensor position may be determined relative to the helmet or booth.

Figure 26:
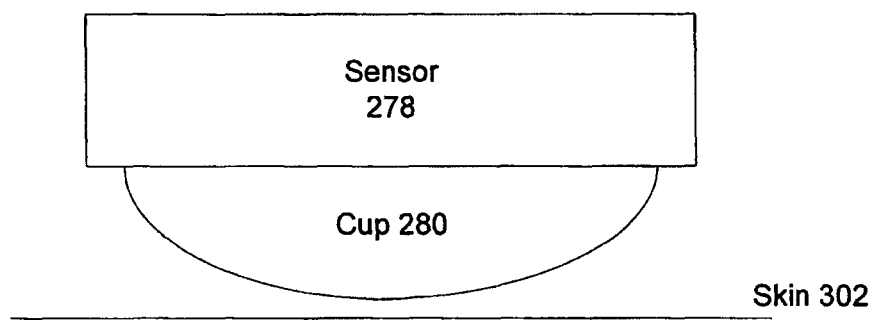
FIG. 26 is a block diagram showing a spacer cup on a sensor.

In another embodiment shown in FIG. 26, the sensor 278 may be equipped with a cup 280, so that the sensor 278 maintains an average height from the skin.

In another embodiment, the sensor may start from a known position, and keep track of its movements in order to estimate its location. The sensor may measure the angle relative to the probe itself to determine the shape of a surface feature relative to constantly changing plane of probe.

A gimbal may be used to provide a reference in space. The tracking may be used to follow the position of a hand, or hand-held scanner in space. The gimbal arrangement can provide regular feedback in a manner that is analogous to stereo-mapping or GPS mapping relative to satellites, such as for crop dusting.

Optical Fine Adjustment

For finer alignment, an optical means may be used. For example, the first derivative of the z component of the skin may be obtained from shading, through multiple light and shadings from probes. The first derivative can provide a measure of the angle of the surface.

In one example, three light sources send out different patterns. The color and the shading provide data for determining surface relief so that a shaded relief map may be obtained from the LEDs.

Frexel Orientation

By determining the tilt of the frexel relative to two orthogonal axes, the orientation of the frexel can be determined. The orientation of a frexel and its neighbors is an indication of the actual local surface texture of the skin. One aspect of the current invention is the ability to measure and compensate for both local reflective properties and local surface texture.

In this example, there are four light sources which are designated as North, South, East, and West. The sensor obtains data when each light source is on, and the other sources are off. The sensor may also obtain data for ambient lighting, with none of the four light sources on.

The tilt of the frexel can be determined by comparing the North and South measurements. The difference between these measurements is a related to the tilt of the frexel along the East-West axis. The difference between the East and West measurements is a related to the tilt of the frexel along the North-South axis.

It is generally necessary to make a gamma correction by converting the data to linear space. The gamma correction is approximated by taking the square root of the data output by typical gamma 2 cameras.

Light Sources

Figure 40A:
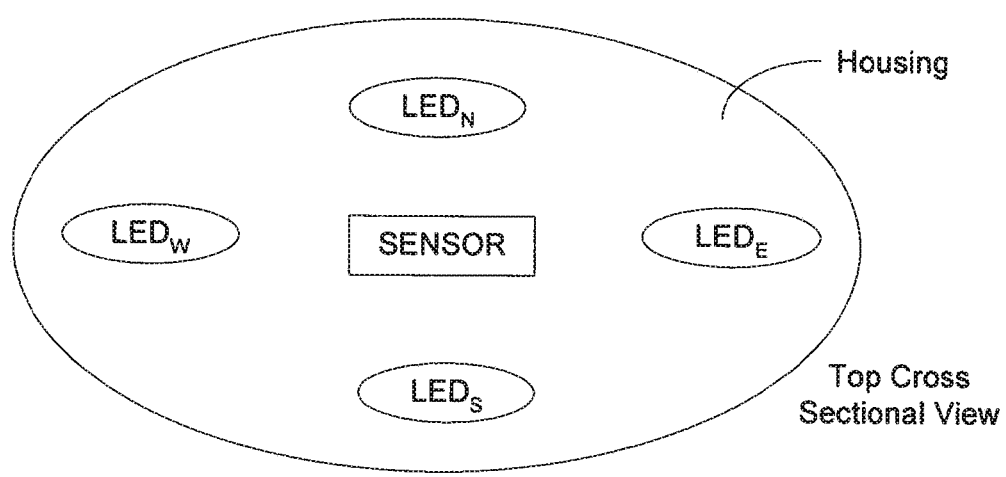
FIGS. 40A-B are sample layouts for LEDs and a sensors for acquiring reflectance and skin orientation data.
Figure 40B:
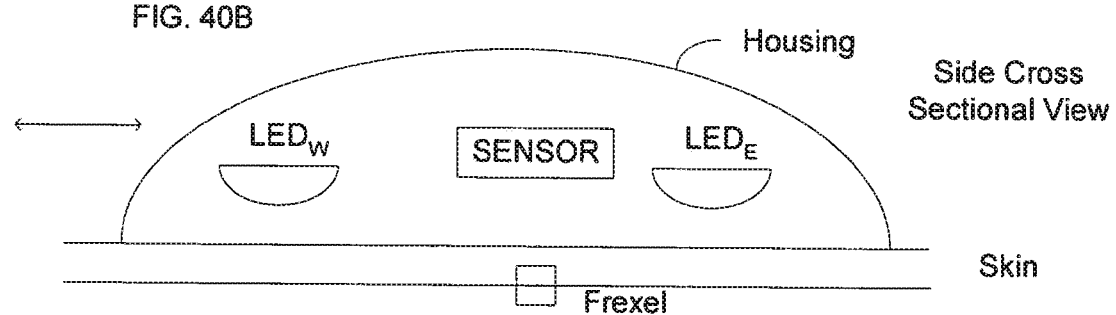

FIGS. 40A-B show configurations for light sources that may be used with one embodiment of the present invention. In this embodiment, a set of four light sources is used—$LED_N$, $LED_S$, $LED_E$, and $LED_W$. The light sources are placed in a diamond configuration where the sensor is positioned at the center of the LED layout. This configuration simplifies the mathematical analysis for calculating surface profile.

Mean Illumination

In one embodiment, it is useful to employ the concept of mean illumination. Mean illumination is the average angle and diffusion of light reaching a particular surface. This defines how surface irregularities are typically shaded. For example, mean illumination for the entire body is overhead, and a typical orientation for a head is vertical; therefore, a bump on a cheek is typically shaded at the bottom. For a child on the beach, typically the bump would be less tanned on the bottom because the average light throughout the day, integrating both sun angle and body angle to give average or mean illumination, is from over "head." Occasionally light is reversed from average. An example is lighting a face from underneath. However, this often gives a bizarre, sometimes sinister look, and is the exception that proves the rule. By correcting a defect for mean illumination, the best correction on average is performed.

Mean illumination is the interaction of mean light direction relative to gravity and the mean orientation of a particular frexel of skin relative to gravity. One method to obtain the angle of the skin is to use multiple diffuse or orthogonal light sources in a configuration which may include mirrors. The lights may be flashed repeated, as strobe lights, so that hundreds of images may be taken of a small area, and the data can be averaged. From the angle of the skin relative to "up," one can calculate how much light reaches the skin under mean illumination and the angle of the skin relative to "up."

A reasonable approximation to mean illumination can be made by turning on all lights sources at the same time, or by adding images made by individual light sources. In one example, mean illumination is diffuse because lights and probes are perpendicular to the skin.

A refinement of this technique will compensate for gloss effects on the skin. For example, several images with four lights sources may be used and an average taken of the images from the light sources. For example, the average might be a median. One advantage of the median is that if specular reflection is caught by a minority of light sources, it would be filtered by median. The median would also filter shadows observed from a minority of light source images. This is important because the human body represents complex surfaces, i.e. a nose may be shiny when illuminated.

One way to create diffuse light is to introduce light from many light sources at many angles. For example, a first light source can be oriented at a first angle with respect to the housing, and a second light source oriented at a second angle with respect to the housing. Another way to create diffuse light is to reflect it from the scanner housing. Another option is to polarize the light.

Example of Frexel Data Representation

An example of the data representation for a frexel is shown below:

[$(x_s, y_s, z_s, \alpha_s, \beta_s, \gamma_s)$,
$(x_f, y_f, z_f, \alpha_f, \beta_f, \gamma_f)$,
$\{(refl)_A, (refl)_N, (refl)_S, (refl)_E, (refl)_W\}$]

In this example, $(x_s, y_s, z_s, \alpha_s, \beta_s, \gamma_s)$ and $(x_f, y_f, z_f, \alpha_f, \beta_f, \gamma_f)$ represent the position and angular orientation of the scanner sensor and the frexel relative to a coordinate system.

Compression

In some embodiments, the efficiency of the data processing can be improved by various compression methods, such as JPEG.

Frexel Location on the Skin

Through Feature Mapping

Computer mapping for feature recognition, known to those skilled in the art in areas such as computer gaming, can be used for tracking the location of the probe on the area of skin 302 and for determining enhancements appropriate for specific features.

For example, such computer mapping enables the identification of features such as a cheekbone, a nose, and an ear, so that the probe can orient its location with regard to a particular frexel, potentially in multiple passes over an area of skin.

Moreover, the identification of a feature such as a cheekbone enables determination of appropriate enhancements. For example, a red reflectance modifying agent may be applied to the center of a cheekbone to add color to a face. Dark reflectance modifying agents may be applied underneath the cheekbone to make the cheekbone appear to project more prominently.

Skeleton Model

In one embodiment, a map is built around a skeleton model so that the skeletal joints become reference points. In this example, the joints are located, a stick figure is constructed, and a 3-D mesh is built around the stick figure. The map is relative to a predetermined model of human skeletal structure in the memory of a computing environment.

Manikin-Like Model

In one embodiment, the map is relative to a predetermined model of a human body.

Dynamic Model

In one embodiment, the map is relative to the movement of skin over a predetermined model, such as a skeleton model or manikin-like model.

Through Chemical Markers

In other embodiments, chemical markers may be applied to the area of skin during the scan to help create the map and enable subsequent tracking of the map with the area of skin 302. For example, ultraviolet markers may be used, such as dots which are visible under ultraviolet light, but not visible under conventional lighting.

Single Pass or Multiple Pass

In various embodiments, the scanning and correction can be accomplished in a single or multiple passes. For instance, a first pass may be performed to become acquainted with the subject, and a second or subsequent pass may be performed to get additional data. Multiple passes at different orientations over the same area provide an opportunity for compensating for the effects of skin hair by observing the skin at different angles.

Single Pass

In one embodiment of the current invention, an application device comprising a scanner and an inkjet printer makes a single pass over an area of skin. It scans the skin, identifies unattractive characteristics, calculates enhancements to make the skin more attractive, and quickly applies RMAs onto the skin to achieve those enhancements.

Multiple Pass

In a further embodiment, the application device makes multiple passes over the skin, each time improving the scanning and the application of RMAs for the desired enhancement or enhancements.

Example of Tracking Process

In one example of a tracking process, a rough position is first determined, and then a more precise location is established. In a first approach, a rough estimate of location can be maintained from a known starting point through the use of gimbals in proximity to the probe to compute distance and direction traveled. In another approach, a rough location can be determined from mechanical probes or gauges. In another approach, a rough location can be estimated mathematically by using the first derivative of the shading data.

Once the rough location is known, a more precise location can be determined from the analysis of frexel orientation from shading data. This is analogous to a pilot determining position by first knowing an approximate location and then locating land features that provide a more precise location.

Tracking Over Time

One advantage to the generation of maps is that changes in reflectance or surface profile can be determined by comparing an image from a first time with an image from a second time. These changes may represent changes in the health of a person, or may represent areas that require a "touch-up" of RMAs.

Determining, from the Optical Attributes of the Frexels, at Least One Measured Skin Characteristic Affecting Visual Attractiveness Pattern recognition may be used to identify features of the area of skin 302 that has been scanned.

Feature Identification

Reflectance and Topology

Feature identification may be based on patterns determined in scanned data, and may have to do with both the reflectance patterns and the surface topology of the area of skin.

Mathematical pattern analysis of this data allows identification of specific unattractive features that could benefit from enhancement techniques. As explained below, such features may typically be characterized by age-related and damage-related patterns that are irregular or asymmetrical compared to the more regular and symmetrical genetic-based patterns of younger skin.

The Eye's Perception of Depth

Figure 45:
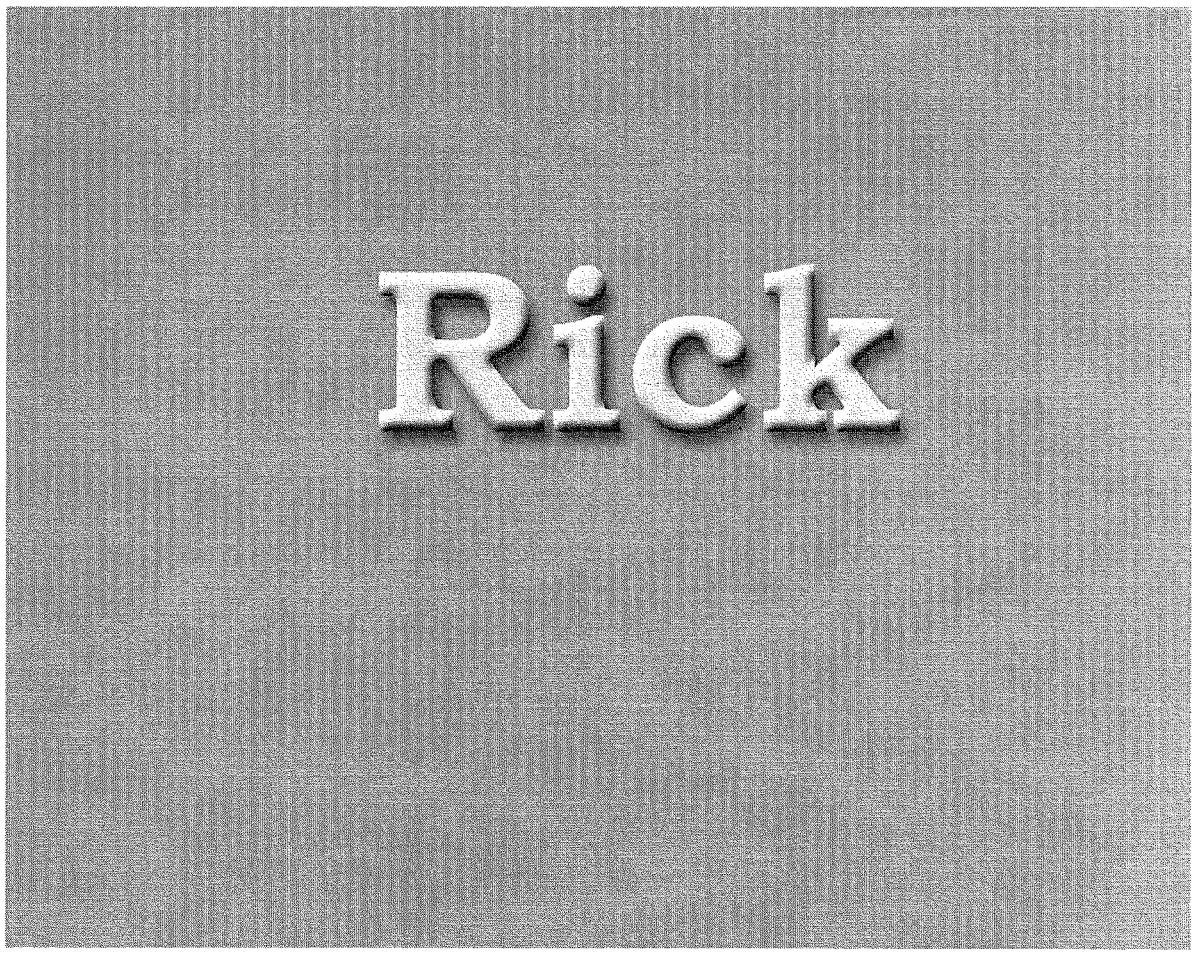
FIG. 45 is an example of a text image showing apparent depth.

At small distances, the human eye perceives depth by stereoscopy. At a typical human interaction range of a few feet, however, the eye perceives depth of human skin based on the reflectance of the skin. A difference in shading between adjacent areas of skin is perceived as a surface texture representing elevation or depth from the surface of the skin. As an example of that perception, FIG. 45 shows the text letters "RICK" which were created in Photoshop™ From an original image of flat letters, the software created the apparent shadows. The human eye interprets the differences in reflectance by assuming that a light source is located in the upper left, and that shadows are created because the text has a raised profile.

This perception of depth from differences in reflectance is also important in the perception of human beauty. The eye interprets differences in shading of skin to be surface texture. That perception of texture can be altered by changing the reflectance of the skin. In the letter example for instance, the perception of raised letters can be dramatically altered by reducing the shadowing around the letters.

The eye perceives the color of the skin and translates that color information into a perception of depth. One aspect of the current invention is to selectively change the reflectance of a portion of the skin in order to alter this perception of depth. This alteration may be made in relatively small areas such as a bump on the skin; or the alteration may be made over larger areas, such as with traditional cosmetics, such as deliberately darkening an area around the eyes or cheeks.

Examples of Unattractive Features

Some examples of unattractive features in skin that can be identified from scanned data are Acne,
Age spots/sun damage,
Bruises,
Bumps,
Cellulite,
Light spots,
Pitting,
Scars,
Damaged freckles, and
Wrinkles.

Other unattractive features that also may be identified have to do with artificial patterns that have been added to the skin, such as body painting and tattoos that have faded over time or that have been distorted by changing patterns of the skin itself such as sagging or wrinkling. These features can be identified and then refreshed through the application of RMAs to refresh or enhance their appearance.

Techniques for Identifying Unattractive Features

Pattern for Age-Related Freckles in a Single Spectral Band

Figure 22A:
FIG. 22A-C are diagrams that illustrate the effects of RMAs applied to improve the appearance of an age-related freckle.
Figure 22B:
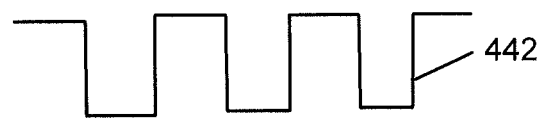

For example, natural freckles are about 2 mm across and are sharp edged and have the pattern 442 shown in FIG. 22B. Age-related freckles, caused for example by sun damage, have the pattern 446, shown in FIG. 22A.

Figure 22C:

As explained above, an age-related, random freckle 440, for example from sun damage, on an older person can be identified by its characteristic pattern in a single spectral band, as illustrated in FIG. 22. When scanned data of the random freckle 440 is put into a spectral band, it shows a rough, irregular pattern.

Patterns in Multiple Spectral Bands

Figure 25:
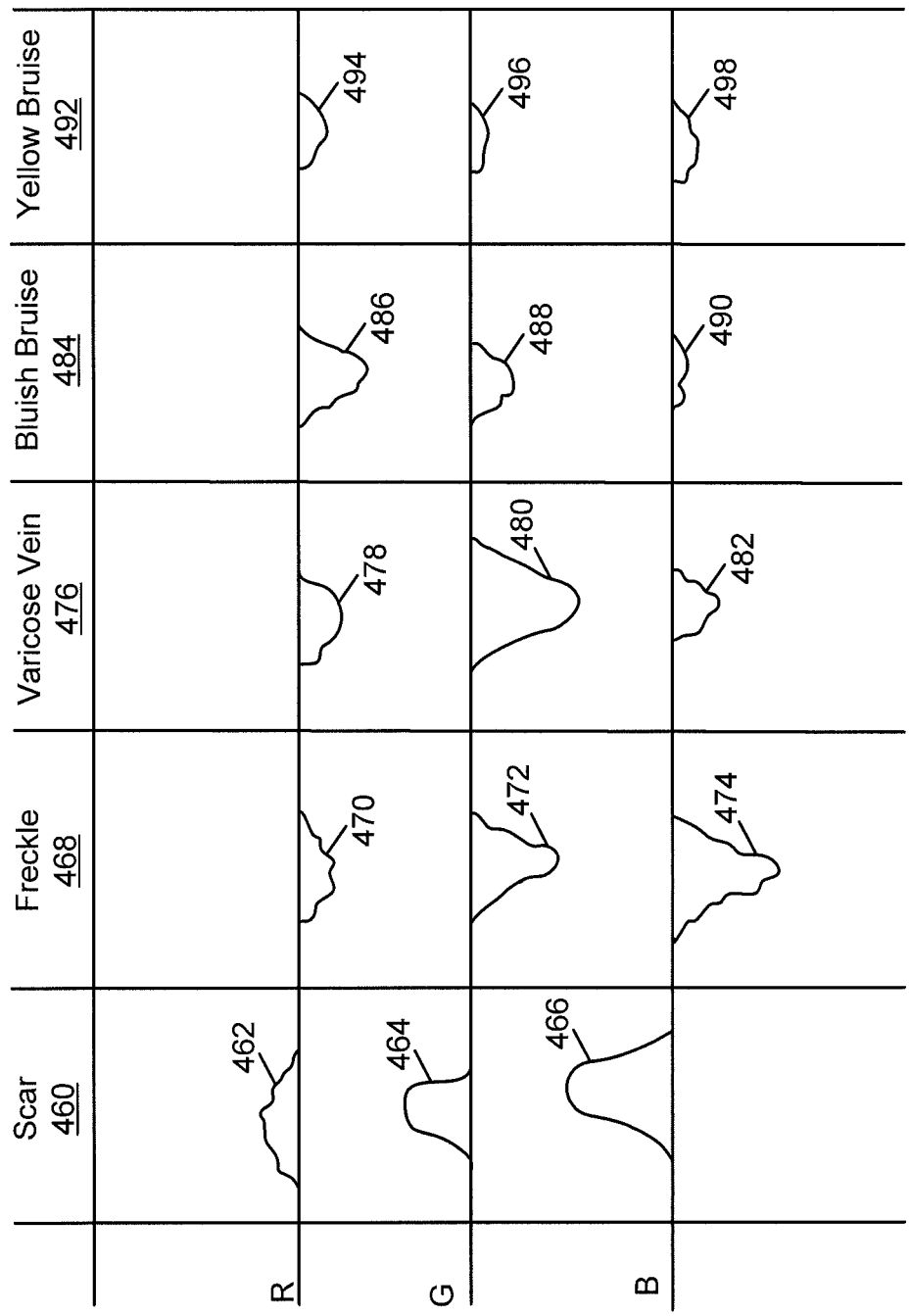
FIG. 25 is a generalized graph of patterns of unattractive features in RGB bands.

By breaking the scanned image into multiple spectral bands, such as RGB bands, the patterns of unattractive features may be identified with even greater clarity. For example, FIG. 25 is a generalized graph of patterns of unattractive features in RGB bands for an area of young skin, showing the empirically observed general patterns of A scar 460,
A freckle 468 from sun damage,
A varicose vein 476,
A new, bluish bruise 484, and
An older, yellow bruise 492.

The set of RGB patterns for each of these unattractive features is quite distinct and thus detectable through feature recognition. For example, the scar 460 shows patterns in the higher frequency range in all three bands 462, 464, and 466, unlike the other features. The freckle 468 dips more deeply into low frequencies in the blue band 474, than the blue-band patterns for the varicose vein 482, the bluish bruise 490, and the yellow bruise 498. The bluish bruise 484 has larger dips in the red pattern 486 and green pattern 488 than the yellow bruise red pattern 494 and green pattern 496. The yellow bruise blue pattern 498 dips more deeply than the bluish bruise blue pattern 490.

Advanced Feature Identification Through Mapping

Mapping based on feature identification can add greatly increased capabilities for enhancement to mapping based on reflectance and surface topology.

Maintain register over entire skin surface.

Translate 3-D to lightness/darkness using mean illumination, and include with lightness/darkness attribute, both for printing against or for aesthetic augmentation.

For example, feature identification can be used to identify large features such as cheekbones, noses, chins, lips, and eyes. This allows enhancements based on a library of idealized features, to create the following appearance:

Pinker cheeks

Note that red on white is not attractive, but a random pattern of red over a large white area can be: for example in pink cheeks.

A nose that is less red,

More prominent cheekbones,

Redder lips,

Eye shadow effects on eyelids,

Eyeliner,

A sharper jaw line,

Darker eyebrows,

Rounded eyebrows,

Deeper dimples,

More prominent breasts.

Means of Compensating for Special Conditions

Compensating for Body Hair

In one embodiment, the presence of skin hair may be compensated for by taking images in multiple passes while attempting to orient the hair in various directions. The orientation may be accomplished by a comb device associated with the scanner. In other embodiments, a static electric charge may be used to cause the hair to rise relative to the skin.

Determining a Desired State of the Skin Characteristic

Principles of Attractiveness

Figure 11:
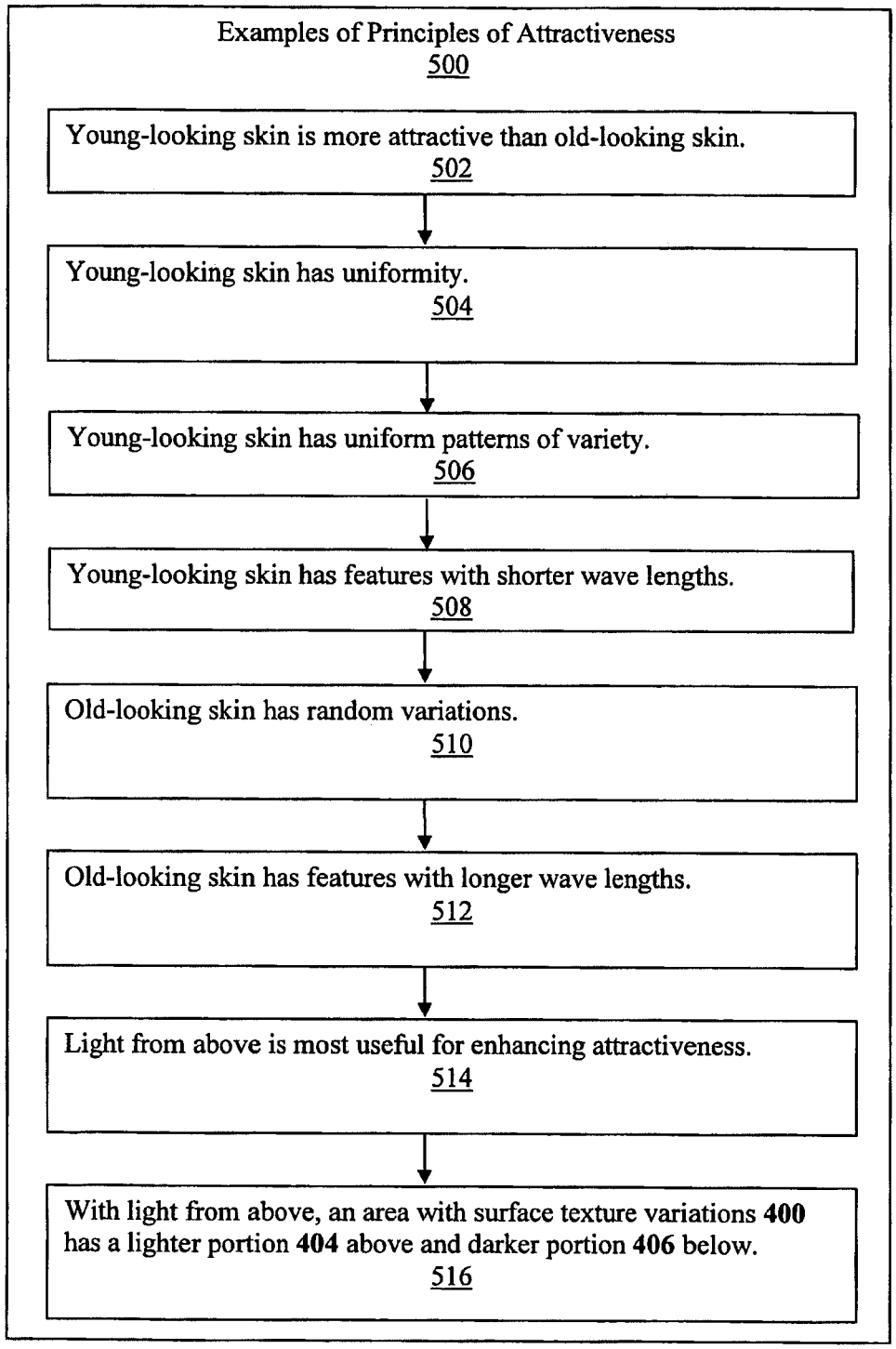
FIG. 11 is a flow chart that illustrates a process defining principles of attractiveness.

The present invention employs general principles of attractiveness 500, examples of which are shown in FIG. 11. These principles are based on observation of attributes that many people find attractive and thus represent tendencies in human behavior.

Observation 502—Young-looking skin is more attractive than old-looking skin.

One attribute of attractiveness is sexual attractiveness.

Observation 504—Young-looking skin has uniformity.

Young-looking skin has attributes that are more uniform and repeatable than the attributes of old-looking, because young-looking skin is closer to the genetic code. This point is in keeping with a general principle that symmetry in human features tends to be more attractive to the human eye than asymmetry. For example, tanning is attractive not because it darkens the skin, but because it levels out the spatial frequencies, making the skin more uniform.

Observation 506—Young-looking skin has uniform patterns of variety. Some variety in the appearance of skin can be attractive, for example genetic-looking freckles in young-looking skin. The variety in young-looking skin is more regular in its patterns of spatial frequency than the variety in old-looking skin. For example, genetic freckles are more regular in their patterns of spatial frequency than marks caused by age, sun damage, etc., which are more random.

Observation 508—Young-looking skin has features with shorter wave length light frequencies than those of old-looking skin.

Observation 510—Old-looking skin has random variations.

Observation 512—Old-looking skin has features with longer wave lengths.

Old-looking skin tends to have features with longer wave lengths, representing random effects such as age spots, wrinkles, and scars.

Observation 514—Light from above is most useful for enhancing attractiveness.

Average lighting, defined as light from above, is most useful for enhancing attractiveness in human skin because it is what the eye is used to.

Figure 12:
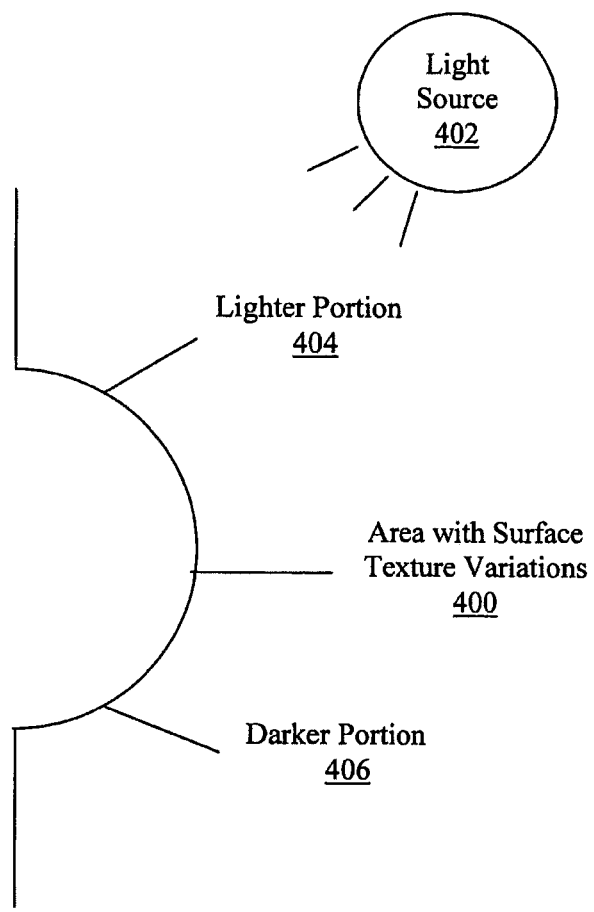
FIG. 12 is a block diagram that illustrates lighting from above on an area with surface texture variations.

Observation 516—With light from above, as shown in FIG. 12, an area with surface texture variations 400 has a lighter portion 404 above and darker portion 406 below. When the dominant light source 402 is from above, an area with surface texture variations 400, such as a bump, scar, or wrinkle, has a lighter portion 404 above and darker portion 406 below. An area with surface texture variations 400 can thus be identified by this pattern.

General Techniques of Enhancement

The current invention addresses several factors in the human perception of beauty or attractiveness, based on the principles of attractiveness.

Smoothness

In one embodiment, the reflectivity of the skin is modified to compensate for the skin's shadows when illuminated by normally average light. This softens or eliminates the perception of skin roughness. The effect is similar to that achieved in tanning.

Uniformity of Features

In one embodiment, a dye is deliberately added to portions of a skin area in order to make the features appear more uniform. For example, freckles can be made to look sharper and more uniform so that they have the appearance of uniform youthful freckles rather than irregular-looking older freckles.

Symmetry

Global strategies of darkening can be used to deemphasize non symmetric features.

Effectiveness with Surroundings

Another general principle for enhancement is that certain characteristics of skin, particularly with regard to color, may be considered more attractive when designed for their effects with surrounding elements. For example, different colors and shading may be more desirable at night rather than during the day or to match a red dress rather than a blue one.

Environment-Specific Makeup

The considerations of surroundings when creating desired effects may, for example, lead to different enhancements for night vs. day, colors and styles of clothing and jewelry, environment like the beach, a forest, or an office, and the color of the user's eyes.

Means of Determining a Desired State of the Skin Characteristic

Approaches for corrections include pure mathematical techniques and artificial intelligence techniques. By contrast, artistic approaches are more intuitive and less quantitative.

Mathematical
Artificial Intelligence
Artistic

Mathematical Means

Mathematical techniques include filtering to remove a portion of middle frequencies, and to remove a portion of asymmetric low frequencies. Another example of a pure mathematical technique is printing in opposition to an image in order to make the skin appear more uniform. This treatment can vary by spatial frequency, and it is typically preferable to have uniformity in the mid-frequency. Low frequency corrections may be more AI or artistic based for correction over larger areas of the skin.

Figure 28:
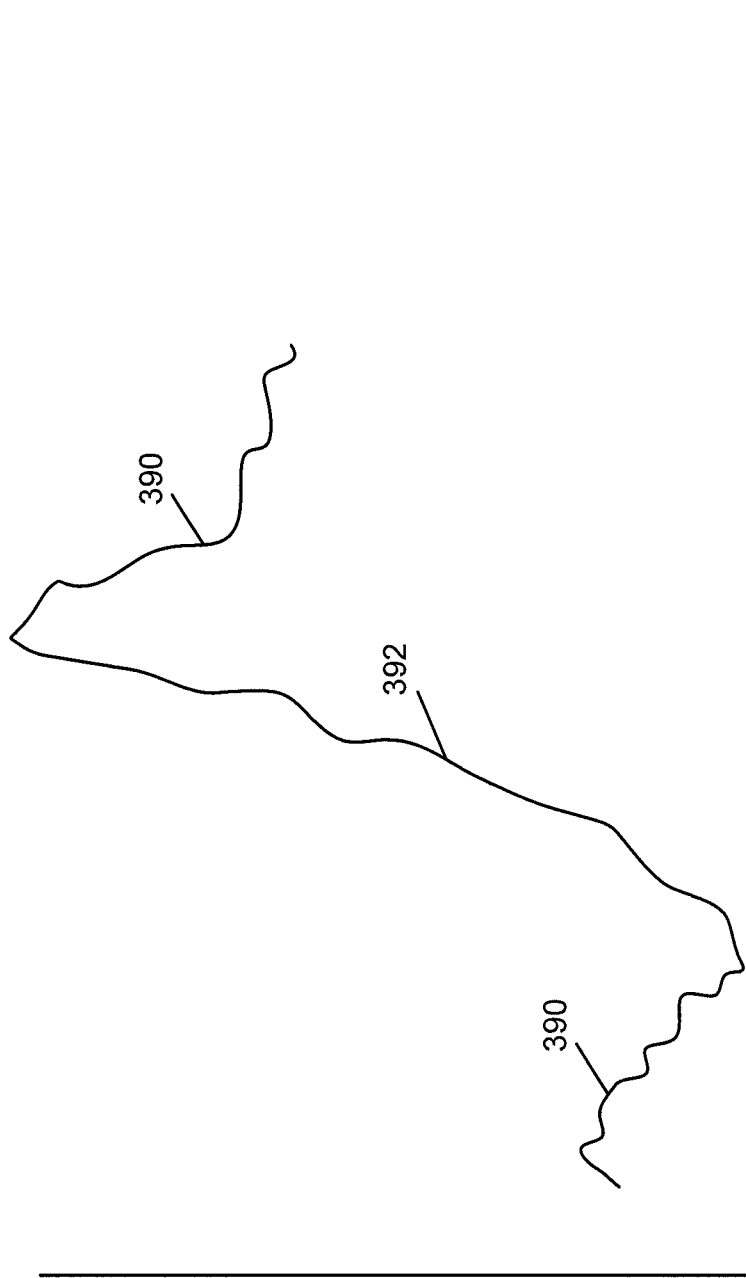
FIG. 28 is a generalized graph of weaker and stronger middle frequencies.

In an embodiment, a low-pass filter may be performed with a desired range of wavelengths. In one example, one half inch to one inch wavelengths are filtered to remove a portion of the middle frequencies. As shown in FIG. 28, weaker middle frequencies 390 show less pronounced swings between light and dark points than stronger middle frequencies 392. In an embodiment, the weak middle frequency components are removed to smooth an image.

Performing a Derivation of the Low-Pass Filter

In an embodiment, a low-pass filter may be performed, such as where a color value for a frexel is replaced by the average color value of its neighbors.

Artificial Intelligence Means

Artificial intelligence techniques include expert systems for detecting particular skin features, and selection of correction strategies. In one embodiment, the skin features are correlated to a registry or map, to identify feature locations. The registry allows for improving faded or distorted body painting and tattooing.

Features Library

Another aspect of AI techniques is the use of a features library for feature identification, and for comparison of actual features with idealized features.

Artistic Means

Computer Controls

In an embodiment, a human observer may optionally use means, such as a computer screen, keyboard, and mouse, to make further modifications in the perceived depth of the scanned area in order to accomplish aesthetic enhancements. A makeup artist or the customer may interact with the computer screen through controls to experiment with enhancements before the application.

A "cosmetic markup language" to provide general instructions such as to darken the top surface of bumps to the left of the nose; or to lighten varicose veins may be employed. The cosmetic markup language simplifies the correction process.

Touchups with Traditional Cosmetics

In one embodiment, traditional cosmetics are used to touch up a region of skin. Most of the adjustment is applied automatically, so that the amount of cosmetics required is greatly reduced.

Examples of Desirable Enhancements
   Smoother skin,
   Crisper freckles,
   Tanning.
Desirable Enhancements Through Advance Feature Mapping
   Beauty marks
   Such as darker-appearing moles and deeper-appearing dimples.
   Blond arm hairs
   Women might want dark skin and blond arm hairs. In one embodiment, RMAs may be applied to the hair to create desired effects. In another embodiment, RMAs may be applied to the skin around the hair to create desired effects.
   More prominent features
   Darkening can also be used under certain features, such as breasts, cheekbones, eyes, knees, and lips, to emphasize them by apparent elevation.

Techniques for Creating Desirable Enhancements

Smoother Skin

To accomplish the smoothing without removing stronger desirable features, the scanned data may be divided into spatial frequency bands. In the spatial frequencies between 2 mm to 12 mm, weaker waves below for example 10% peak to peak reflection can be attenuated, but stronger waves can be retained. In the range ½ to 2 mm, the same can be done with a higher threshold, below ½ mm the spatial frequency waves can be retained. In the range 12 to 25 mm, the same threshold can be applied under restricted control.

This method leaves attractive variety in the skin while smoothing the skin over all. This approach is superior to tanning, which flattens all the frequencies.

Crisper Freckles

Freckles may be enhanced or crisped by leaving low frequencies, which show natural uniformity. Dyes may be applied to countermand high frequencies, which show unattractive irregularities.

As shown in FIG. 22 and explained above, a pattern for a natural freckle of young skin 442 has a much more regular and symmetrical pattern, which makes the natural freckle 442 appear crisper, than the pattern of an age-related freckle 440. This natural pattern 442 may be used as an aim pattern 448 for comparison with the pattern for the random freckle 440. The difference between the random freckle 440 pattern and the aim pattern 448 may used as the desired characteristic. And a printable enhancement image 234, as shown in FIG. 1, may be created to accomplish this enhancement.

A method to derive a youthful freckle pattern from a general scan of skin is as follows. First limit the spatial bandwidth of the skin image to a band, such as between one cycle per mm and one cycle per four mm. Next, threshold this band-limited image so it will be either a constant "freckle" dark color or "no freckle" light color, with the no freckle predetermining for typically 80% or more of the area. This pattern tends to appear like youthful freckles with sharp, crisp edges; yet it follows age spots and other skin imperfections, allowing these imperfections to be camouflaged as young freckles without darkening the entire skin surface to the darkness of the imperfection In one example the enhanced freckles are created. For example, in older women, the analysis of the scanning may find areas that are too dark, and the correct techniques may leave those areas as freckles, but apply dyes to achieve the effect of the appearance of younger-looking freckles, as outlined in FIG. 22C.

Freckles are typically identified by recognition of their characteristic patterns in the different color bands.

Working with Multispectral Bands

In an embodiment, effective techniques may be employed to enhance the patterns identified in multispectral bands, such as RGB bands. For example, as explained above FIG. 25 shows RGB patterns for a scar 460, an age-related freckle 468, a varicose vein 476, a bluish bruise 484, and a yellow bruise 492, all in young skin. The following techniques are effective when the skin as a whole is being darkened in middle frequencies to smooth it, as explained above.

Scar

To enhance the scar 460, RMAs of magenta and yellow but not much cyan may be applied to it. This adds red color to the pale-looking scar 460.

Varicose Vein

To enhance the varicose vein 476, less of the darkening RMAs may be added to the areas surrounding the varicose vein 476.

Age-Related Freckle

To enhance an age-related freckle 468, less of the darkening RMAs may be added to the area of the freckle 468.

Bluish Bruise

To enhance a bluish bruise, less cyan RMA can be added during the general darkening.

Yellow Bruise

To enhance a yellow bruise, less yellow RMA can be added during the general darkening.

Applying at Least One Reflectance Modifying Agent

Types of Reflectance Modifying Agents (RMAs)

The current invention may utilize a variety of Reflectance Modifying Agents (RMAs), including Analine,
Food coloring,
UV,
Transparent Dyes,
Transparent Inks,
Pigments,
Oxidizers,
Tanning agents,
Bleaches, and
Chemically altering agent.

For example, a dye does not reflect light, but changes the skin reflectance, acting primarily by absorbing light.

In an embodiment, the RMAs can have a time delay, so that their application does not have an immediate effect but takes effect later through a triggering agent. For example, the RMAs can comprise one or more photosensitive materials that can be selectively exposed by a modulated beam of ultraviolet or other light or other forms of light and later developed by a chemical agent applied uniformly over the surface. For example a photographic emulsion of a light based material may be used, of which silver based halides are a good example.

Multiple Passes

In an embodiment, the RMAs may be applied to the skin by scanning and printing almost at the same time and making multiple passes over the skin. Several advantages result from using multiple pass application. Micro registration problems may be reduced because multiple passes permit dithering or blurring the image, as is well known to those skilled in the art. For example, multiple pass applications are useful for smoothing out the effects of hairs on the skin.

Also, multiple pass applications of RMAs allow time for the skin to assimilate the RMAs, which is especially important because some types of skin will absorb more than others.

The process for multiple pass applications is to make a partial application of the RMAs, then to scan again the area of skin that has received the partial application. A further application of RMAs can be made, and still further multiple pass scanning and applications can be made to approach an aesthetic goal.

Drop Control Application Techniques

Substances may be applied with "flow control" devices. These flow control devices typically may be characterized as "drop control techniques" where individual droplets of the substance are controlled; or "non-drop control techniques".

Spray devices and electrostatic spray devices are non-drop control techniques where droplets are produced and controlled only in aggregate. Often in a spray device, a lack of individual droplet control, or "randomness" is desired in order to produce a smooth application over a relatively large area. By contrast, in the current invention, it is desirable to provide very specific control of the amount and placement of RMAs.

Examples of drop control include "fine flow control" where the flow of the substance is precisely controlled to deliver droplets as desired; and "inkjet technologies." An older inkjet technology includes supplying a continuous flow of charged droplets past electrostatic deflector plates which are alternately charged so that the plates either permit a droplet to pass or deflect to a gutter. This technique was the original design basis for inkjet printers.

Other inkjet technologies include "drop on demand" such as thermal devices provided by Hewlett Packard, and piezoelectric devices such as provided by Epson and other printer manufacturers. In one embodiment of the current invention, the drop on demand technology is combined with charging the droplets.

Another embodiment of the current invention is the use of the older inkjet technology in a manner that delivers charged droplets in a scanned direction beam. Modern inkjet printers have been optimized for printing on flat surfaces over limited distances. The current invention prints on skin which is a dimensioned surface, and often requires a greater throw distance for the droplets. This greater throw distance can be facilitated with the better droplet aiming than is possible with a charged droplet. For example, drop on demand technology may be used to apply a single droplet of white pigment to spot in the face with pixel-level precision.

In another embodiment of the current invention, a non-inkjet drop control technique is used, such as fine flow control techniques.

As mentioned above, in this patent specification, the phrase "inkjet printer" is used for brevity represent any form of inkjet technology.

In an embodiment, an inkjet printer may be used to apply the RMAs onto the surface of skin, printing at a resolution of 300 dpi (11.8 dpmm).

In an embodiment, the inkjet printer may have multiple printer heads to speed the application. It may also traverse the body by robotics.

It is desirable to control the application of RMAs to a desired spray range. In one example, an inkjet printer has a desired spray distance of about ⅛ inch (3.2 mm). Various techniques may be used to guide the printer element over the surface of the skin in order to maintain that desired spray distance, such as a cup, as shown in FIG. 26.

In an embodiment, the head of the inkjet printer has a comb to keep hairs on the skin even and in fixed pattern, to smooth the hairs.

Dramatically Increased Precision

For aesthetic purposes, a small change in the direction of a perceived improvement often results in an unusually large perceived improvement. Humans can perceive differences in images or portions of images as a function of the square of the differences of intensity. This is seen in the common understanding that power is the square of a direct measurement of intensity, such as a voltage or current, or field strength such as magnetic or electrostatic in an electromagnetic wave. It is also derived statistically by the randomness of phasing between uncorrelated sources causing their net effect to add as squares, typically under a square root. For example, if a first image has a first intensity of a distracting, undesirable characteristic, and a second image has an intensity with only half (½) of the distracting characteristic, the second image will appear to the human eye to have about one quarter (¼) the damage of the distracting characteristic. This is one of the factors that permits substantial improvement in appearance in the current invention. Dyes can be deliberately and precisely applied in a manner to reduce the differences in intensity between portions of human skin. By reducing the faults of the skin even moderately, the "appearance" may be substantially improved. This is the reason that single color, as opposed to tri-color, or middle resolution printing as opposed to high resolution printing, or partial correction of defect as opposed to full correction, provides visually substantial correction.

In one embodiment, dyes can be applied with a precision that is equivalent to the resolution of the human eye. For example, a resolution of 20 pixels per millimeter at a distance of 10 inches (254 mm) is about 500 dots per inch (20 dpmm). This is a practical limit of the human eye resolution under good lighting conditions and a strong pure black and white contrast. Often, however, this high resolution is not needed, relaxing technical requirements of the camera and printing system.

Mapping-Based Enhancement

Example—Generating a Map of the Skin

This example demonstrates one method for generating a map of the skin, analyzing the map to generate a corrective plan, and executing the corrective plan.

Step 1—Scan Skin and Generate a Map of the Skin

In this example, the map of the skin is generated from data collected by scanning the skin at a first time.

In this example, the general process of creating a map of the skin involves obtaining data by scanning the frexels, and then processing that data to create the map. In this example, the processing includes determining the location of the scanning device and the frexel with respect to a reference coordinate system, determining the reflective properties of the frexel in multiple wavelengths, and determining the tilt or orientation of the frexel with respect to the coordinate system. Information about the frexel and its neighbors is then processed to make fine adjustments to the location of the frexel with respect to a portion of the body such as a face, so that a map can be generated. This fine adjustment includes referencing the frexel to the face, such as by referencing the frexel relative to recognized facial features.

a. Data Representation

An example of the data representation for a frexel is shown below:

$[(x_s, y_s, z_s, \alpha_s, \beta_s, \gamma_s),$
$(x_f, y_f, z_f, \alpha_f, \gamma_s),$
$\{(refl)_A, (refl)_N, (refl)_S, (refl)_E, (refl)_W\}]$ In this example, $(x_s, y_s, z_s, \alpha_s, \beta_s, \gamma_s)$ and $(x_f, y_f, z_f, \alpha_f, \beta_f, \gamma_f)$ represent the position and angular orientation of the scanner sensor and the frexel relative to a coordinate system.

b. Frexel Location Relative to Sensor or Coordinate System

The data elements $(x_f, y_f, z_f, \alpha_f, \beta_f, \gamma_f)$ may represent the distance of the frexel from the sensor, or may be an absolute position and orientation of the frexel with respect to a reference coordinate system. In one example, the determination of the distance from the frexel to the scanner may be made in two steps. A first step can be an approximate mechanically-based measurement such as a constant height of the sensor from the skin. The second step can be an optical first derivative measurement to provide a fine adjustment. In one example, the fine adjustment is calculated by measuring an angle from the surface. In another embodiment, a fine adjustment may be made by using two light sources to send out two reference points or grids for detection by a sensor.

c. Reflectance and Illumination Data and Calculations

The data elements $\{(refl)_A, (refl)_N, (refl)_S, (refl)_E, (refl)_W\}$ represent reflective data for the frexel under ambient lighting conditions, and for each of four light sources, such as LEDs, which are arbitrarily designated as north-south-east-west for ease of discussion. Other numbers of light sources, such as three sources, can be used, but the mathematics is simplified with four light sources. The (refl) represents one or more data point for the reflectance measurement.

The frexel data can be processed to determine a reflectance and an illuminance for each light source, and that information can be used to determine reflectance and surface profile.

In one example, the reflectance is the average or mean of all measurements. The illuminance can be determined from the known brightness of light sources such as LEDs.

d. Frexel Orientation

By determining the tilt of the frexel relative to two orthogonal axes, the orientation of the frexel can be determined. The orientation of a frexel and its neighbors is an indication of the actual local surface texture of the skin. One aspect of the current invention is the ability to measure and compensate for both local reflective properties and local surface texture.

In this example, there are four light sources which are designated as North, South, East, and West. The sensor obtains data when each light source is on, and the other sources are off. The sensor may also obtain data for ambient lighting, with none of the four light sources on. The tilt of the frexel can be determined by comparing the North and South measurements. The difference between these measurements is a related to the tilt of the frexel along the North-South axis. The difference between the East and West measurements is a related to the tilt of the frexel along the East-West axis.

e. Data Representation for Derived Values

An idealized data representation for data from a frexel is shown below. Various compression methods can be used to reduce the data storage requirements. In this example, each data element is shown as a complete set in order to demonstrate methods of registering the data and creating a map.

frexel data $[(x, y, z)$
  NS tilt,
  EW tilt,
  (R, G, B visual color albedo),
  time of acquisition$]_i$ The (x, y, z) represents the location of a frexel with respect to a coordinate system.

The NS tilt represents the tilt of the frexel relative to the EW axis. The EW tilt represents the tilt of the frexel relative to the NS axis.

The (R, G, B visual color albedo) represents the measured reflectance of the frexel in the red, green, and blue spectrum. One aspect of the current invention is that data may be obtained for multiple wavelengths, and that different wavelength data is useful in identifying skin features.

The human eye sees both reflectance and topology. In one embodiment of the present invention, data is obtained for both reflectance and topology.

Step 2—Register the Groups of Frexels.

The second step is to make some sense out of the data from a plurality of frexels.

This portion of the example is analogous to the problem of mapping the earth's surface from satellite or aerial photographs. In the case of aerial photos, a large number of photographs are slightly scaled, rotated, and/or translated in order to permit the images to be properly overlapped to reflect the actual earth surface. The map can then be generated from the properly overlapped images.

In the present example, one source of complexity is that data is captured at slightly different acquisition times, and it is necessary to compensate for movements of the skin and slight errors in calculated position.

This motion aspect is analogous to modeling in a gaming application. In gaming, a model of the body may include a model of the skeleton so that the body may be related to the skeleton. Movement may first be applied to the skeleton, and then the position of the body can be calculated from knowing the position of the skeleton and knowing the relationship between the skeleton and the body. In the current invention, the problem is the reverse, in that the shape of the body has been determined, and it is desirable to correct for motion during the measurement, a. Mapping a Frexel to a Map In this example, it is desirable to associate a frexel, or a group of frexels, with a position on a map. For instance, the frexel may be a portion of a face, and the map is an idealized map of a face.

In the case of a face, a model could be a rigid and upright face in an expressionless pose.

In one embodiment the determination of the desired amount of each of a plurality of dyes to be applied is made by generating a map of the skin at a first time; and analyzing the map to generate a corrective plan.

The corrective plan is then executed at a second time by making multiple passes over the skin with a device which includes a scanner and a dye applicator. The scanner provides data that is used to determine the location of the applicator and to determine how much additional dye is required for that location at each pass. The corrective plan provides a calculation of the total amount of dye to be applied to each small portion of the skin. In one example, a portion of the dye is applied in each of a plurality of passes over the skin.

Examples of Method

To illustrate embodiments of the present invention, examples are given below for enhancement processes for the following areas of human skin:

A face,

A leg, and

A breast.

Enhancing a Face

Undesirable and Desirable Characteristics in a Face

Figure 13:
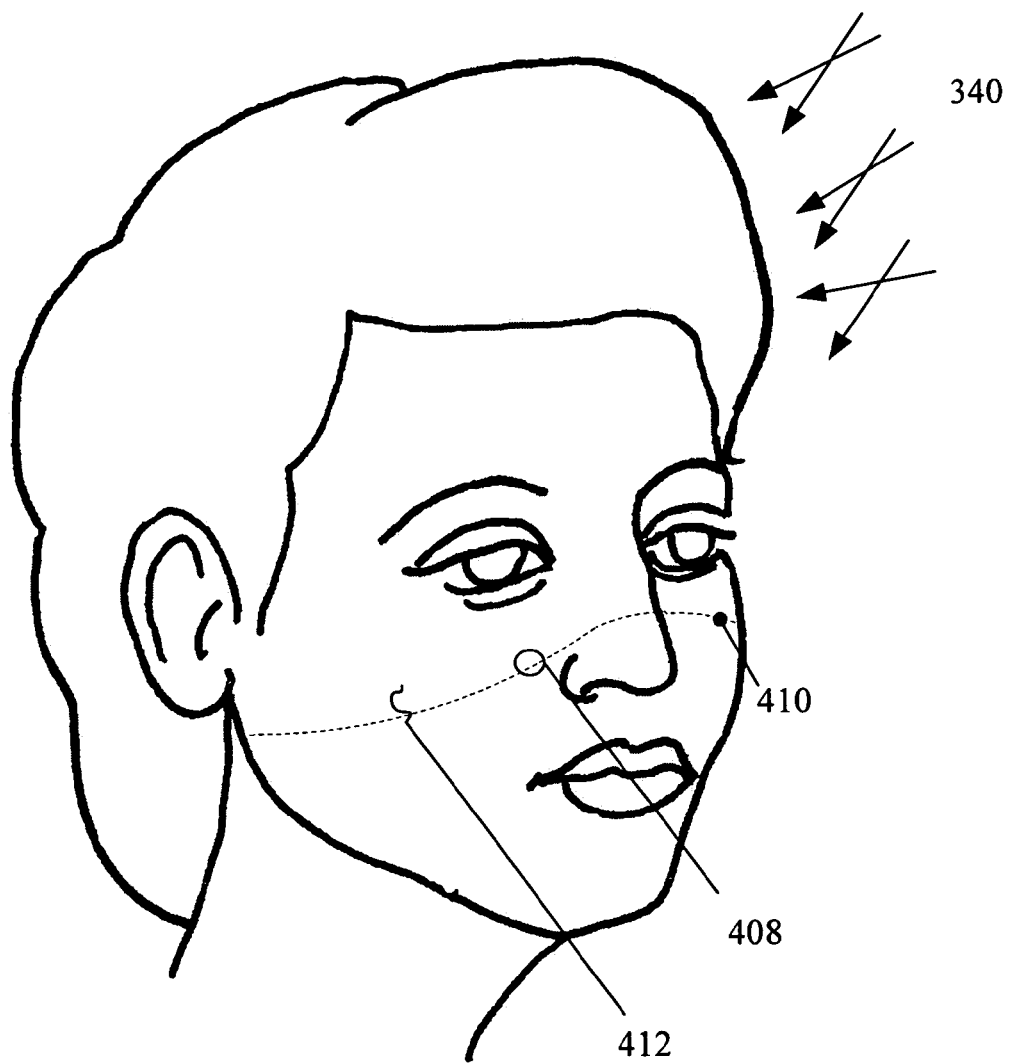
FIG. 13 is a diagram that illustrates characteristics or features on a 3-D human face.

FIG. 13 represents a human face 235 with certain characteristics:

A light spot 408,

A freckle 410, and

A non-uniformity 412 such as a scar.

FIG. 14 shows a representation of a 2-D surface map 232 of the face shown in FIG. 13, resulting from the scanning process used by the present invention and described above.

This 2-D surface map 232 in FIG. 14 retains the characteristics listed above, which may be identified by pattern recognition:

A light spot 408,

A freckle 410, and

A non-uniformity 412 such as a scar.

Note that the 2-D surface map 232 typically includes a representation of depth in order to capture the shape of the face.

To enhance such a face 235, shown in FIG. 13, according to the principles of attractiveness given above, it may be desirable to reduce or delete from view the undesirable characteristics, such as the light spot 408 and the non-uniformity 412. At the same time, it may also be desirable to retain or even augment the appearance of a characteristic such as a freckle 410, which can be a characteristic of youthful-looking skin. Unlike prior cosmetic techniques, which tend to cover over both undesirable and desirable features with makeup, the present invention can distinguish between the two and treat them appropriately.

Putting the Scanned Image into Spatial Frequency Bands

As shown in Step 606 of FIG. 31 and described below, the application algorithm 230 puts the scanned image into spatial frequency bands, in an embodiment, to permit identification of characteristics.

FIGS. 16A-E represent the patterns of the 2-D face 232, shown in FIG. 14, after the data has been put into spatial frequency bands.

Albedo

The top band in FIG. 16 represents the actual "albedo" of the 2-D surface map 232. A rise in the actual albedo graph identifies the light spot 408. A deep, sharp drop in the graph identifies a non-uniformity 412 such as a scar. And an irregular section identifies a freckle 410.

Illuminance (Shading)

The spatial frequency bands also graph the actual illuminance (shading) of the 2-D surface map 232.

Feature Recognition

Figure 15:
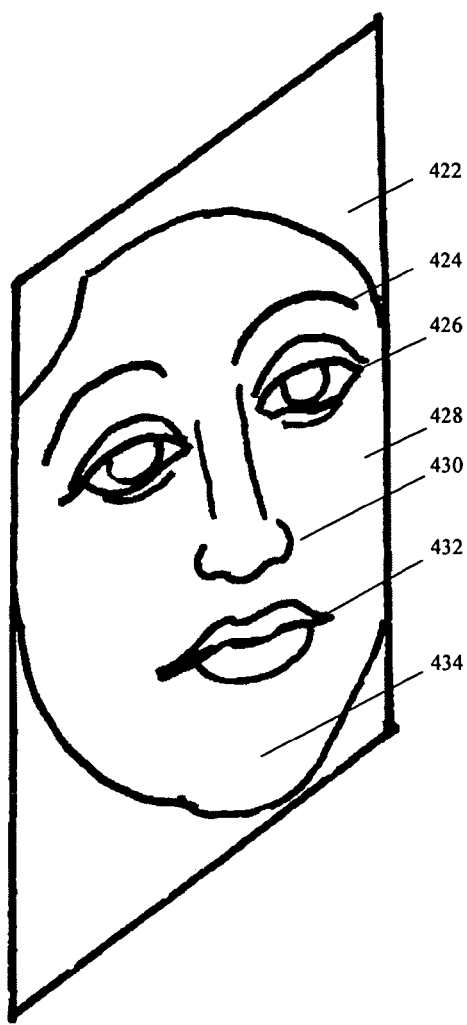
FIG. 15 is a perspective diagram that illustrates characteristics or features on a 2-D map of a human face.

FIG. 15 shows that pattern recognition can also identify features in the scanned 2-D surface map 232, such as Hair 422, An eyebrow 424, An eye 426, A cheekbone 428, The nose 430, The mouth 432, and The chin 434.

By identifying such features, the application algorithm 230 can determine whether to make enhancement to those features. For example, it is normally undesirable to print RMAs 264 on an eye 426. Therefore, the application algorithm 230 can remove the area that represents the eye 426 from consideration for enhancements.

Tracking

Figure 3:
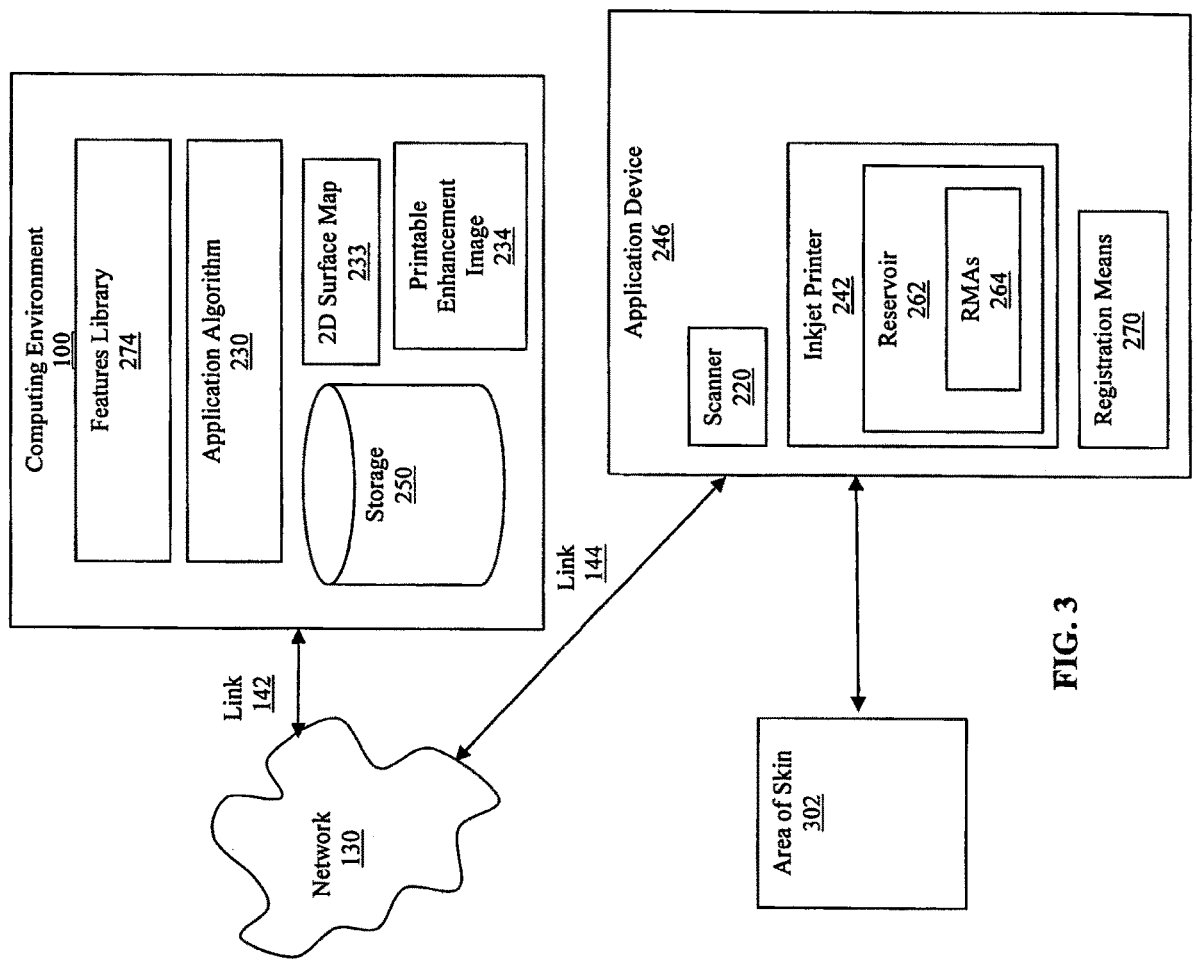
FIG. 3 is a block diagram showing an operating environment in which embodiments of the present invention may be employed for applying RMAs onto skin through communications over a network and a portable application device.

The application algorithm 230 may also use pattern recognition for tracking the location of the application device 246, for example the one shown in FIG. 3, on the area of skin 302.

As mentioned above, chemical markers may be alternately applied to the area of skin during the scan to help create the map and enable subsequent tracking of the map with the area of skin 302. For example, ultraviolet markers may be used.

Comparing Features with Idealized Features

Figure 2:
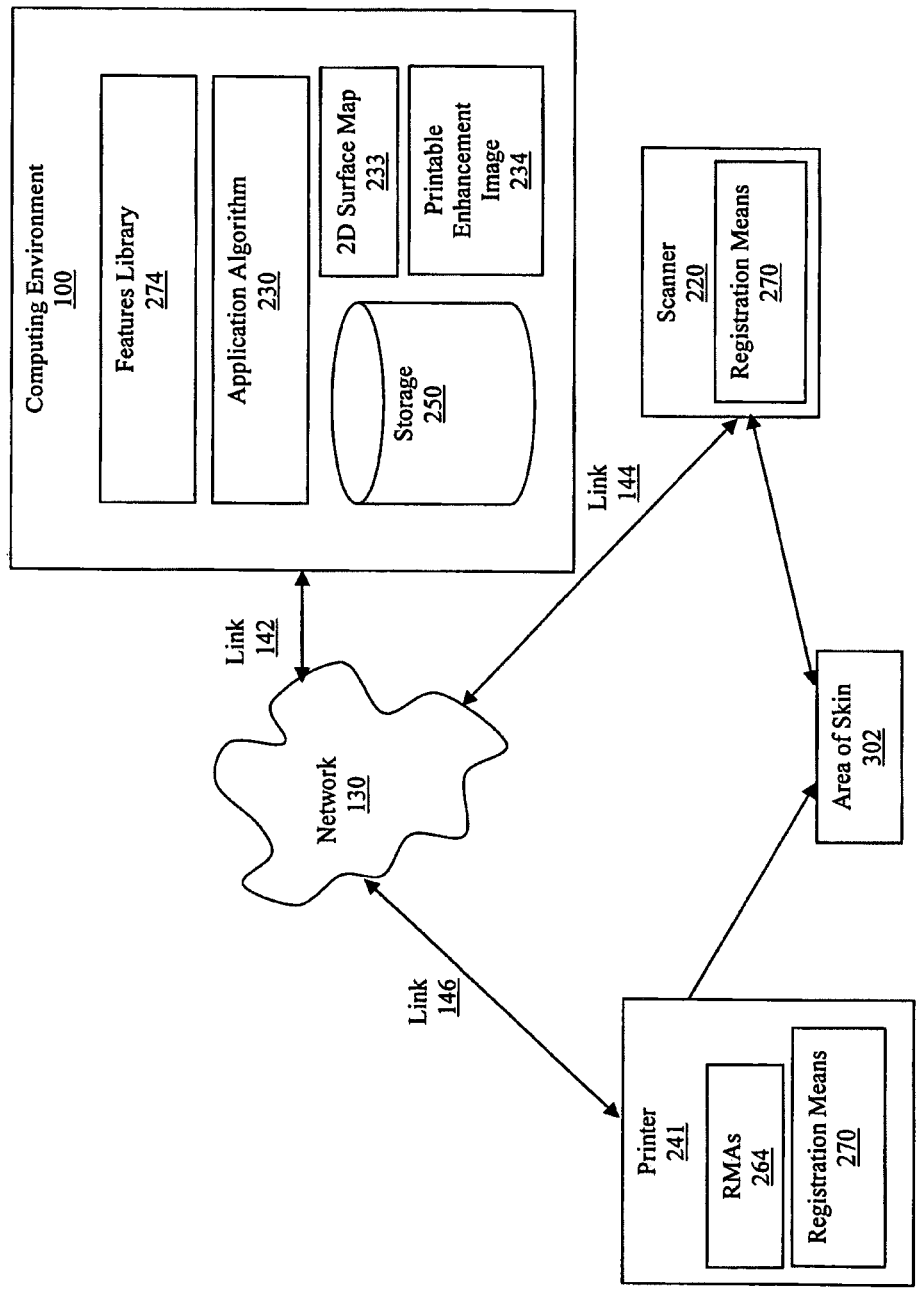
FIG. 2 is a block diagram showing an operating environment in which embodiments of the present invention may be employed for applying RMAs onto skin through communications over a network.

The application algorithm 230 may compare the mapped physical features with the idealized features in a features library 274, shown in FIG. 2, and use the comparison to modify features. For example, the application algorithm 230 may darken the area under a cheekbone 428 to match an idealized cheekbone that is more desirably prominent.

Thus the application algorithm 230 may apply to scanned features global guidelines established in the features library 274, shown in FIG. 2.

Determining the Actual Depth

Scanning the area of skin 302 provides the actual depth.

Determining the Aim Depth

In an embodiment, the aim depth can be the low spatial frequencies only of the actual depth. However, aesthetics may dictate additional sculpting, through further mathematical or manual input. The aim depth encompasses the effect of illuminance on perceived depth or texture, and is related to the amount and angle of incident light.

Carrying Out a Low-Pass Filter

In an embodiment, a low-pass filter may be performed with one half inch to one inch (12.7 to 25.4 mm) wavelengths to determine the aim depth to accomplish smoothing.

Determining the Actual Illuminance

Both actual and aim depths are translated into surface angle, as the first derivative, or slope, of depth. The surface angle is then translated into illuminance of the surface, as is well understood in 3-D modeling in applications such as gaming or animation graphics. Typically the assumed illumination angle and diffusion is mean light reaching the human skin.

Determining the Aim Illuminance

An aim reflectance may be derived algorithmically again simply as the low-pass version of the actual reflectance. However, additional aesthetic attributes may be added through mathematic or manual input.

Determining the Actual Albedo

The actual albedo is determined by the sensor of the application device, as described above.

Determining the Aim Albedo

The aim albedo is determined by the principles of correction explained above.

In this example, a generalized smoothing is performed, and specific feature correction is performed. For example, the light spot would be darkened, the freckle would be retained and possibly sharpened, and the scar would be at least partially camouflaged by a general darkening of the skin and a specific darkening of the light area on top of the scar.

The aim albedo is the desired perceived reflectance after calculating the smoothing and feature correction.

In other examples, the aim albedo may also include artistic strategies such as darkening one portion of a face relative to another.

Applying Aesthetic Objectives

In an embodiment, a human observer may optionally use means, such as a computer screen, keyboard, and mouse, to make further modifications in the actual depth of the scanned area in order to accomplish aesthetic enhancements.

The Enhanced Appearance of the Face

Figure 17:
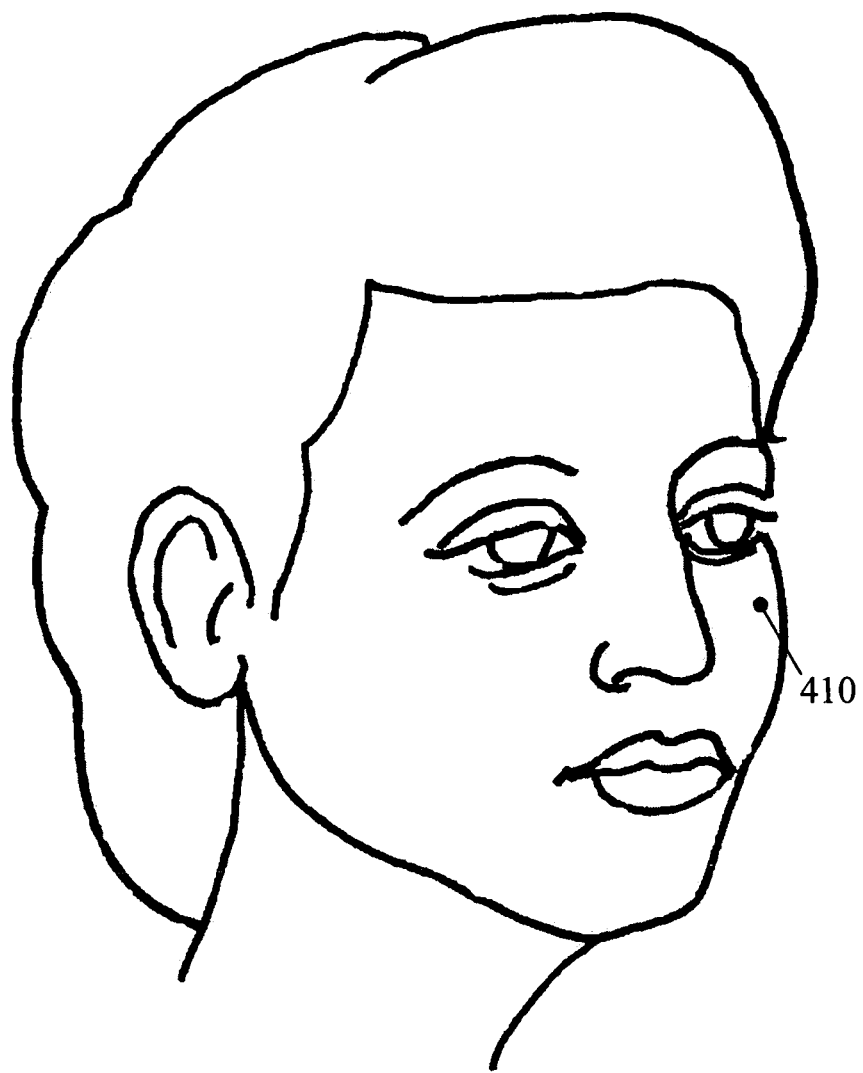
FIG. 17 is a diagram of a 3-D human face that has been enhanced through printing of RMAs according to a printable enhancement image.

FIG. 17 shows an example of the enhancement through the application of RMAs of the appearance of the face 235 portrayed in FIG. 13. The light spot 408 and non-uniformity 412 shown in FIG. 13 have been removed in FIG. 17. However, the freckle 410 has been retained in FIG. 17 as an attractive pattern of variety.

Single-Pass or Multiple-Pass Systems

Single-Pass

With sufficient computing power, the application device 246 will only need to make only one pass across the area of skin 302 to both scan the data and apply the RMAs 264.

Pigments

Figure 21:
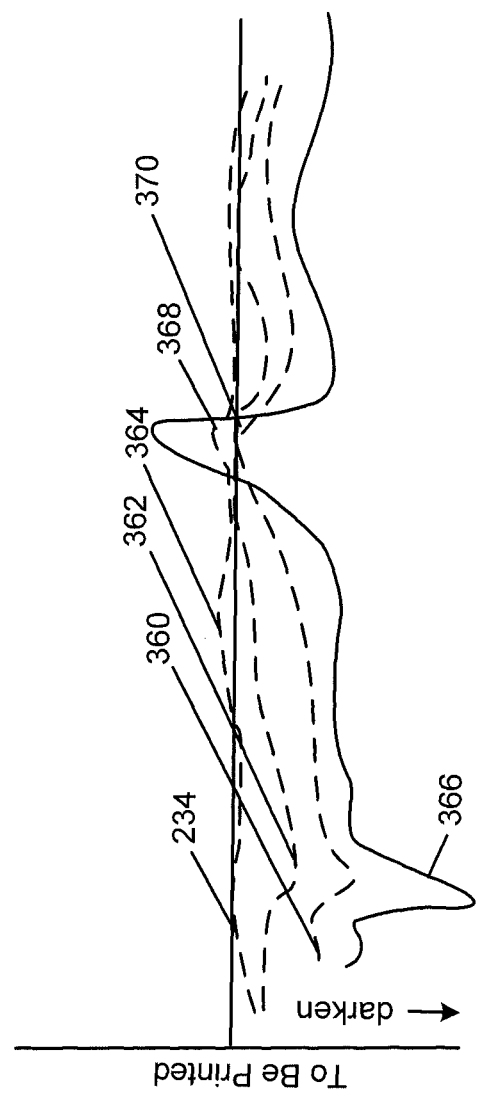
FIG. 21 is a diagram that illustrates performing multiple passes of scanning and applications.

Note that optional pigment pass 1 368 and optional pigment pass 2 370 shown in FIG. 21, may also be performed on areas to appear to lighten those areas. In such cases, a light-colored pigment such as white may be used rather than a negative dye 372. In other embodiments, a bleach or oxidizing agent may be used to lighten the skin rather than to apply light pigments. In this example, a dark spot, such as a pimple or vein, is lightened by the application of a pigment.

Multiple-Pass

In an embodiment, the user moves the application device 246 over the area of skin 302 many times. The application system then scans continually, creates a new 2-D surface map 233 after each pass, uses the 2-D surface maps 233 continually to identify the landscape of the area of skin 302 and calculate new printable enhancement images 234 with each pass, and applies only a portion of the RMAs 264, for example 10%-20% of the RMAs 264, on each pass. The use of multiple passes thus lets the application system 200 make a partial application of the RMAs 264, view the results of that application, and then make another partial application for further improvements. The continuation of these passes can ensure increased accuracy in the desired result. Application of the RMAs 264 in multiple passes also reduces the possibility of streaking and allows the RMAs 264 to dry between applications for greater effectiveness.

FIG. 21 illustrates how multiple passes may be used to apply a printable enhancement image 234 (exact aim) to an unprinted surface 366. To darken areas with a negative dye 372, meaning an RMA that appears to the human eye to darken an area, dye pass 1 360 is performed, so that some of the negative dye 372 is applied. Subsequently dye pass 2 362 is performed to apply more negative dye 372, followed later by dye pass 3 364 to apply still more negative dye 372. One advantage to applying the dye in multiple passes is that errors in scanning or printing tend to be smoothed. Moreover, errors are not just smoothed, but are corrected by feedback, much as a human would do, for example correcting in the second pass errors that were made in the first pass. Another advantage is that edge effects tend to be softened so that there are not undesired abrupt changes in color across the skin.

Note that optional pigment pass 1 368 and optional pigment pass 2 370, may also be performed on areas to appear to lighten those areas, as explained above. In such cases, a light-colored pigment such as white may be used rather than a negative dye 372. In other embodiments, a bleach or oxidizing agent may be used to lighten the skin rather than to apply light pigments.

Overlap Areas

In some examples of the current invention, it is desirable to make multiple passes of the applicator over an area. In the general case, as the applicator crosses over an area in a subsequent pass, some frexels will be seen for the first time, other frexels will have had a previous first pass, and still other frexels will have had two previous passes, etc. It is desirable to keep track of how many times each frexel has been passed over, so that this information can be included in the control algorithm for applying a desired amount of RMA.

It may be desired to correct, by example, 50% of the aim depositions of RMAs on a first pass. In the observation phase of the second pass, it may be noted that the application has produced more or less than 50% of the desired correction. Suppose this was seen to be 60%; so, only 40% remains uncorrected, and in addition it is now known that this part of the skin is responding with 6/5 stronger response to the RMA. So, by calculation only ⅚×⅘=⅔ of the RMA would be needed on the second pass to attain the desired effect. Suppose instead the algorithm chooses to deposit less than this on the second pass, then on a third pass makes a final observation and final calculation of efficiency and final deposition, to precisely titrate to the desired effect by feedback.

It is possible that the multiple passed could be in sequential scan order; so a top side of the probe always sees fresh skin, a middle processes an intermediate pass, and a bottom processes a strip of skin for the final pass. A more practical system allows random movement similar to the motion of an electric shaver, in which case software tracks the number of times a frexel of skin has been operated on. A sonic or tactile feedback could indicate the completion for each frexel, like an electric shave changes sound depending on completion of effect under each pass.

Since it is generally impractical to exactly meet an edge from a previous application pass, it is also generally desirable that the extreme portions of the applicator make a weaker application of RMA than in the middle of the pass. For instance, if the applicator were moved left to right on this page, then a lesser amount of RMA than calculated would be applied by the top and bottom portions of the print head so that there was an opportunity on a subsequent pass to print additional RMA in those areas to provide a better overlap of passes. It is also desirable to make each pass in a different orientation relative to the skin to randomize measurement or deposition fluctuations due to hairs, skin texture, or pulling distortions of skin, and not to repeat the same paths. For instance, if a first pass were made left to right, a second pass might be tilted slightly clockwise, and a third pass tilted slightly counterclockwise.

Summary of Enhancement Process

Figure 46:
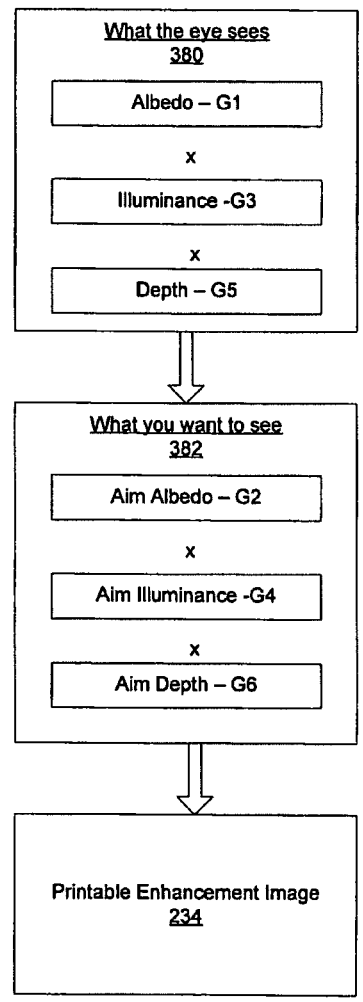
FIG. 46 is flowchart illustrating a correction process.

FIG. 46 shows the general process of one embodiment of the present invention to visually enhance objects such as an area of skin comprising a human face, in an embodiment. "What the eye sees 380" represent the scanned data about the area of skin 302. In terms of optics, this data comprises
- the albedo G1—which is the degree of reflectance from the surface of the area of skin 302;
- the illuminance G3—which is the degree of illumination G3 of the area of skin 302; and
- the depth G5—which is the distance from the scanner or other reference point to the portion of skin being measured
- the "tilt" or orientation of the portion of skin being measured. This orientation, when combined with information from adjoining skin areas, describes a surface profile of the skin.

"What you want to see 382" represents an enhancement that would make more attractive "what the eye sees 380." This enhancement, which may be calculated mathematically and optionally through manual visual corrections, comprises
- an aim albedo G2—which is a more attractive degree of reflectance from the surface of the area of skin 302;
- an aim illuminance G4—which is a more attractive degree of illuminance G3 of the area of skin 302; and
- an aim depth G6—which is the desired perceived distance from the scanner or other reference point to the portion of skin being measured Note: In one embodiment, the correction to be applied is a mixture of transparent dyes, such that the mix and the amount of the dye is determined in response to the perceived reflectance of the local area of the skin—which is related both to the actual reflectance and to the skin surface profile. Thus the correction applies a desired RMA to compensate for actual reflectance, and applies a shading to hide or enhance surface features.

In an embodiment, the mathematical calculations to create the aim albedo G2, aim illuminance G4, and aim depth G6 may be performed with particular effectiveness through mid frequency filtering.

By calculating "what you want to see 382" according to the principles of attractiveness given above, a printable enhancement image 234 may be created for printing on the area of skin 302 to make that area of skin 302 more attractive.

Steps in the Enhancement Process

Figure 33:
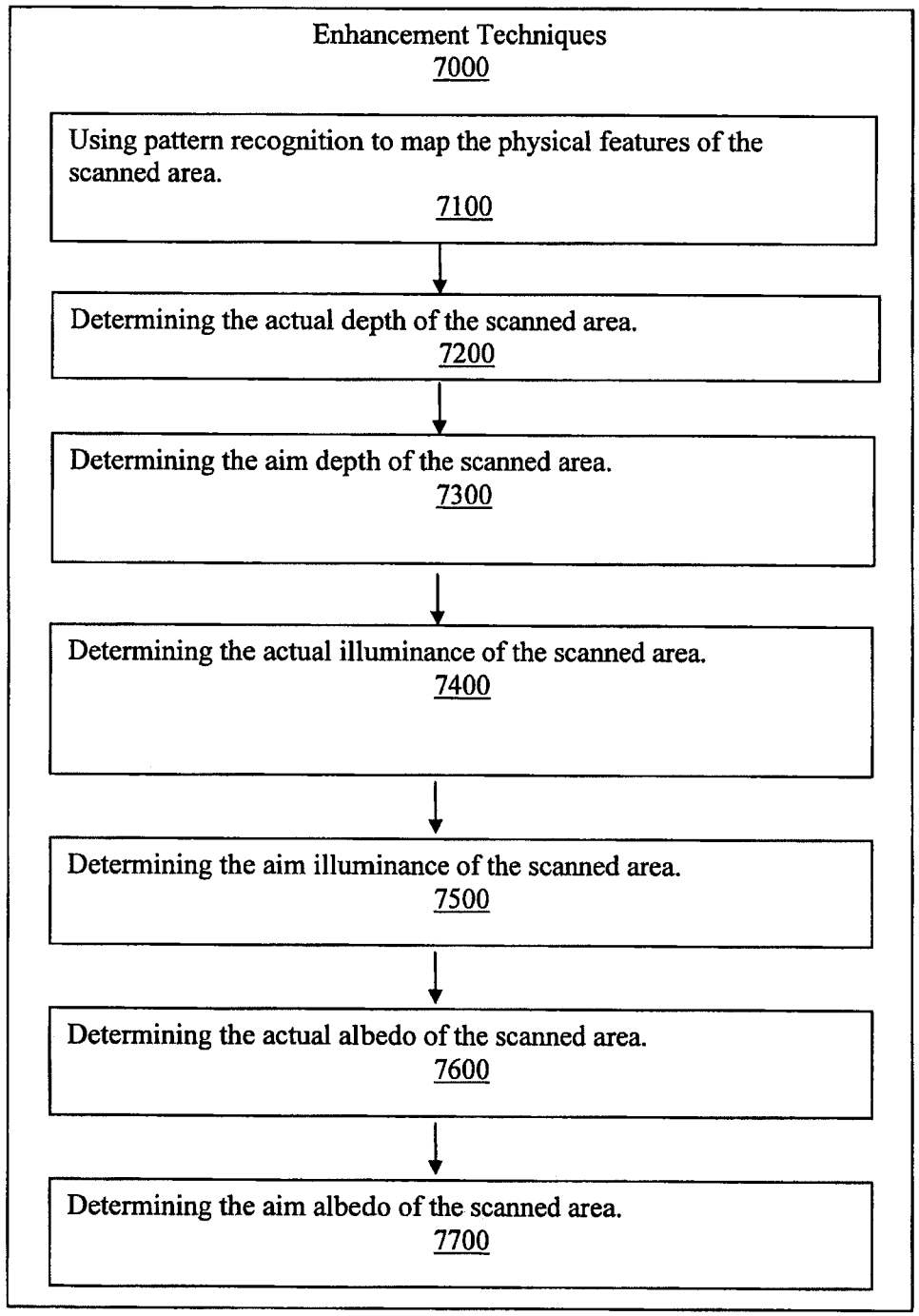
FIG. 33 is a flow chart showing a process for employing enhancement techniques.

FIG. 33 shows steps in a process for accomplishing the present invention's enhancement techniques in an embodiment:
- Step 7100 of FIG. 33—Using pattern recognition to map the physical features of the scanned area;
- Step 7200 of FIG. 33—Determining the actual depth of the scanned area.
- Step 7300 of FIG. 33—Determining the aim depth of the scanned area.
- Step 7400 of FIG. 33—Determining the actual illuminance of the scanned area.
- Step 7500 of FIG. 33—Determining the aim illuminance of the scanned area.
- Step 7600 of FIG. 33—Determining the actual albedo of the scanned area.
- Step 7700 of FIG. 33—Determining the aim albedo of the scanned area.

Figure 34:
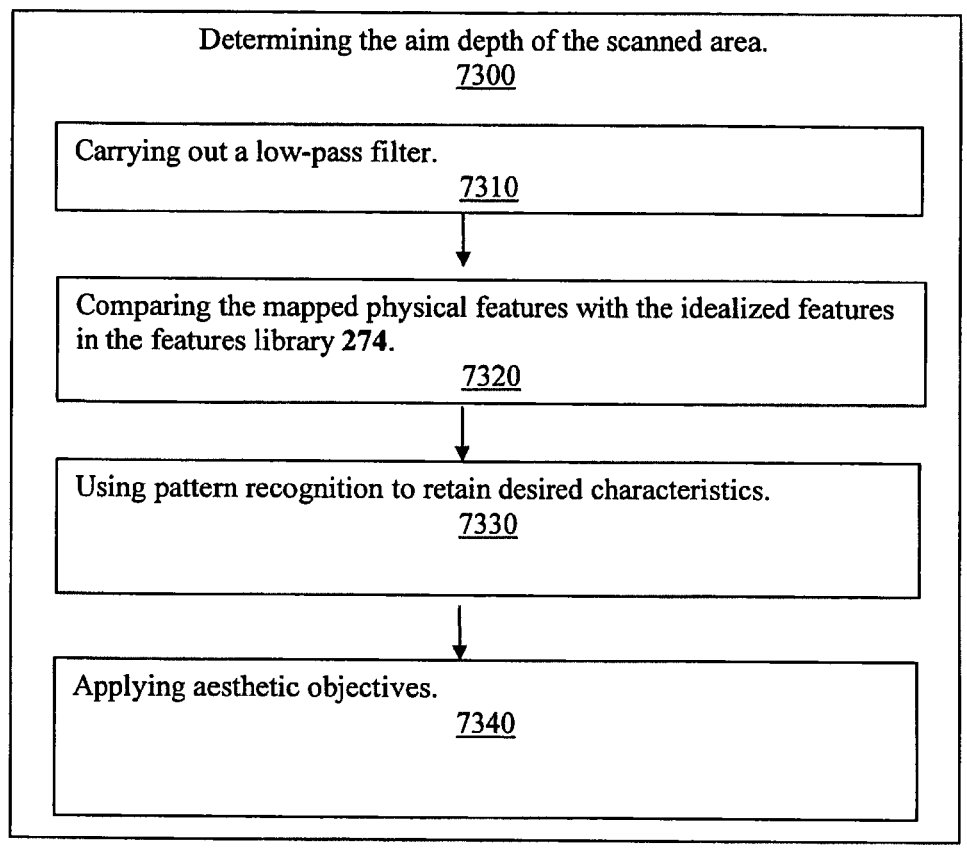
FIG. 34 is a flow chart showing a process for determining the aim depth of the scanned area.

FIG. 34 shows steps in a process for accomplishing step 7300 of FIG. 33.
- Step 7310 of FIG. 34—Carry out a low-pass filter.
- Step 7320 of FIG. 34—Compare the mapped physical features with the idealized features in the features library 274.
- Step 7330 of FIG. 34—Use pattern recognition to retain desired characterisitics.
- Step 7340 of FIG. 34—Apply aesthetic objectives.

Figure 35:
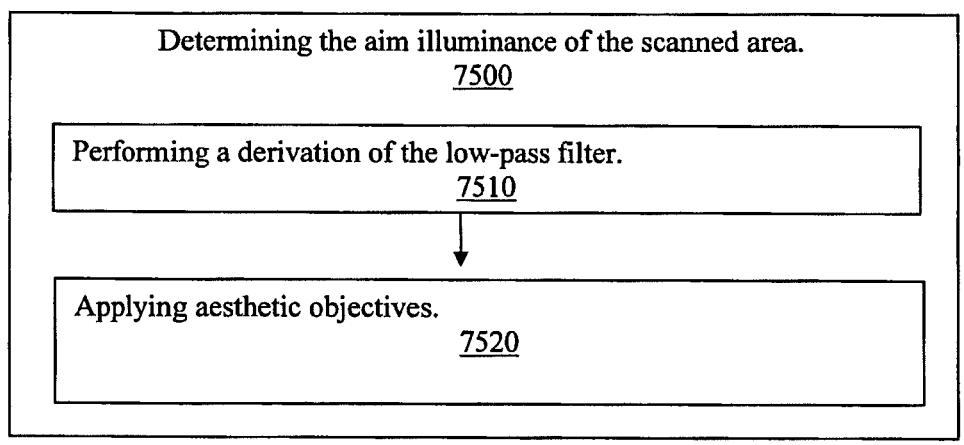
FIG. 35 is a flow chart showing a process for determining the aim illumination of the scanned area.

FIG. 35 shows steps in a process for accomplishing step 7500 of FIG. 33.
- Step 7510 of FIG. 35—Perform a derivation of the low-pass filter.
- Step 7520 of FIG. 35—Apply aesthetic objectives.

Enhancing a Leg

Undesirable and Desirable Characteristics in a 2-D Leg

Figure 18:
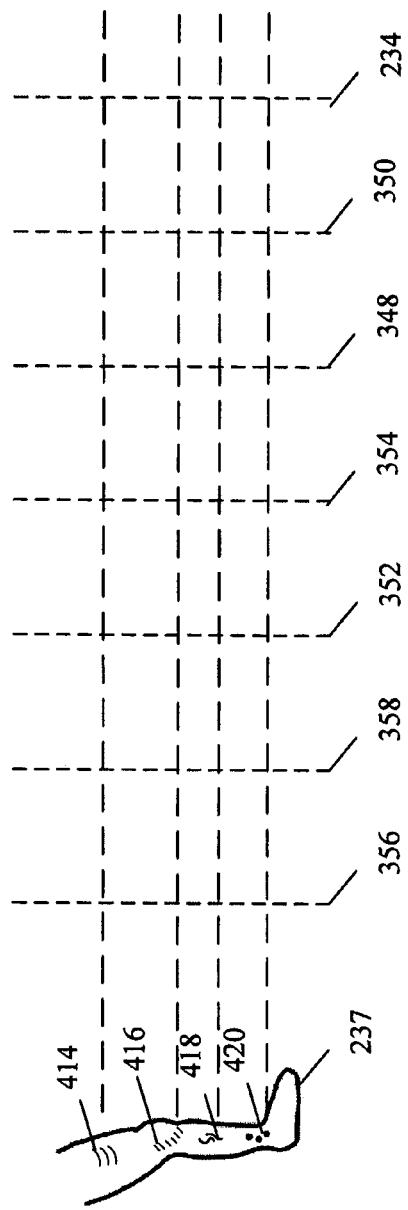
FIG. 18 is a diagram that illustrates characteristics of a 3-D human leg, with the corresponding reflectance per spectral base on a 2-D map, and a printable enhancement image.

FIG. 18 shows an illustration of a human leg 237 with the following undesirable and desirable characteristics:
- Cellulite 414,
- Natural color differences 416,
- Varicose veins 418, and
- Age spots 420.

The spectral bands for these characteristics are also shown, including one for a printable enhancement image 234 that may be used to print enhancements onto the leg 237. To simplify the illustration, a 2-D skin map is portrayed as a 1-D graph following the dotted line across the surface of the skin.

The actual depth along this line is graphed. In addition, one obtains an aim depth. The aim depth can be the low spatial frequencies only of the actual depth. However, aesthetics often dictate additional sculpting, as is known in cosmetology.

Both actual and aim depths are translated into surface angle, as the first derivative, or slope, of depth. The surface angle is then translated into illuminance of the surface, as is well understood in 3-D modeling in applications such as gaming or animation graphics. Typically the assumed illumination angle and diffusion is mean light reaching the human skin.

Printing on the skin has negligible effect on surface depth. However, the visual illusion of depth is obtained by printing the shadowing. Cellulite is not actually perceived stereoptically at more distance than approximately six inches. The human eye perceives cellulite primarily by shadowing.

Note how tanning produces pigmentation in opposition to mean illumination reaching the skin, and thus is in opposition to mean shading, thus making a sun-tanned human body appear smoother and more attractive. Note that rub-on tanning solutions do not have this characteristic of being sensitive to skin angle relative to light, and thus fail to provide the same attractiveness.

The leg example also illustrates pigmentations and varicose veins. An aim reflectance may be derived algorithmically again simply as the low-pass version of the actual reflectance; however, aesthetic attributes may be added, such as freckles, which may align with existing pigmentations, while excluding age spots. It may also include other selected features, such as knee cap darkening.

It should be understood that the aim and actual reflectance curves can represent each color separately. For example, varicose veins may be blue or red, while pigmentation may be orange. Thus each color is independently corrected using colored inks, such as the process colors cyan, magenta, and yellow.

The perceived light visualized from the leg by a human observer is the illuminance*reflectance (albedo). It is actually actual illuminance*actual reflectance, but is desired to be aim illuminance*aim reflectance. Thus to go from actual to aim, a multiplying (or dye) image should be deposited on the skin, that is $$\frac{\text{translated aim angle}}{\text{translated actual angle}} * \frac{\text{aim reflectance}}{\text{actual reflectance}}$$

where "translated aim angle" is the aim angle translated to a standard illumination assuming mean illumination; and "translated actual angle" is the actual angle translated to a standard illumination assuming mean illumination. This provides the aim correctance, shown as the printable enhancement image 234. A separate aim correctance can be derived for each color, typically red, green, and blue to print, in order, cyan, magenta, and yellow.

A problem arises that with dyes it is only generally practical to darken the skin. (In other embodiments, it is possible to use limited amounts of whitening dyes or bleaching agents to selectively lighten areas.) Thus, as an expedient the aim paint is shifted (dotted line) so that more of the skin is correctable. This is equivalent to choosing a lower aim reflectance, for a more tanned appearance.

Some details, such as blue varicose veins on a leg, may still be outside the correction range even with the reasonable offset. These details can be corrected by depositing small areas of light pigment, than printing over with dyes to provide the right color. Alternately the extreme points can be left uncorrected. The relative error of uncorrected points is still much less noticeable if the adjoining skin is darkened somewhat.

Figure 19:
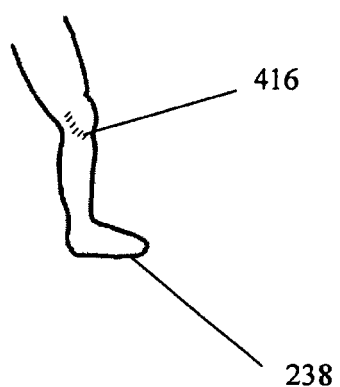
FIG. 19 is a diagram of a 3-D human leg that has been enhanced through printing of RMAs according to a printable enhancement image.

FIG. 19 shows an illustration of a human leg 238 after being enhanced through the present invention. The following undesirable characteristics, which were shown in FIG. 18, have been reduced from view:
Cellulite 414,
Varicose veins 418, and
Age spots 420.

However, the desirable natural color differences 416, which serve to make the 3-D quality of the knee cap visible, have been retained.

Enhancing a Breast

Figure 20:
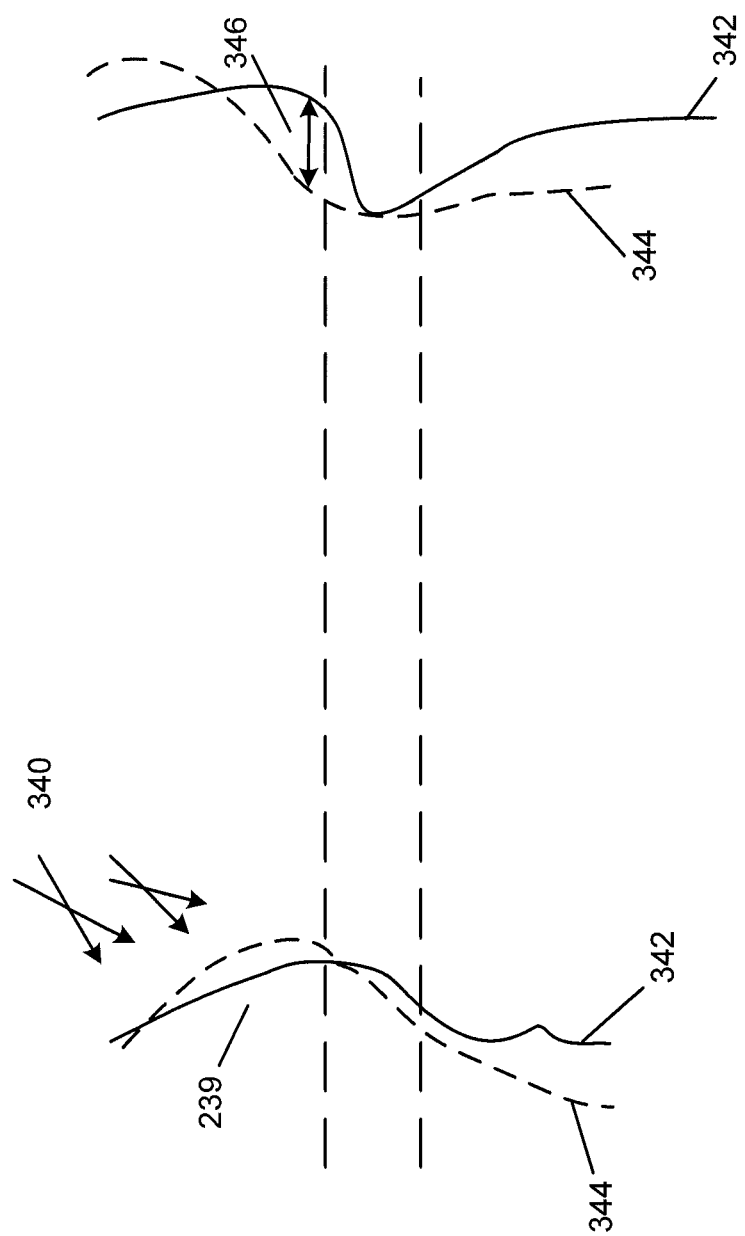
FIG. 20 is a diagram that illustrates characteristics of a 3-D human breast, with the corresponding reflectance per spectral base on a 2-D map.

FIG. 20 shows an example for changing the perception of a breast 239 from an actual 3D surface 342 under mean illumination 340 to an aesthetic aim 344 by determining the difference 346. Applying RMAs to approximate this difference will alter the perceived appearance of the breast.

Single Pass Smoothing Example

Figure 37:
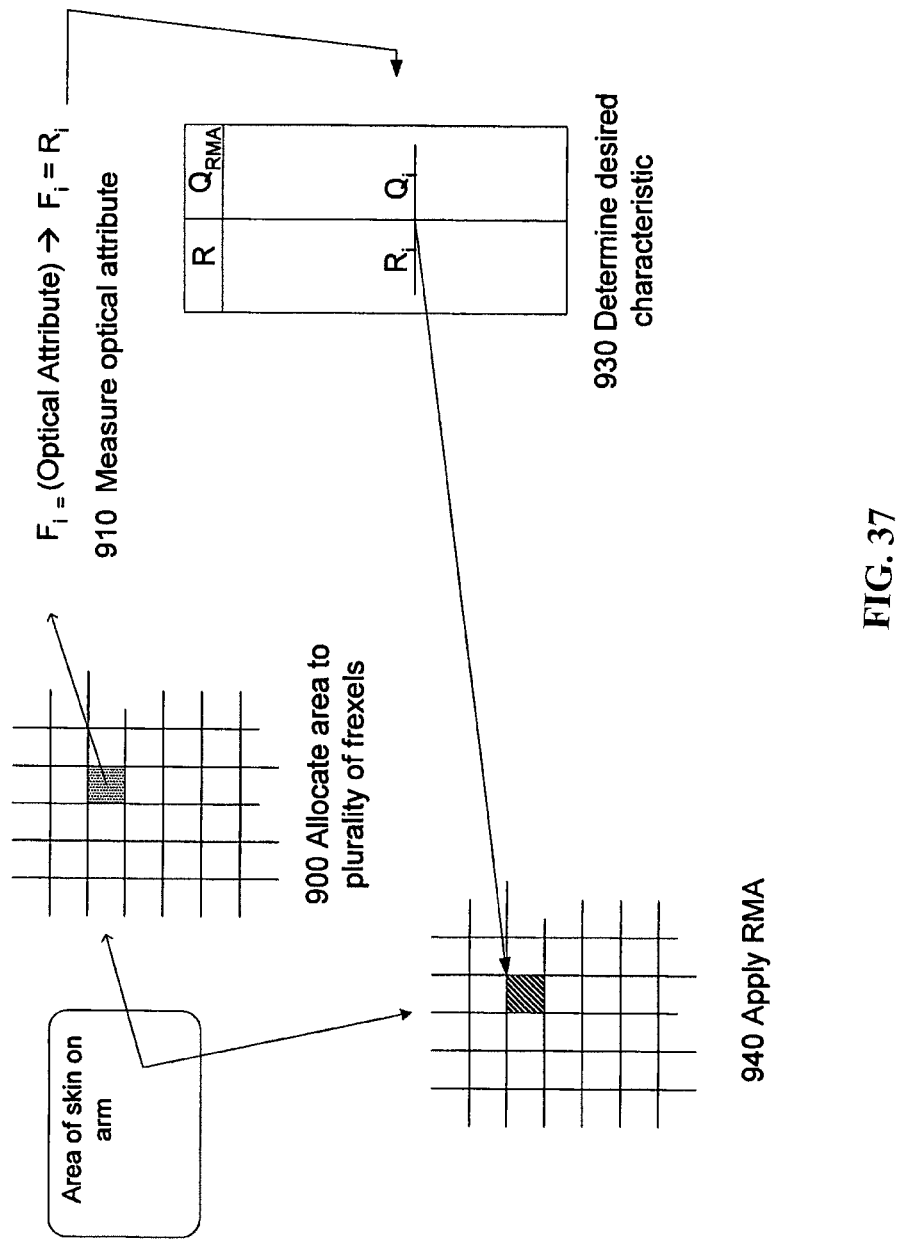
FIG. 37 is a schematic for a simple skin smoothing example.

FIG. 37 represents a simple smoothing example for skin. An area of skin, such as one on the arm, is broken into a plurality of frexels at step 900. At step 910, at least one optical attribute of the frexels is determined. The optical attribute is represented as There is a look up table which provides a quantity of a reflectance modifying agent to apply for each range of visual characteristic. At step 930, the quantity of RMA to be applied is determined from this look up table. The desired quantity of RMA is applied at step 940, thereby changing the appearance of the area of skin. This single pass example does not require a mapping of the skin.

Multiple Pass Smoothing Example

Figure 38:
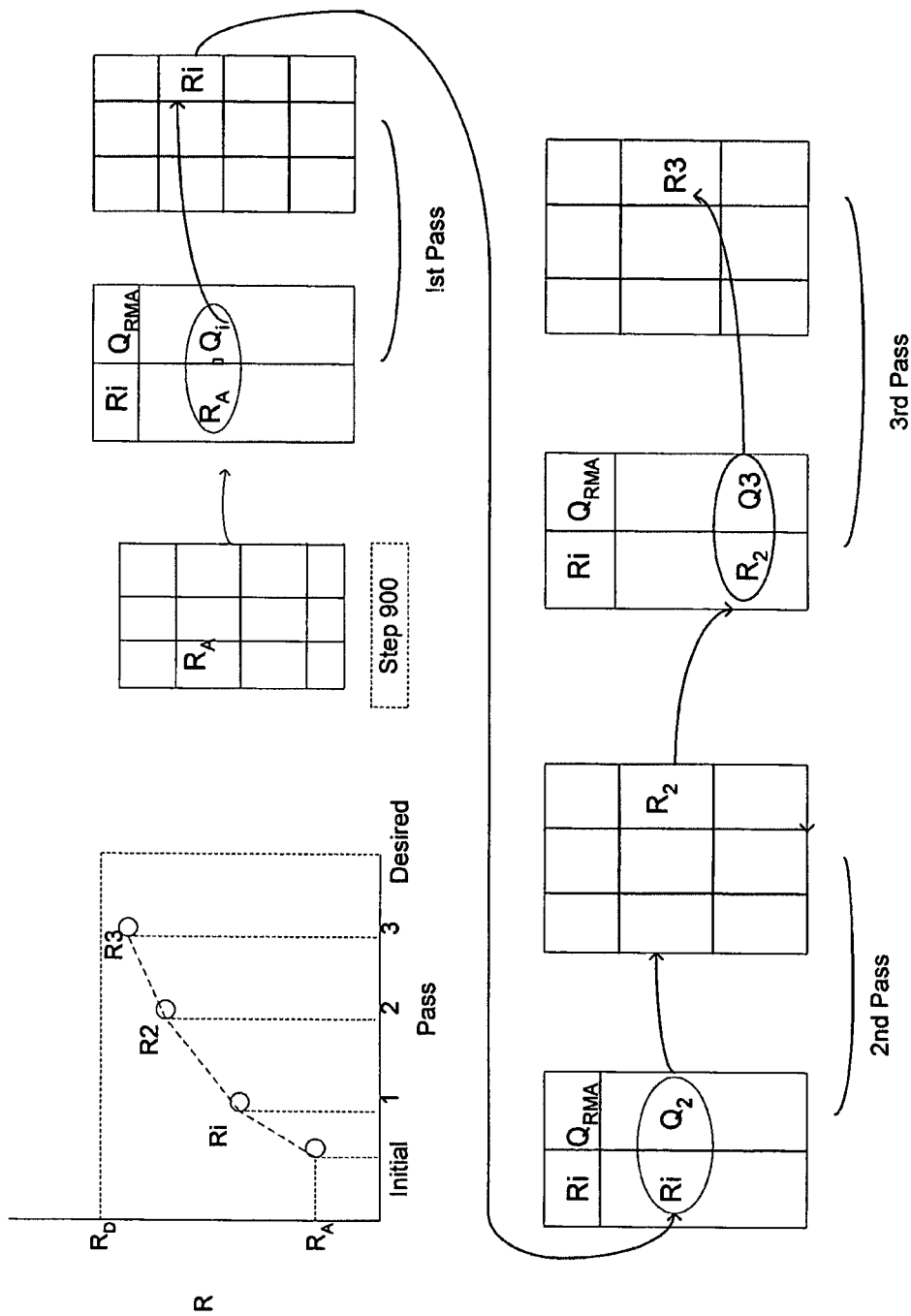
FIG. 38 is a schematic for a multiple pass smoothing example.

FIG. 38 represents a multiple pass smoothing of skin. In this figure, the desired reflectance $R_d$ is approached with a series of applications of a reflective modifying agent. The actual initial reflectance is determined at step 900 as $R_a$, and that value provides a first quantity of RMA to be applied in a first pass which is $Q_1$. The application of that first amount of RMA, $Q_i$, changes the reflectance from $R_a$ to $R_i$. At the second pass $R_i$ is used in the look up table to determine the second amount of RMA ($Q_2$) to be applied. When that second amount is applied, the reflectance is changed to $R_2$ On the third pass, $R_2$ is used to determine a third amount of RMA. ($Q_3$) The resulting reflectance $R_3$ approaches the desired reflectance. The number of passes is not limited to three but may be more or less than that number.

Facial Map Example

Figure 39:
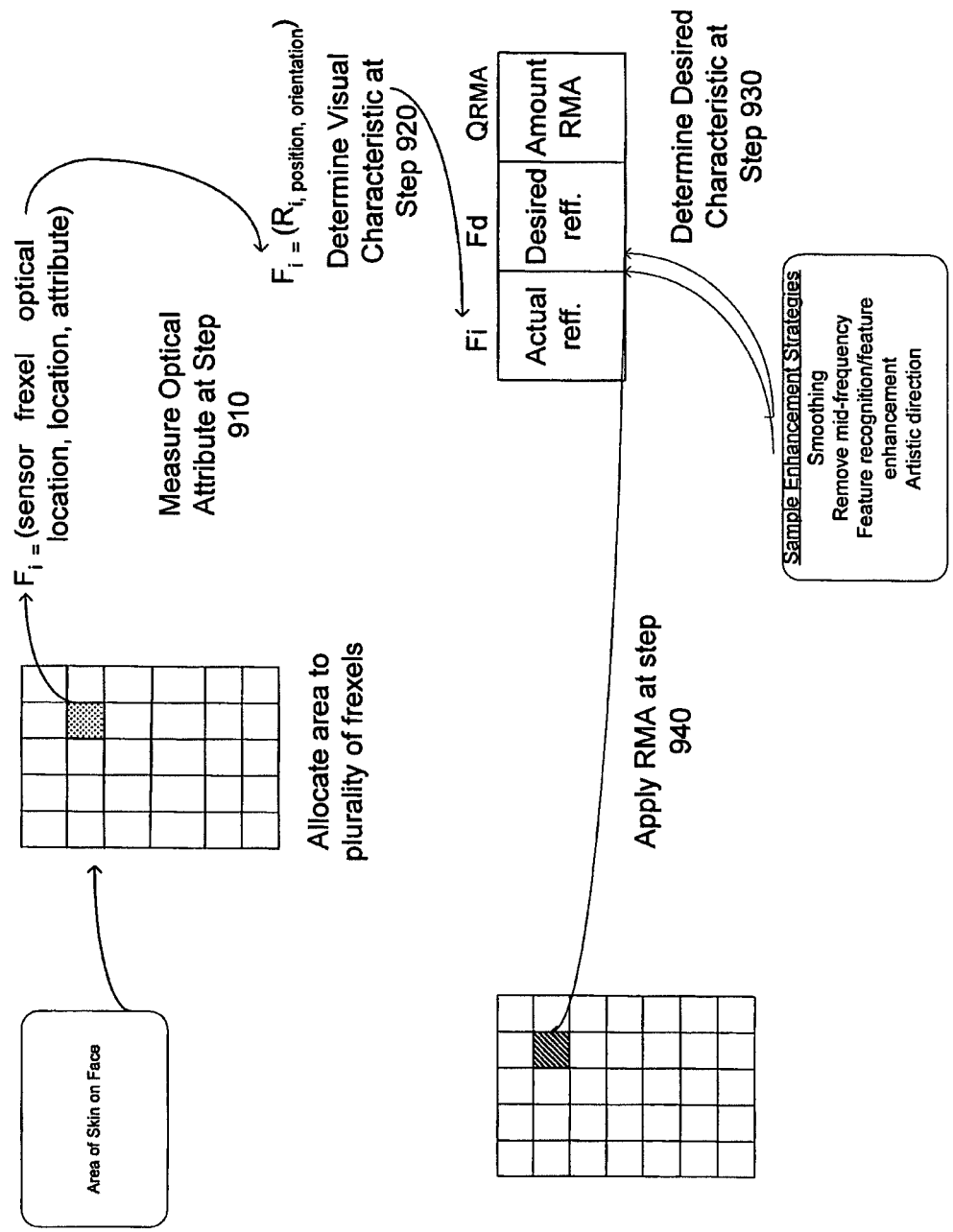
FIG. 39 is a schematic for a facial map example.

FIG. 39 represents a facial map example. In this example, the skin on a face is allocated into a plurality of frexels as before. The optical attribute is measured in step 910 as before, except that the frexel location is determined and specified and recorded so that there is location data for individual frexels. The data for individual frexels includes sensor location, the location of the frexel and one or more optical attributes. The optical attributes may be used to determine the reflectance, position, and orientation of the frexel at step 920. Each frexel then has an initial characteristic such as an actual reflectance. The frexel also has a desired final characteristic, such as the desired reflectance, and an amount of RMA to be applied in one or more passes. The amount of RMA is determined at step 940. The desired reflectance is determined from an enhancement strategy such as smoothing of the skin, filtering to remove middle frequency characteristics, feature recognition and feature enhancement, and general artistic schemes. The desired quantity of RMA is determined from the difference between the desired reflectance and the actual reflectance.

LED Arrangement

FIG. 40A is a schematic for sensor and LED arrangement. In this example a sensor is located along the axes of four LEDs which are designated as north, south, east, and west.

FIG. 40B is a cross section showing that the LEDs are typically directed to a point on the skin below the sensor. Typically the LEDs and sensors are provided in a housing, and the housing may have reflective properties to provide more diffuse or indirect light to the frexel in some applications. In other applications it is desirable to orientate the light directly at the frexel in order to determine the tilt of the frexel.

Depth may be determined by shadow parallax grid projected by LEDs from different angles. In another embodiment, two cameras may be used in a stereoscopy approach.

Feature Recognition

Figure 41:
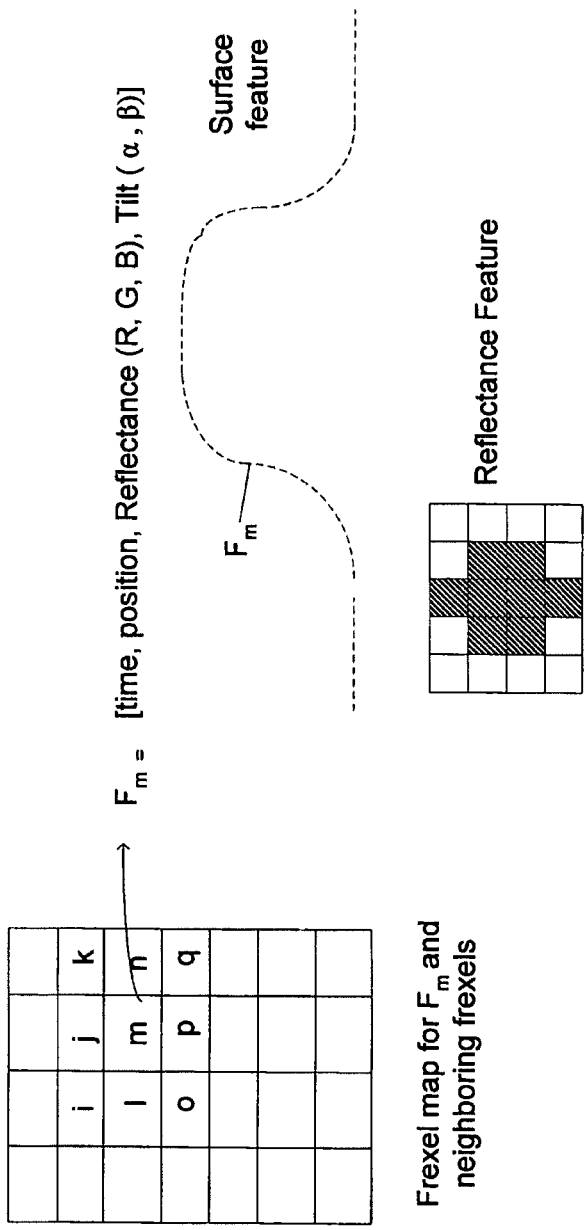
FIG. 41 is a schematic for feature recognition.

FIG. 41 shows a simple feature recognition approach. A frexel map for a particular frexel "m" and its neighboring frexels is represented. Data for each frexel typically includes the time, position, reflectance and orientation of the frexel. Information can be represented graphically as demonstrated in the reflectance feature portion of the diagram. At step 910, the skin is scanned to measure an optical attribute. At step 920, a visual characteristic such as reflectance is determined from the scan. At step 921, a facial map is generated to provide the actual visual characteristics as perceived by a viewer. At step 922, the frexel data is reviewed to identify local features and the parameters for the particular subject. An example of parameters is the range of readings in that subject, which can be used in normalization or other data manipulation. At step 924, enhancement strategies are applied. At step 925, an enhancement map is provided. The enhancement map includes the amount of RMA to apply to a particular frexel in order to change its visual characteristics.

Figure 42:
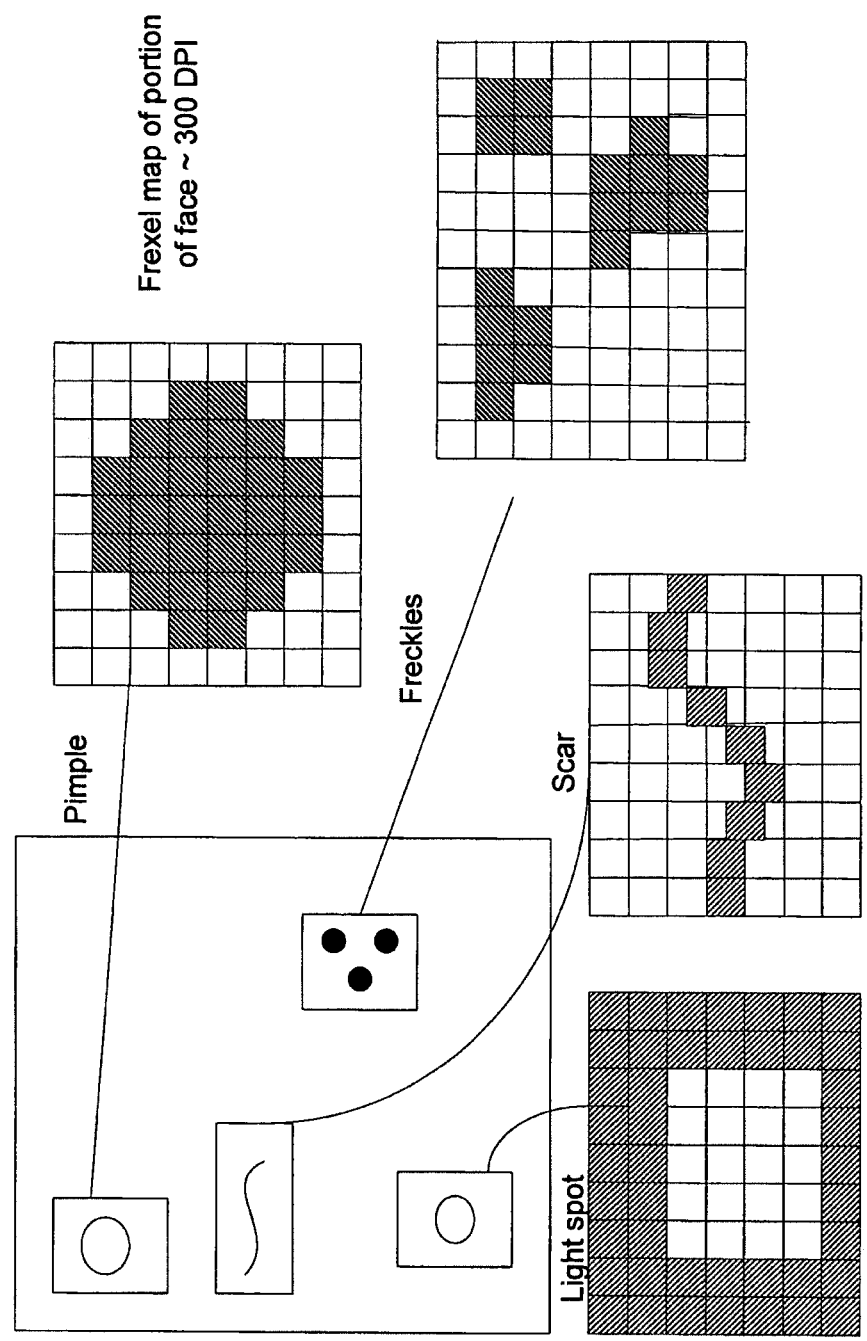
FIG. 42 is a schematic of an example for feature recognition.

FIG. 42 illustrates a frexel map for a portion of a face. This figure shows characteristics such as a pimple, frexel, light spot and a scar. Each of those characteristics is shown in an enlarged position with multiple frexels in the diagram. These areas can be represented and detected mathematically from the known properties of the various skin features, so that feature recognition can be preformed automatically with mathematical analyses.

Artistic Strategy

Figure 43:
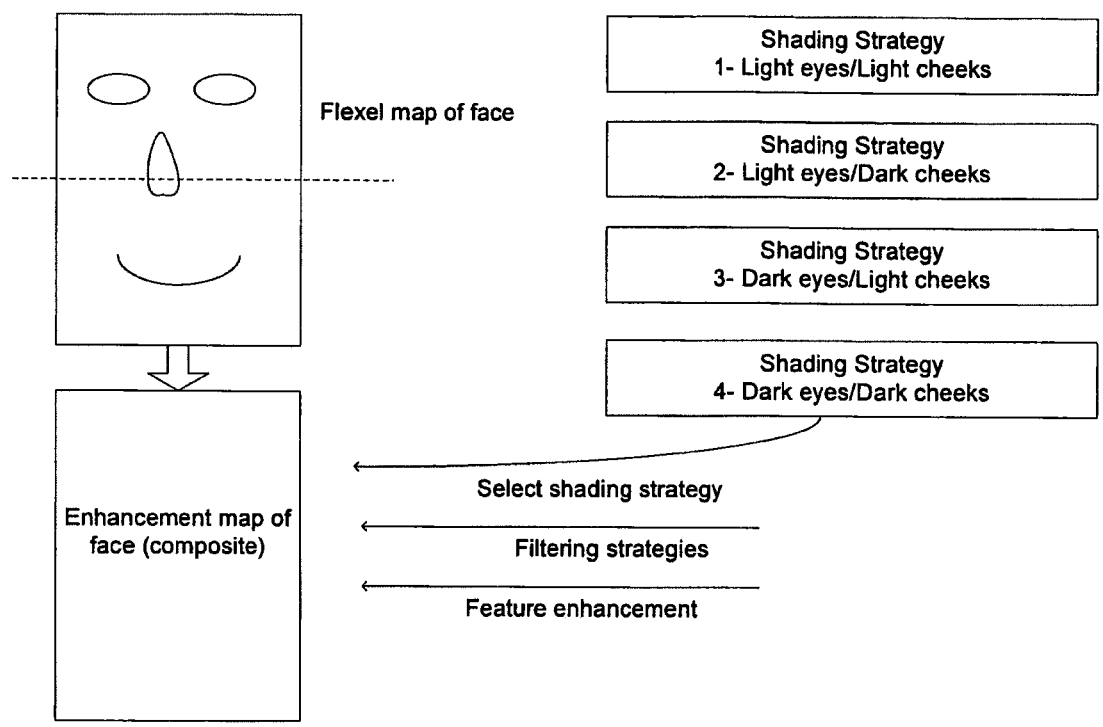
FIG. 43 is a schematic of an artistic strategy for applying RMAs.

FIG. 43 represents an example of simple artistic strategy. When a frexel map of a face is generated, various shading strategies or overall global strategies for appearance can be provided. For example, one strategy involves the selection of white or dark areas in the upper or lower portion of the faces, such as light eyes and light cheeks, or light eyes and dark cheeks, or dark eyes and light cheeks, or dark eyes and dark cheeks. Each of these general shading strategies provides a very distinctive look for a particular subject and may be appropriate either the particular facial structure of the subject or for particular activities or objectives of the person. In this example, one of the overall shading strategies is selected, and that overall shading strategy is applied along with filtering strategies such as middle frequency removal and specific feature enhancement described above. The combination of these strategies provides the desired enhancement map of a face which is a composite of those approaches, so that a correction is applied in a combined manner.

Systems

Operating Environment for Cosmetics

FIG. 1 shows an embodiment of the present invention used to apply RMAs 264 to an area of skin 302. A party sets up an application system 200 comprising the following elements, which are explained in more detail below:

a computing environment 100—for example a personal computer, server, or portable computing device;

a scanner 220—which electronically scans data about attributes of an area of skin 302; and a means of application 240—for example a printer—which can be used to apply RMAs 264, such as ink.

The computing environment 200 further comprises an application algorithm 230;

storage 250—which may be may be non-volatile data storage;

an application map 232—which is created by application algorithm 230 to provide instructions for applications onto an area of skin 302;

a printable enhancement image 234—which is the set of instructions for applications onto an area of skin 302.

Loosely Coupled Systems

In embodiments, the elements of application system 200 may comprise discrete units and be connected through links 142 and 144, which may comprise internal connections. For example, FIG. 2 shows an embodiment of loosely connected elements for applications onto an area of skin 302. A scanner 220, printer 241, and computing environment 100 communicate over a network 130 and links 142, 144, and 146. The network 130 may comprise the Internet, a private LAN (Local Area Network), a wireless network, a TCP/IP (Transmission Control Protocol/Internet Protocol) network, or other communications system, and may comprise multiple elements such as gateways, routers, and switches. The links 142, 144, and 146 are compatible with the technology used for network 130.

A features library 274 may be used to store the characteristics of human features, for example the eye, nose, and mouth, for use by pattern recognition. The features library 274 may also be used to store idealized pattern for human features that may be used to make actual features appear more attractive. For example, an idealized pattern for human lips may be used to make actual lips appear fuller as well as redder. For the application map 232 shown in FIG. 1, a 2-D surface map 233, shown in FIG. 2, is used. The 2-D surface map typically includes a representation of depth in order to capture the shape of the face.

In addition, registration means 270, mechanical or electronic, are used for tracking the location of the scanner 220 and printer 241 relative to the area of skin 302

Combined Scanner and Printer Connected with Computer

FIG. 3 shows an embodiment where an application device 246 comprises a scanner 220 and an inkjet printer 242 to apply RMAs 264 from a reservoir 262 to the area of skin 302. The application device 246 also communicates over a network 130.

Reflectance Modifying Agents

Figure 4:
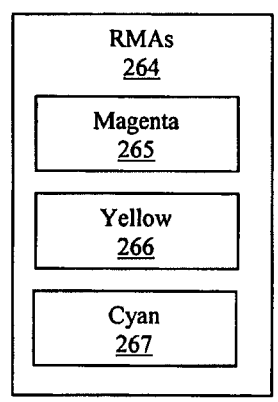
FIG. 4 is a block diagram showing the use of magenta, yellow, and cyan RMAs.

FIG. 4 shows that in an embodiment, the RMAs 264 may comprise magenta 265, yellow 266 and cyan 267 RMAs. In other embodiments, the RMAs 264 may additionally include black or brown and white.

Application Device

The application device 246 comprises the portable scanner 220 and a portable inkjet printer 242, shown in FIG. 3. In this example, the device has a height-determination means such as a tip or cup to hold the device at uniform a height of ⅛ to ¼ inch (3.2 to 6.4 mm) from skin. The elevation of the probe only has to be accurate within a few millimeters. The device uses mirrors or two cameras. It typically makes ten passes to cover the 150 square inches (1000 square cm) of a face, and the time required to complete the process is comparable to that required for electric shaving. The device is under 2 inches (50 mm) in length.

Portable Scanner

In an embodiment, the portable scanner 220 comprises an area array that lightly touches the surface of the area of skin 302 to be scanned. In another embodiment the portable scanner is moved without touching skin in the vicinity of the skin being scanned. During scanning, a white LED light source in the sensor flashes to apply normal light, defined as light from above, to the area of skin 302. Measurements are taken when the LED is on and off, and the difference between the two measurements is subtracted to determine the contribution of the light source.

Inkjet Printer

In an embodiment, the inkjet printer 242 comprises an inkjet printer with 0.001 inch resolution and a reservoir 262 capable of holding RMAs 264. In an embodiment the RMAs 264 comprise transparent dyes, while in other embodiments they comprise inks or other useful chemicals. In one embodiment, FDA-approved RMAs are employed. As shown in FIG. 4, the RMAs 264 may comprise agents for the following colors: magenta 265, yellow 266, and cyan 267. They may comprise additional colors, such as black, brown, and white, as well. These colors can enable the inkjet printer 242 to create any color on the area of human skin.

Registration Means

As mentioned above, registration means 270, mechanical or electronic, are used for tracking the location of the scanner 220 and printer 241 relative to the area of skin 302. In an embodiment, the registration means 270 may comprise accelerometers, which measure acceleration and tilt, and gimbals, which measure the rotation of an object in three dimensions and control that rotation, may also be included in the application device 246. These devices help control movement and positioning and maintain the correct reflective angle for the application device 246.

In another embodiment, registration means may comprise a global positioning-like service (GPS) used locally through high frequency radiation.

In still another embodiment, registration means may comprise a set of small flat-ended pins that are pressed lightly against the surface of the skin to make an impression. For example the pins may be pressed against a face to make a mask of the face. The movement of the pins in a frame may be tracked mechanically to provide the 3-D coordinates.

Portable Application Device

Figure 5:
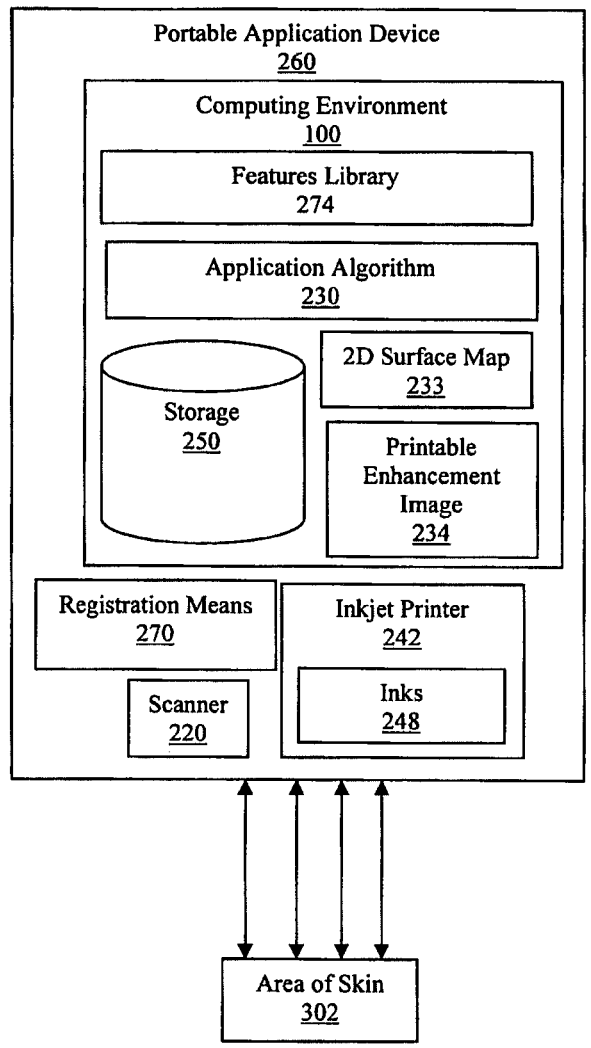
FIG. 5 is a block diagram showing an operating environment in which embodiments of the present invention may be employed through a self-contained portable application device for applying inks onto skin.

As shown in FIG. 5, another embodiment of the present invention is a portable application device 260 comprising multiple elements for applying material onto skin, which does not require an external network. An embodiment of the portable application device 260 uses an inkjet printer 242 to apply ink 248 to the area of skin 302.

Portable Application Device with Curved Surface

Figure 30:
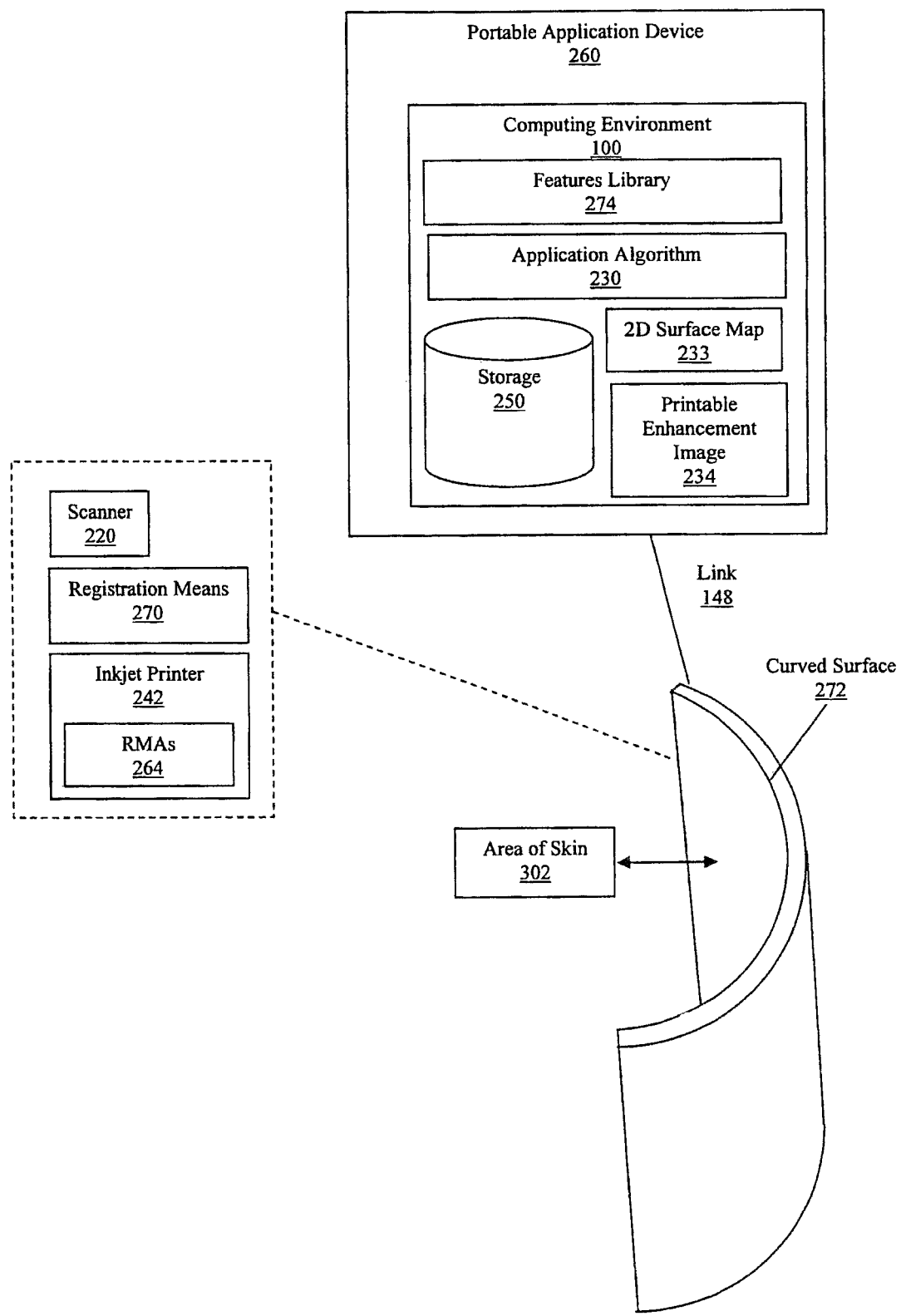
FIG. 30 is a block diagram showing an operating environment in which embodiments of the present invention may be employed for applying RMAs onto skin through communications over a network and a portable application device with a curved surface.

One aspect of the current invention is to acquire and manipulate image data of human skin. In one embodiment, a first step is used to generate a map of a portion of the body, and that map is used to generate a specific plan of selectively applying dyes at a later time. One embodiment of the current invention is to use a portable scanning device to acquire data for generating the map; and to use the portable scanning device in combination with a portable printing device to selectively apply dyes to a region of skin. FIG. 30 shows an embodiment of the present invention that may be employed for applying material onto skin, through communications over a network and a portable application device with a curved surface.

Mask or Helmet

The curved surface may comprise, for example, a mask or helmet into which a human face may be inserted and an application device (scanner/printer) that circles the face. Use of such a curve surface requires feature recognition through artificial intelligence and mapping, so that the application device can calculate its location on the face and its distance from the skin.

One advantage of the curved surface device is that is requires no user action or training. Another is that the application device remains above the skin and so does not touch the wet RMAs.

Booth

Another embodiment of the current invention is to use a booth or work station to scan a region of skin, such as a face or an entire body.

Figure 27:
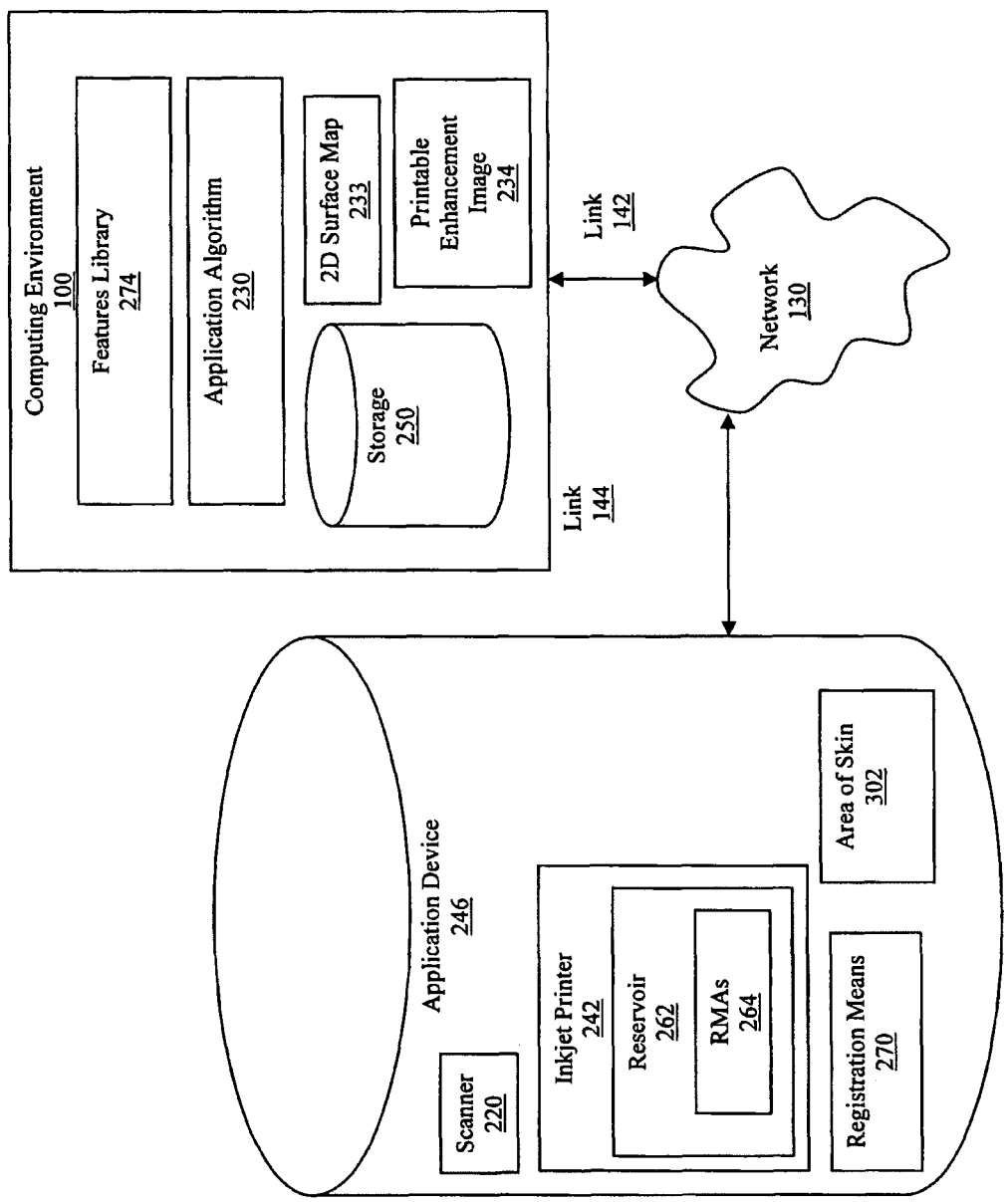
FIG. 27 is a block diagram showing an operating environment in which embodiments of the present invention may be employed for applying RMAs onto skin through communications over a network and an application device comprising a booth.
Figure 36:
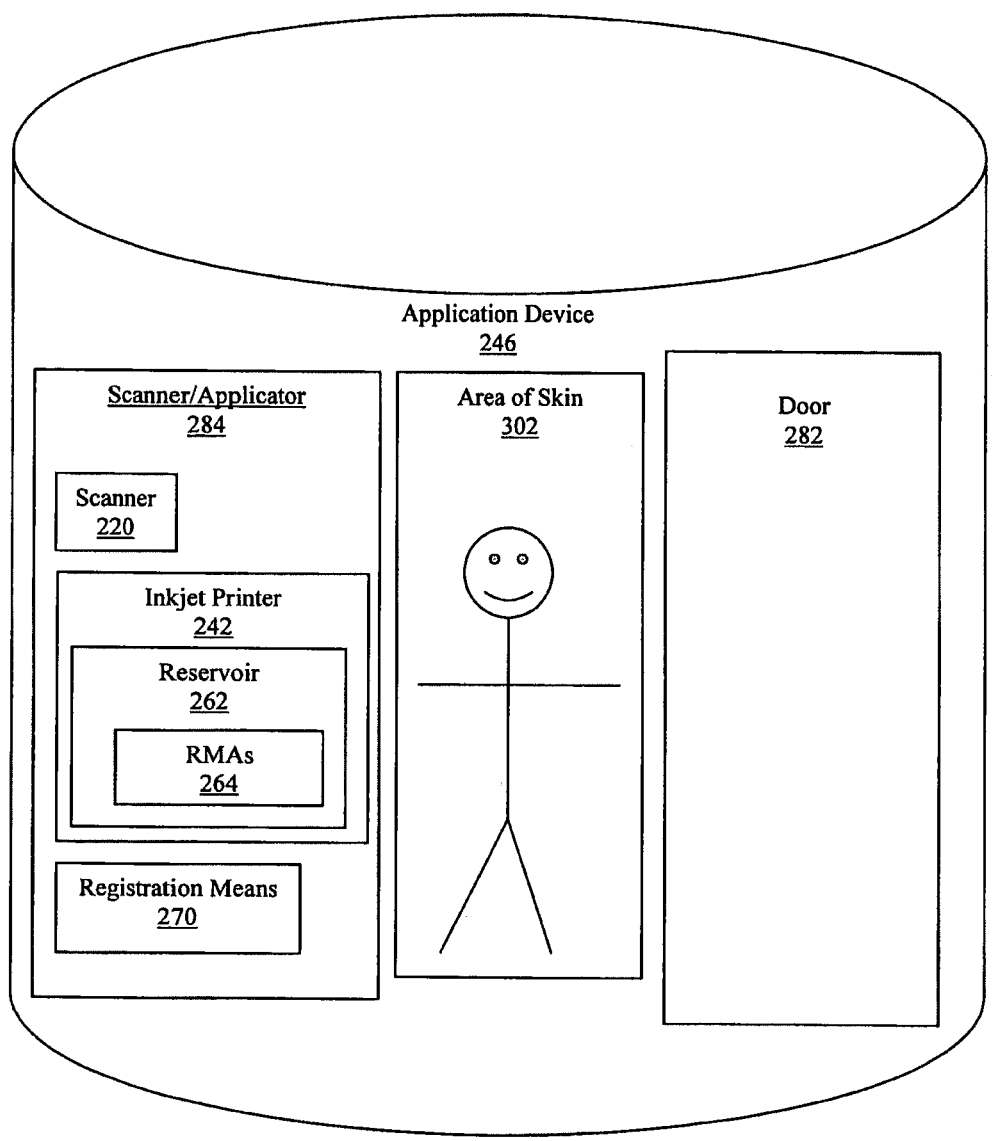
FIG. 36 is a block diagram showing an application device comprising a booth.

FIG. 27 shows an embodiment of an application device 246 comprising a booth. In this case, as shown in FIG. 36, the area of skin 302 comprises an entire person who steps into the application device 246 through a door 282. The person might undress, step into the booth, as is typically done with tanning booths, and lie or stand for the application of RMAs. A scanner/applicator 284, comprising a scanner 220, inkjet printer 242 with a reservoir 262 and RMAs 264, and registration means 270, would move across the person's body to collect data, analyze the data, and make enhancements by applying RMAs.

In another embodiment, the booth may comprise a two-part cylinder that closes over all a person or over part of a person such as a face.

Blotter

Figure 29:
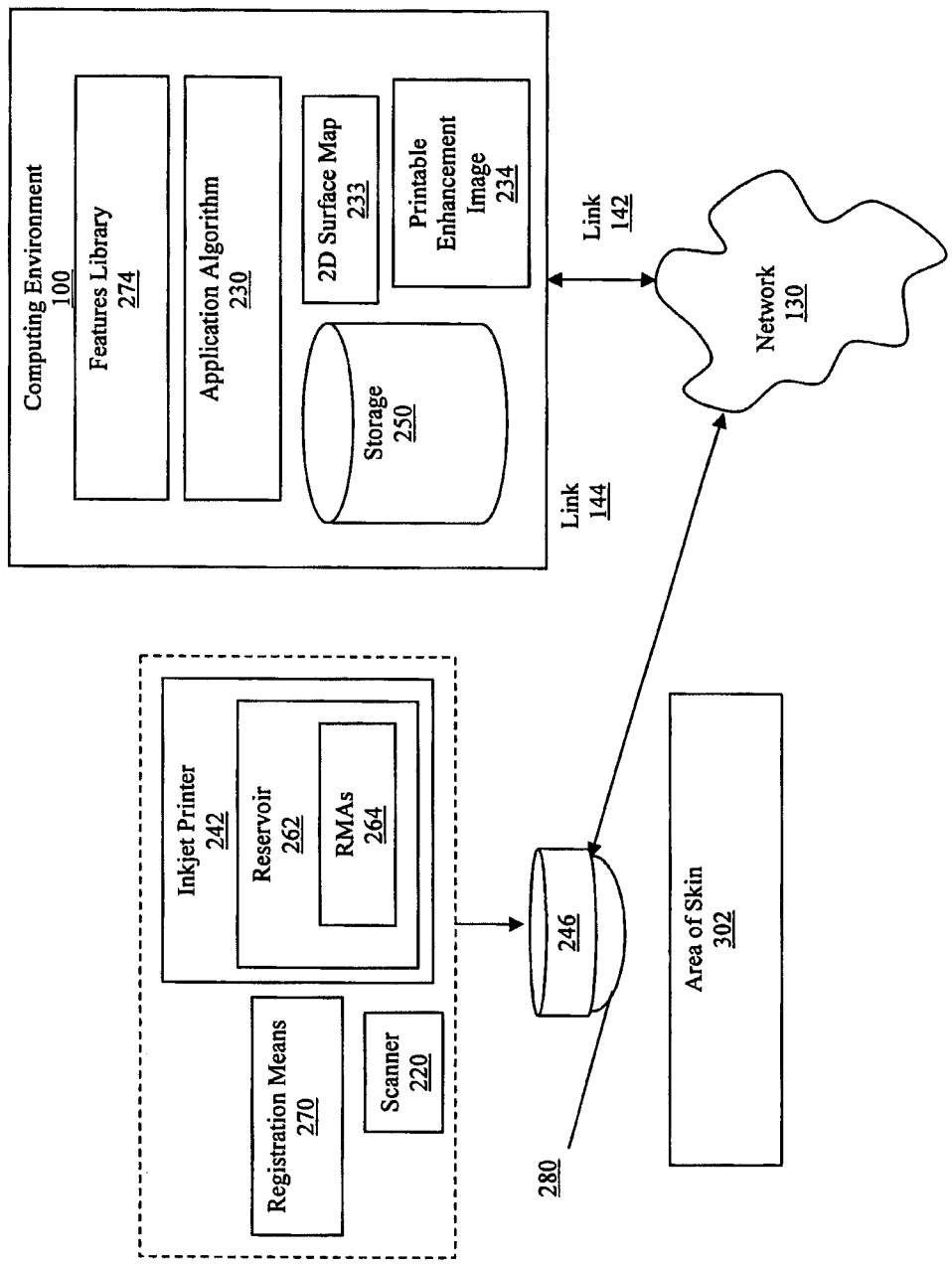
FIG. 29 is a block diagram showing an operating environment in which embodiments of the present invention may be employed for applying RMAs onto skin through communications over a network and a blotter application device.

FIG. 29 shows an embodiment with an application device 246 comprising a blotter. The blotter comprises a cup 280 to maintain an approximate appropriated distance from the area of skin 302, as explained above. Instead of moving the blotter application device 246 in a single pass or multiple passes over the enter area of skin 302, the user places the blotter application device 246 over a small area of skin and holds it there briefly, to accomplish scanning, analysis, an application of RMAs in that small area, and then moves the blotter application device 246 to the next small area.

Figure 44:
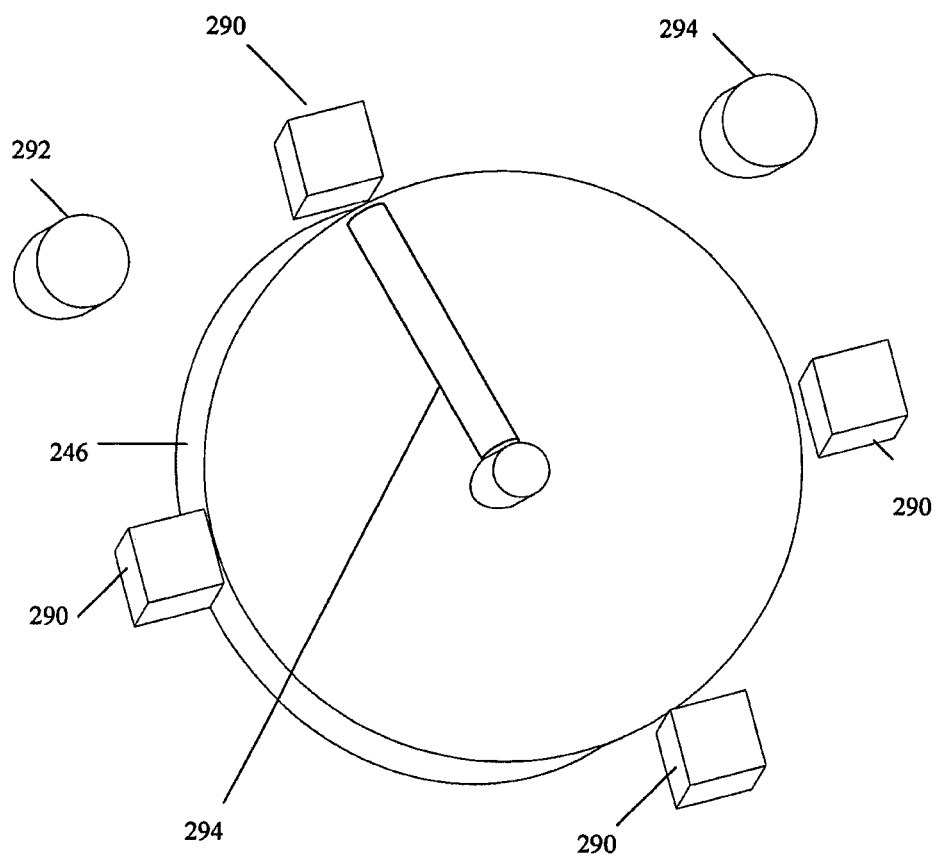
FIG. 44 is an example of a rotating printer for a blotter application device.

For the blotter application device 246, mechanical means would move the printer 242 over the area of skin 302 for the application of the RMAs 264. For example, FIG. 44 shows an inverted view of an application device 246 comprising a blotter. In an embodiment, the blotter application device 246 comprises four LEDs 290, two cameras 292, and a rotating inkjet printer 294 that moves about a central axis on the application device 246 like the hand of a clock. The rotating inkjet printer 294 prints RMAs throughout the area of the blotter application device 246 except for the area of the central axis, which can be printed on by moving the blotter to an overlapping area for a second printing.

Light Sources

FIGS. 40A-B are sample layouts for LEDs and a sensors for acquiring reflectance and skin orientation data.

In one embodiment, a set of four light sources is used, such that the light sources are placed at the corners of a diamond, where the sensor is positioned at the center of the diamond layout. This configuration simplifies the mathematical analysis for calculating surface profile.

In an embodiment, it is useful to employ mean illumination. For this, multiple diffuse or orthogonal light sources may be used, in a configuration which may include mirrors. The lights may be flashed repeated, as strobe lights, so that hundreds of images may be taken of a small area can averaged for effectiveness.

Process for Employing an Application System for Cosmetics

Figure 6:
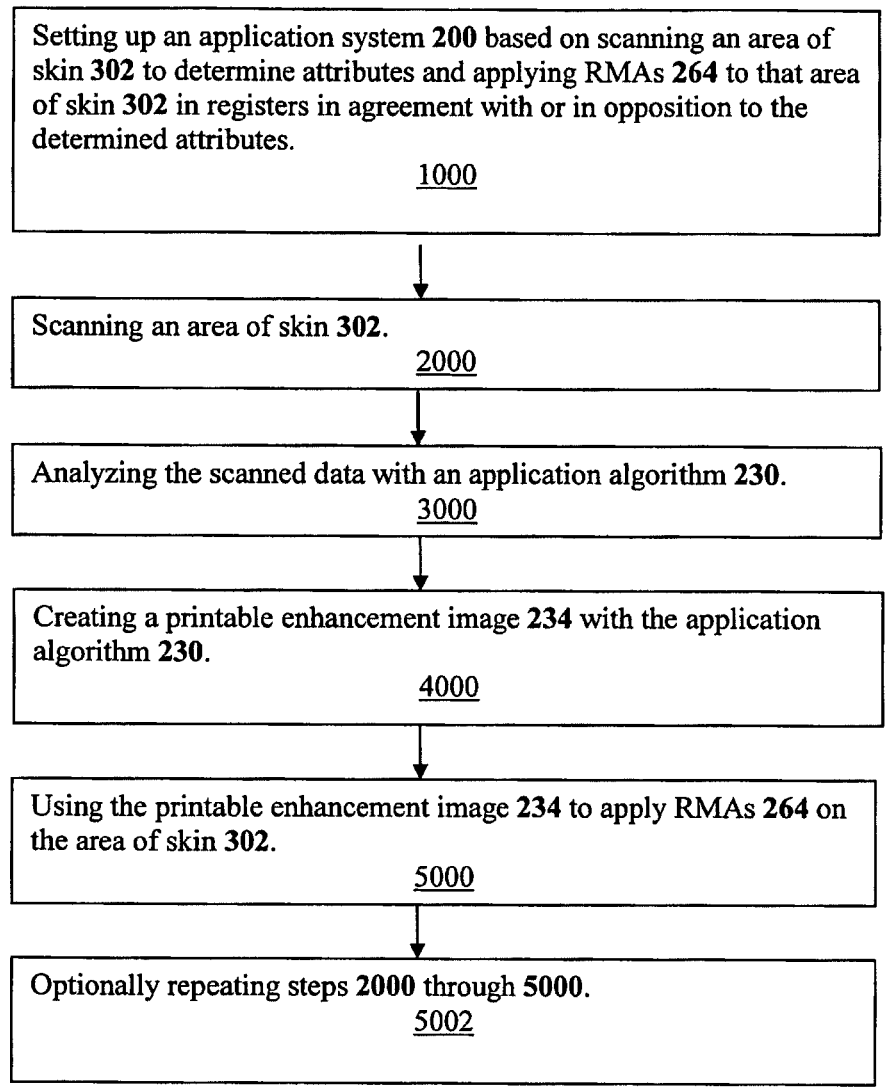
FIG. 6 is a flow chart that illustrates a process for employing an application system.

FIG. 6 shows a process for employing an application system 200, in an embodiment. This process comprises the following high-level steps, which will be explained in detail below:

Step 1000 in FIG. 6—Setting up an application system 200 based on scanning an area of skin 302 to determine attributes and applying RMAs 264 to that area of skin 302 in registers in agreement with or in opposition to the determined attributes;

Step 2000 in FIG. 6—Scanning an area of skin 302;

Step 3000 in FIG. 6—Analyzing the scanned data with an application algorithm 230;

Step 4000 in FIG. 6—Creating a printable enhancement image 234 with the application algorithm 230;

Step 5000 in FIG. 6—Using the printable enhancement image 234 to apply RMAs 264 on the area of skin 302; and Step 5002 in FIG. 6—Optionally repeating steps 2000 through 5000.

Setting Up an Application System

FIG. 7 shows a process for Step 1000—setting up an application system 200, shown in FIG. 6, in an embodiment. The process comprises the following steps, which will be explained below:

Step 1010 in FIG. 7—Providing an application algorithm 230;

Step 1020 in FIG. 7—Providing the application algorithm 230 on a computing environment 100;

Step 1030 in FIG. 7—Providing storage 250 on the computing environment;

Step 1040 in FIG. 7—Integrating a means of scanning 220 an area of skin 302; and Step 1050 in FIG. 7—Integrating a means of application 240 of RMAs 264.

Providing an Application Algorithm

One or more programmers create an application algorithm 230 that, in an embodiment, controls the elements and processes of the present invention outlined in FIG. 6 and explained above. After the application algorithm 230 has been created, it can be used on at least one computing environment 100, as shown in FIG. 1, and may be integrated with other elements of application system 200. For example, in an embodiment application algorithm 230 may be loaded on a computing environment 100 comprising a server. The computing environment 100 may be equipped with non-volatile storage 250 capable of storing data such as scanned data from scanner 220.

In various embodiments, the application algorithm can include default strategies which may be based on feature recognition, a feature-based lookup scheme, or general artistic objectives.

Figure 8:
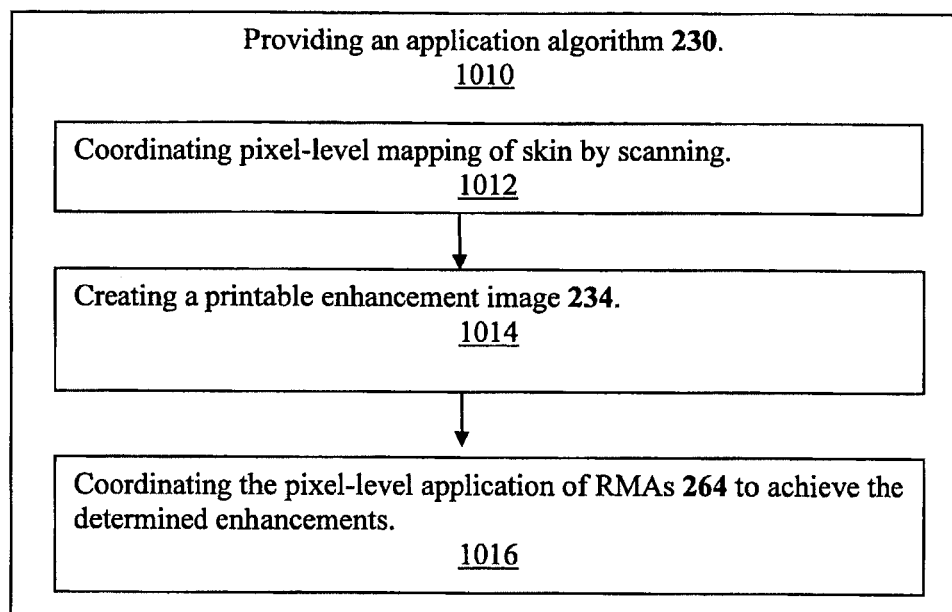
FIG. 8 is a flow chart that illustrates a process for the programming in an application algorithm in an embodiment for printing on skin.

As shown in FIG. 8, in an embodiment the general functions to be accomplished by the application algorithm 230 are Coordinating pixel-level mapping of skin by scanning; providing feature recognition, or accepting manual selection of image enhancement strategies Creating a printable enhancement image 234; and Coordinating the pixel-level application of substances to achieve the determined enhancements.

Coordinating Pixel-Level Mapping of Skin by Scanning

A primary function of the application algorithm 230 is to analyze scanned data about an area of a first instance of material 300 and create a 3-D application map 232 of the attributes of that area 300 for which application of a second instance of material 300 would be useful. A key part of this function is that the application algorithm 230 determines at each scanned point whether the application of the second instance of material should be in a register in agreement with the attributes of that area of the first instance of material or in a register in opposition to those attributes. This decision is based on instructions in the algorithm for what would be useful and advantageous for the area of the first instance of material 300.

Figure 31:
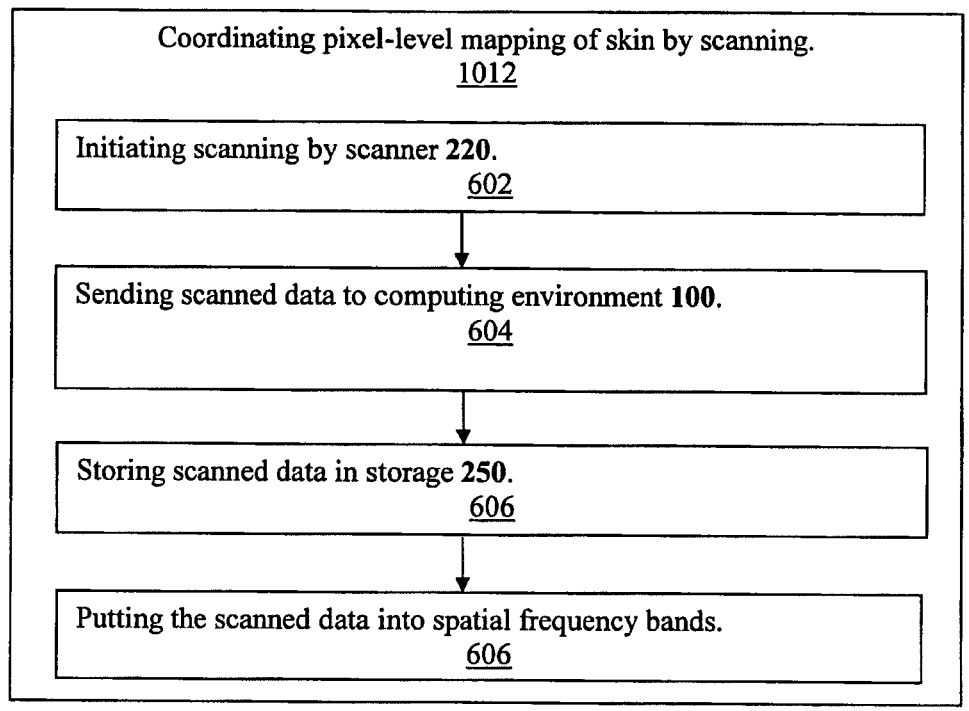
FIG. 31 is a flow chart for coordinating pixel-level mapping of skin.

FIG. 31 shows the steps involved in coordinating scanning:

Step 602 in FIG. 31—Initiating scanning by scanner 220. When the application device 246 is turned on and moved over an area of skin 302, the scanner 220 begins scanning.

Step 604 in FIG. 31—Sending scanned data to computing environment 100.

The application device 246 transmits its scanned data over link 144, network 130, and link 142 to computing environment 100.

Step 606 in FIG. 31—Storing scanned data in storage 250.

Step 608 in FIG. 31—Putting the scanned data into spatial frequency bands.

Creating a Printable Enhancement Image

The goal of a cosmetics embodiment of the present invention is to understand and make use of the characteristics of the human visual system to make the observer perceive a person as younger than that person is. This may be considered a form of camouflage performed at the pixel level. It is important to note that the techniques of the present invention for accomplishing this goal do not wipe out all the detail in the area of skin affected, but retain significant, desirable details that make the area of skin look real. To accomplish this goal, the present invention uses sophisticated techniques, explained below, to create a printable enhancement image 234 for making appropriate applications of the RMAs 264.

Figure 9:
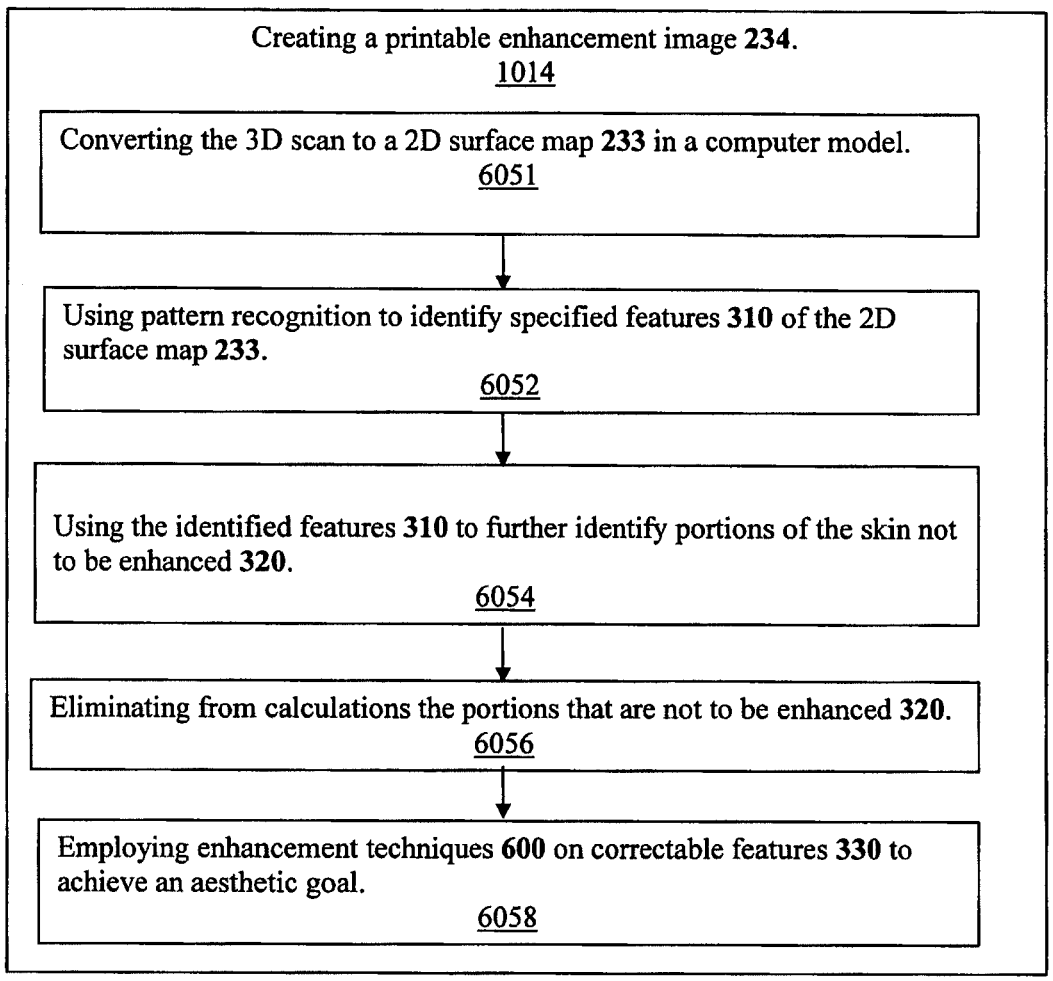
FIG. 9 is a flow chart that illustrates a process for creating a printable enhancement image.

FIG. 9 shows a process for creating a printable enhancement image 234, in an embodiment.

Step 6051 in FIG. 9—Converting the 3-D scan to a 2-D surface map 233 in a computer model.

Figure 10:
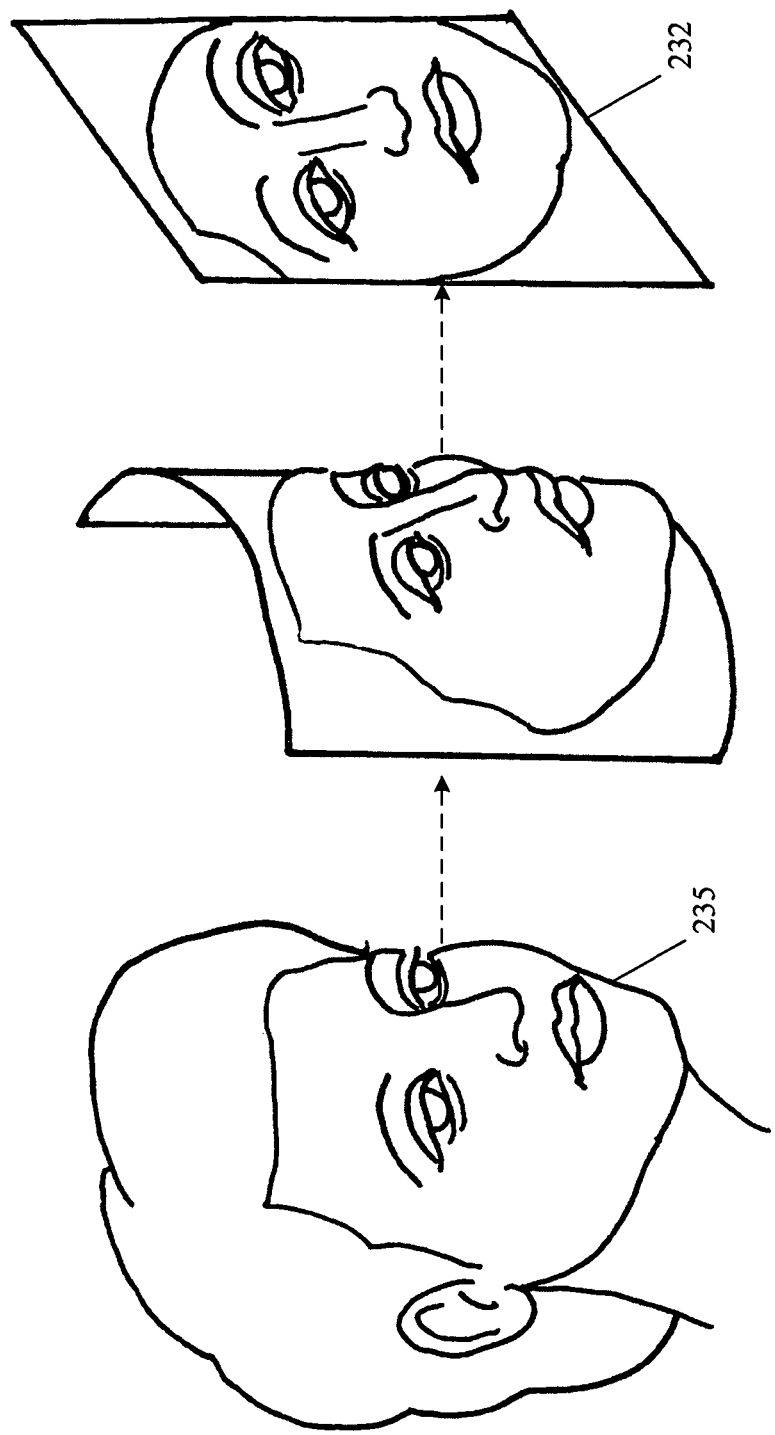
FIG. 10 is a diagram that illustrates how a 3-D object maps to a 2-D surface in a computer model.

FIG. 10 shows an example of how a 3-D human face 235 may be mapped to a 2-D surface map of that face 233, through well known techniques employs in computer modeling and gaming. For this 2-D mapping, in the small (limit) all surfaces are flat, creating a razor model for the "base."

Step 6052 in FIG. 9—Using pattern recognition to identify specified features 310 of the 2-D surface map 233.

For example, pattern recognition may be used to identify the eyes.

Step 6054 in FIG. 9—Using the identified features 310 to further identify portions of the skin not to be enhanced 320.

For example, it may be desirable to specify that the eyes not be enhanced with potentially irritating RMAs.

Step 6056 in FIG. 9—Eliminate from calculations the portions that are not to be enhanced.

For example, the eyes may be eliminated from calculations.

Step 6058 in FIG. 9—Employing enhancement techniques 600 on correctable features 330 to achieve an aesthetic goal.

The enhancement techniques employed by the present invention are explained in detail below.

Figure 32:
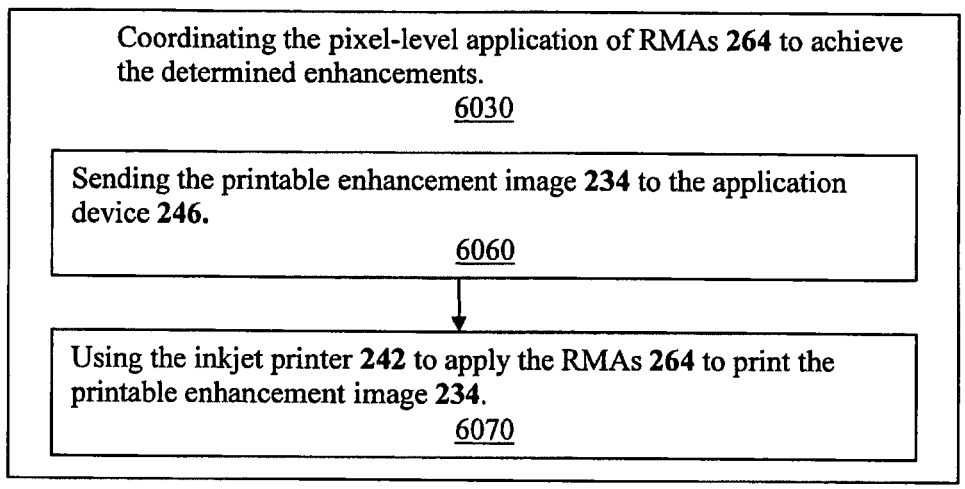
FIG. 32 flow chart for coordinating a pixel-level application of RMAs.

Coordinating the Pixel-level Application of Reflectance Modifying Agents to Achieve the Determined Enhancements As shown in FIG. 32, coordinating the pixel-level application of RMAs 264 to achieve the determined enhancements may be achieved through the following steps:

Step 6060 in FIG. 32—Sending the printable enhancement image 234 to the application device 246.

Step 6070 in FIG. 32—Using the inkjet printer 242 to apply the RMAs 264 to print the printable enhancement image 234.

Operation of an Embodiment

The operation of the present invention can be illustrated with reference to the application device 246 and computing environment 100 shown in FIG. 3.

Scanning

The user moves the application device 246 across the area of skin 302 so that the scanner 220 can record data. For example, the area of skin 302 might be the user's face. The scanner 220 sends the scanned data over the network 130 to the computing environment 100 where the data is stored in storage 250.

In an embodiment, the user may be asked to employ a tapping or blotting motion of the probe, rather and making smooth passes as in moving an electric shaver over the face. This motion reduces smudging in the application of RMAs.

In an embodiment the user may be asked assume a neutral, motionless position, to present a neutral model. For example, for use with the face, a user may be asked to hold still, close the eyes, and have an expressionless face. For use with the entire body, the user may be asked to stand still in a specified position in a booth.

Analyzing the Scanned Data

The application algorithm 230 puts the stored data into spatial frequency bands and uses pattern recognition to analyze them to determine the landscape of the area of skin 302 and the dimensions that require application of the RMAs 264.

The application algorithm 230 uses its analysis to create in software a 2-D surface map 233 of the area of skin 302, which is stored in storage 250, for potential future use.

Creating a Printable Enhancement Image

The application algorithm 230 also creates a printable enhancement image 234 based on a 2-D surface map 233.

Note that alternately the printable enhancement image 234 can be made manually by an operator who displays the map on a computer screen and uses controls to make desired adjustments.

Printing the Enhancement

The application algorithm 230 sends the printable enhancement image 234 over the network 130 to the application device 246 that triggers the inkjet printer 242 to apply the RMAs 264 from the reservoir 262 to area of skin 302. The inkjet printer 242 applies different quantities and mixes of the RMAs 264 to create desired results in different portions of the area of skin 302, at the pixel level, making the application very precise.

Single or Multiple Passes

As explained above, with sufficient computing power, the application device 246 will only need to make only one pass across the area of skin 302 to both scan the data and apply the RMAs 264.

Otherwise, the user moves the application device 246 over the area of skin 302 many times. The application system then scans continually, creates the 2-D surface map 233, uses the 2-D surface map 233 continually to identify the landscape of the area of skin 302, and uses the printable enhancement image 234 to apply approximately 10% of the RMAs 264 on each pass.

In one example, a portable printer is used to apply dye as the device is swept across or blotted onto the face. One or more scanners on the device acquire image data in a manner as described above in the mapping example. That data is used to identify the location of the scanner so that the printer can be registered to the skin. The correction plan, or in the case of multiple passes a portion of the correction plan, is applied to the skin as the printer is moved over the skin. Current ink jet printers typically have a desired working range of about ⅛ inch (3.2 mm) between the print head and the surface being printed. In one example, this print distance is maintained by hand held operation such as a light contact to the skin as the device is moved. In another example, a helmet-type guide is provided so that the scanner and printer can be directed in predetermined paths across the skin.

In various embodiments, the scanning and printing components can be provided in hand-held, fixtured, or booth systems.

Example of Hand-Held Operation

In a hand-held system, the device may be the size of an electric shaver or powder puff so that it may be blotted or moved across the skin. The device may be used in a single pass mode to provide a general smoothing of skin appearance, or in a multiple pass mode where several passes over each area of the skin are used in order to provide a relatively small correction on each pass. The system may include a feedback means such as a tone to indicate that the operation is complete.

Example of Hand-Held Scanner that Touches Skin

FIG. 26 shows a handheld scanner. In this example, the scanner housing touches the skin so that the application device, such as a printer head, is maintained at an approximate known distance and orientation with respect to the skin.

Example of Helmet Guide for Facial Modeling and Printing

A helmet mode is an example of a fixtured system where the scanning and application device has designated limited travel paths. The fixtured system may include coordinate reference points, guide strips, and a movable probe.

Application Example—Facial Makeup

For example, a user could move the application device 246 over his or her face and have RMAs 264 applied as a form of makeup to enhance the attractiveness of the face. These RMAs may comprise transparent dyes, or inks, or pigments that would even up the skin tone while retaining desirable details like beauty moles, add reddish color to cheeks, and hide flaws and scars in the skin, greatly enhancing the attractiveness of the skin to the human eye. Typically, in an embodiment the user would close his or her eyes and mouth to prevent exposure of them to the RMAs 264. In another embodiment the system would use feature identification to recognize sensitive areas such as eyes and restrict itself from applying RMAs 264 to those sensitive areas.

Touchups

Once a 2-D surface map 233 and a printable enhancement image 234 for that face has been stored, they can be used repeatedly to quickly apply the RMAs 264 to the face with the application device 246, for example for quick daily cosmetic touchups.

Note that the printable enhancement image 234 may be both in a register in agreement with the attributes of areas of the face or in a register in opposition to those attributes. For example, a light area of skin may be left relatively light or may be darkened, depending on the desired effect calculated by the application algorithm 230.

Examples of Applications of the Present Invention

Facial makeup;
Suntan lotion ingredients could be added, such as SPS 15 sun block. For example, a mother might spray her child once a month for both appearance and sun protection.
Lipstick;
Eye-liner,
Eyebrow makeup and shaping;
Tanning;
Nail polish;
Simulated nylon stockings;
Tattoos and specialty designs—permanent and temporary;
Facial masks, for example for Halloween;
Body painting;
Streaking Hair;
Camouflage;
For example, to camouflage attributes of an area of skin, lighten areas on the bottom of the area of skin and darken areas on the top, since this reverses the natural and thus expected pattern with light from above.
Severe Trauma makeup.
For example, makeup may be applied to simulate eyebrows on cancer patients who have lost their facial hair through chemotherapy or radiation treatments.

Tanning

In this embodiment, a device is provided to provide an artificial tanning that creates improved appearance over prior art devices.

Advantages and Disadvantages of Tanning Techniques

Natural tanning through exposing the skin to sunlight or to light in tanning booths is a popular way that people use to increase their attractiveness. Natural tanning tends to smooth skin's appearance, which makes skin look more youthful. For example, unattractive flaws such as age spots, bumps, wrinkles, and pock marks typically appear in people's skin as they age. The human eye perceives these flaws because they create contrasts in the lightness and darkness of areas of the skin, making the skin appear more irregular and less smooth. An age spot is typically darker than the areas around it. A bump often casts a shadow beneath it, in natural lighting conditions when the sun shines from above the person. A wrinkle is like a recessed trough in the skin, so that it is less exposed to light and has a darker appearance than the surfaces around it. Pock marks are similarly darker areas.

Natural tanning smoothes the appearance of such flaws by reducing contrasts of lightness and darkness on the surface of the skin. When an existing age spot is exposed to the sun, it typically is protected by its melanin so that it darkens to a limited degree, but the skin around it that is not protected by the same level of melanin darkens to a greater degree. The contrast between the age spot and surrounding skin thus becomes less. Similarly, a raised area such as a bump receives more sunlight on the upward facing side and therefore darkens more through exposure to sun than a shadowed area beneath the bump. The effect is to counter the dimensional appearance visualized by the shading. Areas around wrinkles and pock marks are darkened more than the shaded areas within them. Therefore, the darker central line of a wrinkle is relatively lightened, camouflaging the wrinkle. Even though the smoothing effect of natural tanning lies in these reductions of contrast, not in darkening skin per se, tans have become cultural norms of beauty in themselves in many circumstances such as summer days at the beach.

Although tanning through sunlight or artificial light can certainly make skin appear smoother and more attractive, it has significant disadvantages. The weather is not always warm and sunny, and tanning booths charge for their services. Worst of all, exposing skin to increased UV light can unfortunately cause significant damage to the skin, such as skin cancer.

As a result, products such as tanning creams and spray-on lotions have been developed to simulate the attractive effects of tanning by darkening the appearance of the skin without exposing the skin to increased light. However, these products are typically not as successful in creating the illusion of smoothing skin, for the simple reason that they tend to darken all the areas of skin to which they are applied to the same degree, preserving the contrasts in lightness and darkness that make skin less attractive. For example an age spot is darkened and the area around is also darkened, so that the age spot is still darker than its surrounding area. Similarly, both the upper and lower portions of a bump are darkened, so that in normal lighting conditions with light from above, the lower portion of the bump is still darker than the upper portion. In addition, these products are manual and expensive, and their techniques are not precise enough to make specific enhancements at the pixel level, limiting their effectiveness.

Automatic Scanning, Analysis, and Pixel-Level Application to Simulate Tanning

In contrast, the present invention makes enhancements targeted to specific ranges of scanned spatial frequencies in a frexel to simulate natural tanning. This allows patterns in some spatial frequencies to be altered but patterns in other frequencies to be retained, through the application of an RMA of a single color, such as a brown or melanin color, to enhance attractiveness. For example, an RMA can be applied to reduce the contrast between areas of lightness and darkness by darkening selective areas of the skin, while retaining warm areas of colors, young-looking freckles, and beauty marks. Typically the RMA is applied in opposition to the data obtained by scanning, to darken selected light areas. The scanned data is analyzed to identify its reflectance and its topography, both of which are useful for determining precisely which frexels are to be darkened. Surface angles of features on the skin can be determined, as is done in gaming, to identify shading of surface textures.

To achieve an attractive smoothing effect, this process would not have to darken the skin as much as natural tanning by light requires. This is because this process can make very specific enhancements at the pixel level. For example, it can distinguish a darker age spot from a lighter area of skin, can specifically darken only the lighter area, and can darken the lighter area only to the lowest degree useful for visual enhancement.

Camouflaging a Bump Through Simulated Tanning

The present invention can identify a very small area with surface texture variations 400, shown in FIG. 12, representing a tiny bump, for example. It can apply an ink or dye to the apparently lighter portion 404 of the bump 400, apparently lighter because it is receiving more illumination by virtue of the surface angle relative to the light source, and not darken the shaded, apparently darker portion 406 underneath the bump. This reduces the light and dark contrast associated with the dimensionality of the bump, making the skin look smoother.

Enhancing the Whole Skin through Simulated Tanning

By similarly making specific, pixel-level enhancements to potentially hundreds of thousands of bumps and other small irregularities on the skin, the overall visual perception of smoothness of the skin is greatly enhanced. For example, the lighter areas around wrinkles can be darkened, but not the recessed areas within the wrinkles, which tend to be shaded and thus already apparently dark, thereby camouflaging the wrinkles.

As a result, the skin will look darker overall, as with a natural tan, and attractively smoother, but desirable features such as freckles and color in the cheeks can be left un-enhanced and so can be retained, unlike the application of a darker base.

One-Color Enhancements Through Simulated Tanning

The simulated tanning of the present invention provides for cosmetic enhancements througth the use of an ink or dye, or a chemically altering darkening agent, for example compounds used to simulate tanning, in one color instead of multiple colors such as cyan, magenta, yellow.

Because the human eye has less resolution for color than for luminance, enhancements that affect luminance alone may still greatly enhance perceived uniformity and attractiveness, even when used to camouflage colored defects such as acne or varicose veins.

Simulated Tanning for Enhancements to Large Areas

The techniques of the present invention may be applied not only to very small features, such as the bump 400, shown in FIG. 12, but to much large areas for skin. For example, it may be used to simulate muscle definition and to make breasts or cheekbones project by darkening the lower portions of these features, and lightening cleavage.

Handheld Mark Applicator

FIG. 47A is a side view of one embodiment of a handheld device for skin marks such as age spots, small scars, and varicose vein. FIG. 47B is a front view of the device of FIG. 47A, and FIG. 47C is a top cross sectional view along section AA' of FIG. 47B.

The mark applicator device 550 includes a housing 553 which provides an upper handle portion and a lower skin application portion. In this example, the device is about 1½ by 2 inches (38-50 mm) wide and about 4-5 inches (100-127 mm) tall. In this example, an opening in bottom 554 of the housing is about ½ to ¾ inch square (12.7-19.2 mm square).

At least one light source is used. In this example, four light sources 551 are positioned in proximity to the 4 corners of a square tube. The light sources are typically white light LEDs, or combinations of LEDs such as red, green, and blue to produce a white light, but the sources may also be of varying wavelengths to provide additional data for mark recognition. In some cases, a single light source may be used. The advantages of using separate wavelength light sources include greater sensitivity, better color accuracy, and higher resolution. In the booth and movable handheld embodiments described above, however, these advantages may not overcome the practical difficulties and time required to sequence four different lighting conditions for each set of frexels. Most cameras are able to provide good color images from a white light source.

In the current embodiment, however, the camera is not moved, and it is more practical to obtain an image from each of several colors of light sources, and from the white light produced when all of the light sources are on. Thus some examples of this applicator include light sources of different wavelengths, thus providing a better white light and additional image data at a plurality of wavelengths in order to support more sophisticated feature recognition.

In general, the light source or sources in this and other embodiments may be of a variety of wavelengths including visible light, infrared, and ultraviolet. The infrared wavelengths provide a better penetration of the skin to support feature recognition.

The lower portion of the tube preferably has a reflective surface such as a shiny or brushed aluminum or steel so that the light sources reflect from the housing walls and provide a uniform lighting to the exposed skin area. These reflective surfaces are analogous to an optical fiber. A camera 552 captures images of the exposed area as described below. A print head 560 is moved across the opening in order to print a desired correction to the area, and to the mark in particular. Other components in the housing include a circuit board 562 and electronics; at least one RMA cartridge 564 and a battery 566. The term RMA is used here in the general sense and the cartridge or cartridges may contain pigments or other agents.

In operation, at step 7900 the device is placed over an area of skin which has a mark which the user desires to camouflage. The device is held in place for a predetermined period of time, or until the unit signals completion, such as with a status light or audible tone. The user then presses a switch on the housing (not shown) and the unit performs the following typical operations:

In response to the user pressing a switch on the housing at step 7910, the unit completes the following steps.

At step 7920, the camera captures a first image at ambient light with the camera of the area of skin exposed by the bottom opening. Even when the unit is pressed against the skin, some light travels through the skin and partially illuminates the area.

At step 7930, the light sources are turned on.

At step 7940, the camera captures a second image with the camera while the light sources are on.

At step 7950, the unit analyzes the images, which may include the following steps. Subtracting the first image from the second image at step 7952; identifying the mark at step 7954; and determining a desired modified reflectance for the mark and adjacent skin at step 7956.

At step 7960, determining a desired amount of RMA to print on the mark to achieve the desired modification. A generally opaque and white RMA would typically be used to camouflage the small marks of this embodiment. The substance would be similar to a classical makeup base, but typically lighter or more white that the base. In one example, the RMA is a pure white, or is white in one wavelength, such as a light pink. The RMA is preferably lighter than the skin so that small amounts may be used over a mark in a manner than matches surrounding skin.

At step 7970, printing the correction in one or more print head passes. One example print method includes printing a portion of the desired correction in a first pass at step 7972; taking an image of the area of skin after printing the first portion at step 7974; analyzing the image at step 7976; adjusting the amount to be printed in the second pass according to the analysis of the image at step 7978; and printing at least a portion of the remaining correction amounts in a second pass at step 7979. Additional passes may be performed if desired. A "pass" in this example refers to the print head being moved over the skin area. All other components and the housing remain stationary. The second pass provides an opportunity to compare the predicted correction to the actual correction, and to compensate for the difference. For instance if less correction is printed than desired, the unit may print more than the remaining calculated amount in a second pass; and if more correction is printed than desired, then the unit may print less than the remaining calculated amount in a second pass.

Specialized Skin Region Applicator

In this embodiment, a unit is provided to print a specialized area of the skin such as lips, or around the eyes. The unit may be provided as a booth-type fixture, but is preferably portable, such as a handheld device. The device may include a portable support such as a chinrest to provide stability and alignment.

In an example embodiment for lips and surrounding skin areas, a device similar to the handheld mark applicator of the embodiment described above may be used. The unit typically has several differences to the mark applicator. In this example, the unit is typically larger than the mark applicator, and the opening, may be of a shape such as an ellipse which more closely matches the skin region. Since the skin region may have substantial curvature, the print head typically has a z-axis capability to be moved closer to the skin or further from the skin as the head is moved over the region.

The multiple light sources as described in the above embodiment are effective for providing a "shading" analysis of frexel orientation over small areas. Since a region like the lips has larger shape features as well as local features, it is desirable to supplement the shading analysis with stereoscopy methods. For instance the use of two camera permits a comparison of the images to develop a stereoscopic analysis of the region, as well as a local shading analysis. The two approaches are thus complimentary.

In this example, the device is placed over the lips; or in the case of a booth device, the lips are placed in the booth. Images are taken by a pair of cameras with multiple lights sources under various lighting conditions. The image data from one or both cameras can be used to determine frexel orientation as described above. The image data from both cameras can also be used to develop a stereoscopic analysis.

The analysis is used to develop a correction plan. The correction plan is executed by moving the print head over the region to apply one or more RMA—preferably in multiple passes. In this example, the print head has a z-axis control so that the head may be brought closer to the lips or further from the lips as necessary.

Alternate Embodiments

For Other Surfaces than Skin

The present invention may be used to apply substances to other surfaces than skin, for example
  To foods such as cakes, cookies, other desserts, vegetables, fruits, meats, and fish to enhance their appearance or improve there nutritive content;
  To plants, including leaves and flowers, to enhance their appearance;
  To clothing, furniture, walls, and floors to enhance their appearance; and
  To any absorptive surface.

Other Hardware and Software

It will also be apparent to those skilled in the art that different embodiments of the present invention may employ a wide range of possible hardware and of software techniques. For example the communication between a Web service provider and client business computers could take place through any number of links, including wired, wireless, infrared, or radio ones, and through other communication networks beside those cited, including any not yet in existence.

Also, the term computer is used here in its broadest sense to include personal computers, laptops, telephones with computer capabilities, personal data assistants (PDAs) and servers, and it should be recognized that it could include multiple servers, with storage and software functions divided among the servers. A wide array of operating systems, compatible e-mail services, Web browsers and other communications systems can be used to transmit messages among client applications and Web services.

What is claimed is:

1. A method to change an appearance of a region of human skin, the method comprising:
  receiving, by a computing environment and from a sensor of a handheld apparatus, one or more images of the region of human skin, the region of human skin containing a plurality of frexels;
  processing, by the computing environment, the one or more images to determine reflective properties of at least two frexels of the plurality of frexels;
  comparing, by the computing environment, the reflective properties of the at least two frexels to determine a reflectance pattern; and
  providing an instruction, by the computing environment to an inkjet printer of an application head of the handheld apparatus, to apply, based on the reflectance pattern, a substance comprising a reflective modifying agent to selected frexels of the plurality of frexels and not to apply the reflective modifying agent to other frexels of the plurality of frexels to change the appearance of the region of human skin while the application head of the handheld apparatus is passing over the region of the human skin.

2. The method of claim 1, wherein applying the substance is based on a map of the region of the human skin and an idealized map of the region of the human skin.

3. The method of claim 2, wherein applying the substance comprises:
  generating the map of the region of human skin, the map comprising a location and a reflectance of the at least two frexels of the plurality of frexels;
  generating the idealized map of the region of the human skin which comprising selectively removing a portion of components from the map of the region of the human skin; and determining an amount of the substance based on a difference between the map and the idealized map of the region of the human skin.

4. The method of claim 2, wherein determining the reflectance pattern comprises determining local skin morphology, wherein the idealized map is provided based on the local skin morphology.

5. The method of claim 1, wherein applying the substance comprises applying an additional substance to the selected frexels of the region of the human skin.

6. The method of claim 1, further comprising:
generating a plurality of spectral bands from the one or more images of the region of the human skin; and
identifying a feature within the one or more images of the region of the human skin based on the plurality of spectral bands, the feature corresponding to a reflective pattern.

7. The method of claim 1, further comprising:
identifying a plurality of features within each of the one or more images, at least one feature of the plurality of features comprising the selected frexels; and
generating a map of the region of the human skin based on the plurality of features, wherein applying the substance is further based on the map.

8. The method of claim 7, wherein applying the substance is based on the map and a library of idealized features.

9. The method of claim 1, wherein the other frexels comprise respective neighboring frexels of each frexel of the selected frexels.

10. The method of claim 1, wherein applying the substance comprises subtracting the reflective properties of the selected frexels from the reflective property of the other frexels.

11. The method of claim 1, wherein applying the substance comprises minimizing a difference between the reflective properties of the selected frexels and an averaged reflective property of the other frexels.

12. The method of claim 1, wherein the reflective property of each frexel of the selected frexels is provided based on a previous application of the substance using an application head of the handheld apparatus.

13. A system to change an appearance of a region of human skin, the system comprising:
an apparatus comprising an application head comprising an inkjet printer, and a sensor for generating one or more images of the region of the human skin, the region of the human skin being allocated into a plurality of frexels; and
a computing environment in communication with the apparatus and operable to perform operations comprising:
receiving the one or more images of the region of the human skin;
processing the one or more images to determine reflective properties of at least two frexels of the plurality of frexels;
comparing the reflective properties of the at least two frexels to determine a reflectance pattern; and
providing an instruction, by the computing environment to the inkjet printer of the application head, to apply, based on the reflectance pattern, a substance comprising a reflective modifying agent to selected frexels of the plurality of frexels and not to apply the reflective modifying agent to other frexels of the plurality of frexels to change the appearance of the region of human skin while the application head of the apparatus is passing over the region of the human skin.

14. The system of claim 13, wherein the other frexels comprise respective neighboring frexels of each frexel of the selected frexels.

15. The system of claim 13, wherein the sensor comprises a camera.

16. An apparatus to change an appearance of a region of human skin, the apparatus comprising:
a sensor for generating one or more images of the region of the human skin, the region of the human skin being allocated into a plurality of frexels;
a computing environment in communication with the sensor and operable to perform operations comprising
receiving the one or more images of the region of the human skin;
processing, using a computing environment, the one or more images to determine reflective properties of at least two frexels of the plurality of frexels;
comparing the reflective properties of the at least two frexels to determine a reflectance pattern; and
providing an instruction, to an inkjet printer of an application head, to apply, based on the reflective pattern, a substance comprising a reflective modifying agent to selected frexels of the plurality of frexels and not to apply the reflective modifying agent to other frexels of the plurality of frexels; and
the application head in communication with the computing environment and configured to apply the substance to the selected frexels to change the appearance of the region of human skin while passing over the region of the human skin.

17. The apparatus of claim 16, wherein the other frexels comprise respective neighboring frexels of each frexel of the selected frexels.

18. The apparatus of claim 16, wherein the sensor comprises a camera.

19. A method to change an appearance of a region of human skin, the method comprising:
receiving, by a computing environment and from a sensor of a handheld apparatus, one or more images of the region of human skin, the region of human skin containing a plurality of frexels;
processing, by the computing environment, the one or more images to determine reflective properties of at least two frexels of the plurality of frexels;
comparing, by the computing environment, the reflective properties of the at least two frexels to determine a reflectance pattern; and
generating the map of the region of human skin, the map comprising a location and a reflectance of the at least two frexels of the plurality of frexels;
generating an idealized map of the region of the human skin by selectively removing a portion of components from the map of the region of the human skin; and
determining an amount of the substance based on a difference between the map and the idealized map of the region of the human skin;
providing an instruction, by the computing environment to an application head of the handheld apparatus, to apply, the amount of the substance based on the reflectance pattern, a substance comprising a reflective modifying agent to selected frexels of the plurality of frexels and not to apply the reflective modifying agent to other frexels of the plurality of frexels to change the appearance of the region of human skin while the application head of the handheld apparatus is passing over the region of the human skin.

\* \* \* \* \*